US010837025B2

(12) United States Patent
Han et al.

(10) Patent No.: US 10,837,025 B2
(45) **Date of Patent: *Nov. 17, 2020**

(54) CONTROL OF CELLULOSE BIOSYNTHESIS BY OVEREXPRESSION OF A TRANSCRIPTION FACTOR

(71) Applicant: Board of Trustees of Michigan State University, East Lansing, MI (US)

(72) Inventors: Kyung-Hwan Han, Okemos, MI (US); Jae-Heung Ko, Suwon (KR); Won-Chan Kim, Okemos, MI (US); Joo-Yeol Kim, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/478,661

(22) Filed: Apr. 4, 2017

(65) Prior Publication Data

US 2017/0298375 A1 Oct. 19, 2017

Related U.S. Application Data

(63) Continuation of application No. 14/381,040, filed as application No. PCT/US2013/027777 on Feb. 26, 2013, now Pat. No. 9,650,643.

(60) Provisional application No. 61/603,823, filed on Feb. 27, 2012.

(51) Int. Cl.
*C12N 15/82* (2006.01)
*A01H 5/00* (2018.01)

(52) U.S. Cl.
CPC ........... *C12N 15/8246* (2013.01); *A01H 5/00* (2013.01)

(58) Field of Classification Search
None
See application file for complete search history.

(56) References Cited

U.S. PATENT DOCUMENTS

| | | | | |
|---|---|---|---|---|
| 7,223,904 | B2 | 5/2007 | Heard et al. | |
| 7,598,429 | B2 * | 10/2009 | Heard | C07K 14/415 800/290 |
| 8,173,866 | B1 | 5/2012 | Bao et al. | |
| 8,937,219 | B2 * | 1/2015 | Hertzberg | C12N 15/8261 800/290 |
| 9,650,643 | B2 * | 5/2017 | Han | C12N 15/8246 |
| 9,944,939 | B2 | 4/2018 | Han et al. | |
| 2003/0088057 | A1 | 5/2003 | Traugh et al. | |
| 2010/0107279 | A1 | 4/2010 | Ratcliffe et al. | |
| 2015/0052641 | A1 | 2/2015 | Han et al. | |
| 2015/0133651 | A1 | 5/2015 | Han et al. | |

FOREIGN PATENT DOCUMENTS

| | | | |
|---|---|---|---|
| EP | 2410060 | A1 | 1/2012 |
| WO | WO-2012103555 | A2 | 8/2012 |
| WO | WO-2013130456 | A2 | 9/2013 |
| WO | WO-2013130456 | A3 | 9/2013 |
| WO | WO-2020006465 | A1 | 1/2020 |

OTHER PUBLICATIONS

Ko et al 2009 The Plant Journal 60:649-665 (reference provided in parent application) (Year: 2009).*
Li et al. 2003 PNAS 8:4939-4944 (Year: 2003).*
Bosca et al 2006 Plant Physiology 142:1353-1363 (Year: 2006).*
"U.S. Appl. No. 14/381,040, Non Final Office Action dated Apr. 22, 2016", 6 pgs.
"U.S. Appl. No. 14/381,040, Notice of Allowance dated Jan. 9, 2017", 7 pgs.
"U.S. Appl. No. 14/381,040, Notice of Allowance dated Oct. 5, 2016", 7 pgs.
"U.S. Appl. No. 14/381,040, Preliminary Amendment filed Aug. 26, 2014", 3 pgs.
"U.S. Appl. No. 14/381,040, Response filed Mar. 15, 2016 to Restriction Requirement dated Jan. 15, 2016", 6 pgs.
"U.S. Appl. No. 14/381,040, Response filed Sep. 22, 2016 to Non Final Office Action dated Apr. 22, 2016", 8 pgs.
"U.S. Appl. No. 14/381,040, Restriction Requirement dated Jan. 15, 2016", 4 pgs.
"U.S. Appl. No. 14/540,320, Advisory Action dated Oct. 26, 2016", 3 pgs.
"U.S. Appl. No. 14/540,320, Final Office Action dated Aug. 8, 2016", 9 pgs.
"U.S. Appl. No. 14/540,320, Non Final Office Action dated Feb. 25, 2016", 7 pgs.
"U.S. Appl. No. 14/540,320, Preliminary Amendment filed Dec. 17, 2014", 3 pgs.
"U.S. Appl. No. 14/540,320, Response filed May 25, 2016 to Non Final Office Action dated Feb. 25, 2016", 10 pgs.
"U.S. Appl. No. 14/540,320, Response Filed Oct. 10, 2016 to Final Office Action dated Aug. 8, 2016", 7 pgs.
"U.S. Appl. No. 14/540,320, Response filed Nov. 8, 2016 to Non Final Office Action dated Apr. 22, 2016", 12 pgs.
"*Arabidopsis thaliana* MYB transcription factor (At5g12870) mRNA, complete cds", XP002714414,accession No. EM_STD:AY519621 Database accession No. AY519621 sequence, (Feb. 7, 2004).
"International Application Serial No. PCT/US2013/027777, International Preliminary Report on Patentability dated Sep. 12, 2014", 11 pgs.
"International Application Serial No. PCT/US2013/027777, International Search Report dated Feb. 11, 2014", 9 pgs.
"International Application Serial No. PCT/US2013/027777, Invitation to Pay Additional Fees and Partial Search Report dated Nov. 20, 2013", 6 pgs.
"International Application Serial No. PCT/US2013/027777, Written Opinion dated Feb. 11, 2014", 9 pgs.
"PCT Application Serial No. PCT/US2013/027777, Corrected International Search Report dated Mar. 24, 2014", 9 pgs.
Kim, et al., "", Plant Mol Biol 84, 577-587.

(Continued)

*Primary Examiner* — Brent T Page
(74) *Attorney, Agent, or Firm* — Schwegman Lundberg & Woessner, P.A.

(57) ABSTRACT

The invention relates to nucleic acids, proteins and methods for modulating the cellulose content of plants.

11 Claims, 18 Drawing Sheets

Specification includes a Sequence Listing.

(56) References Cited

OTHER PUBLICATIONS

Ko, et al,, "Ectopic expression of MYB46 identifies transcriptional regulatory genes involve din secondary wall biosynthesis in *Arabidopsis*", The Plant Journal, vol. 60, No. 4, (Nov. 1, 2009), 649-665.

Ko, Jae-Heung, et al., "MYB46-Mediated Transcriptional Regulation of Secondary Wall Biosynthesis", Molecular Plant, vol. 5, No. 5, (Sep. 2012), 961-963.

Zhong, R., et al., "The MYB46 Transcription Factor Is a Direct Target of SND1 and Regulates Secondary Wall Biosynthesis in *Arabidopsis*", The Plant Cell Online, vol. 19, No. 9, (Sep. 1, 2007), 2776-2792.

"U.S. Appl. No. 14/540,320, Final Office Action dated Jul. 7, 2017", 4 pgs.

"U.S. Appl. No. 14/540,320, Notice of Allowance dated Nov. 9, 2017", 8 pgs.

"U.S. Appl. No. 14/540,320, Response filed Sep. 20, 2017 to Final Office Action dated Jul. 7, 2017", 5 pgs.

"Canadian Application Serial No. 2,865,787, Office Action dated Nov. 8, 2018", 5 pgs.

"Canadian Application Serial No. 2,865,787, Response filed May 8, 2019 to Office Action dated Nov. 8, 2018", 13 pgs.

"International Application Serial No. PCT/US2019/039903, International Search Report dated Sep. 24, 2019", 3 pgs.

"International Application Serial No. PCT/US2019/039903, Written Opinion dated Sep. 24, 2019", 5 pgs.

"Canadian Application Serial No. 2,865,787, Office Action dated Jan. 27, 2020", 3 pgs.

* cited by examiner

COMPETITORS

| | |
|---|---|
| ProCesA4_wt | TCACTCACAGTTTGGTACAACCTCA |
| ProCesA4_m1 | -----------G------------- |
| ProCesA4_m2 | -------------T----------- |
| ProCesA7_wt | CAGAAATTCACCTAATTAAGGACA |
| ProCesA7_m1 | -------------G---------- |
| ProCesA7_m2 | -----------A------------ |
| ProCesA8_wt | CTTATAGAAAGTTGGTGATTGAAAA |
| ProCesA8_m1 | -----------G------------- |
| ProCesA8_m2 | -------------T----------- |

*Fig. 3A*

| Probe | + | + | + | + | - | + | + | + |
|---|---|---|---|---|---|---|---|---|
| MYB112 (50ng) | - | + | + | + | - | + | + | + |
| Competitor | - | - | X10 | X50 | - | - | X10 | X50 |

CesA4 pro 1 (-666 - -294)

CesA4 pro 2 (-294 - -1)

| Probe | + | + | + | + | + | + |
|---|---|---|---|---|---|---|
| WRKY11 (50ng) | - | + | + | - | + | + |
| Competitor | - | - | X50 | - | - | X50 |

CesA4 pro 1 (-666 - -294) CesA4 pro 2 (-294 - -1)

| | | | | | | |
|---|---|---|---|---|---|---|
| Probe | + | + | + | + | + | + |
| ERF6 (50ng) | - | + | + | - | + | + |
| Competitor | - | - | X50 | - | - | X50 |

CesA4 pro 1 (-666 - -294)

CesA4 pro 2 (-294 - -1)

CONTROL OF CELLULOSE BIOSYNTHESIS BY OVEREXPRESSION OF A TRANSCRIPTION FACTOR

This application is a continuation of U.S. patent application Ser. No. 14/381,040, filed Aug. 26, 2014, which is a U.S. National Stage Application under 35 U.S.C. § 371 of PCT/US2013/027777 filed on Feb. 26, 2013, and published on Sep. 6, 2013 as WO 2013/130456 A2, which claims benefit of the filing date of U.S. Provisional Application Ser. No. 61/603,823, filed Feb. 27, 2012, the contents of which are specifically incorporated herein by reference in their entirety.

This invention was made with government support under DE-FC02-07ER64494 awarded by the U.S. Department of Energy. The government has certain rights in the invention.

BACKGROUND OF THE INVENTION

Cellulose is a complex carbohydrate that serves as the basic structural component of plant cell walls. Cellulose accounts for roughly one third of all vegetal matter, making it the most common organic compound on earth. Due to its ubiquitous nature, cellulose and its derivatives are key resources to many industries, such as agricultural, forestry, textile, and paper industries. Recently, there has also been a growing interest in using cellulose to produce value-added compounds such as ethanol or butanol (e.g., for use as biofuels). For industries that rely on plant biomass, for example, the timber and fiber industries, profitability is directly related to the quantity and quality of cellulose harvested from crops. However, there are currently no known methods of genetically controlling the quantity or quality of cellulose synthesized in plant species.

SUMMARY OF THE INVENTION

The invention relates to nucleic acids and proteins useful for regulating expression of plant genes. In some embodiments, the application relates to transgenic plants and compositions derived therefrom that have increased cellulose content, as well as to methods of directly regulating cellulose biosynthesis through genetic manipulation and control. As described herein, several transcription factors directly activate the expression of cellulose synthases. When these transcription factors activate the expression of cellulose synthases the synthases produce increased percentages of cellulose. The nucleic acids, proteins and methods described herein can therefore be used to increase the amount and quality of cellulose in plants. Such regulation of plant cellulose quality and quantity can reduce the costs and improve the efficiencies of industries such as the paper, fiber, and lumber industries.

One aspect of the invention is a plant comprising an isolated nucleic acid encoding a plant transcription factor selected from the group consisting of MYB46, HAM1, HAM2, MYB112, WRKY11, ERF6, or a combination thereof. In some embodiments, the plant transcription factor can, for example, be MYB46. The isolated nucleic acid can have a heterologous promoter segment operably linked to a nucleic segment that encodes the plant transcription factor coding region. Such a heterologous promoter is not the plant transcription factor's natural or native promoter. For example, the heterologous promoter can be a strong promoter, weak promoter, inducible promoter, tissue specific promoter, developmentally regulated promoter, or a combination of such promoters. The isolated nucleic acid can express increased levels of the plant transcription factor in the plant compared to a corresponding transcription factor gene naturally present in a wild type plant of the same species. The plant with the isolated nucleic acid encoding the plant transcription factor can express increased levels of secondary wall cellulose compared to a wild type plant of the same species without the isolated nucleic acid. For example, such a plant can have at least about 2% increased cellulose content compared to a wild type plant of the same species that does not have the isolated nucleic acid. The plant can be a transgenic plant, a genetically modified plant, or a plant selectively bred to comprise the isolated nucleic acid.

Another aspect is a seed that includes an isolated nucleic acid encoding a plant transcription factor selected from the group consisting of MYB46, HAM1, HAM2, MYB112, WRKY11, ERF6, or a combination thereof. The isolated nucleic acid included within the seed can include a heterologous promoter segment operably linked to a nucleic segment that encodes the plant transcription factor coding region. Such a heterologous promoter is not the plant transcription factor's natural promoter, but can be a strong, weak, inducible, tissue specific, developmentally regulated or a combination thereof.

Another aspect is a plant biomass that includes secondary wall cellulose isolated from a plant that includes an isolated nucleic acid encoding a plant transcription factor selected from the group consisting of MYB46, HAM1, HAM2, MYB112, WRKY11, ERF6, or a combination thereof.

A further aspect is a method of increasing cellulose content in a plant cell that includes transforming the plant cell with an isolated nucleic acid that can express a transcription factor selected from the group consisting of MYB46, HAM1, HAM2, MYB112, WRKY11, ERF6, and any combination thereof. The isolated nucleic acid can include a heterologous promoter segment operably linked to a nucleic segment that encodes the plant transcription factor coding region. For example, such a heterologous promoter is not the plant transcription factor's natural promoter. Instead, the heterologous promoter can be a strong promoter, weak promoter, inducible promoter, tissue specific promoter, developmentally regulated promoter, or a combination thereof.

These and other aspects of the invention are further described herein.

DESCRIPTION OF THE DRAWINGS

FIG. 1A shows images of wild type *Arabidopsis* (WT) and transgenic *Arabidopsis* plants. The transgenic *Arabidopsis* plants OX8 and OX9 over-express the MYB46 transcription factor, while the DEX transgenic *Arabidopsis* plant has a dexamethasone-inducible MYB46 transgene. MYB46 expression in the DEX plants was induced by 24 hr of dexamethasone treatment (+DEX). As a control, a DEN plant was mock-treated for 24 hr with 0.05% ethanol and of 0.02% silwet surfactant (−DEX). The plants shown are three-weeks old. As illustrated, the MYB46 over-expression, and DEX(+) plants exhibit a leaf curling phenotype. FIG. 1B is a bar graph illustrating relative MYB46 expression levels. FIG. 1C is a bar graph illustrating relative expression levels of CESA4, CESA7 and CESA8 genes in transgenic OX8 and OX9 *Arabidopsis* plants that over-express the MYB46 transcription factor, as well as the DEX transgenic *Arabidopsis* plant having a dexamethasone-inducible MYB46 transgene. Expression levels were determined by real-time PCR analysis. As shown, MYB46 up-regulates the expression of CESA4, CESA7 and CESA8 genes. Error bars represent the standard deviation of three biological replicates.

FIG. 2A is a diagram of the effector and reporter constructs used in some experiments. MYB46 was fused with a nucleic acid encoding the glucocorticoid receptor (GR) and this MYB46-GR fusion was expressed via the CaMV35S promoter in *Arabidopsis* leaf protoplasts. MYB46 activates the C3H14 promoter via a MYB46-responsive cis-element. To illustrate and evaluate such expression from the C3H14 promoter, the C3H14 promoter was linked to a coding region for β-glucuronidase. The C3H14-β-glucuronidase (C3H14-GUS) construct was used as a reporter gene (positive control) for MYB46 induction of expression. Upon dexamethasone (DEX) treatment, the MYB46-GR chimeric protein becomes functional to activate GUS reporter activity driven by the AtC3H14 promoter. Dexamethasone (DEX) and/or cycloheximide (CHX) were added to the protoplasts to investigate whether the MYB46 can directly regulate the expression of the CESA genes without new protein synthesis. FIG. 2B is a bar graph illustrating relative GUS activity levels in control, DEX, CHX, and DEX+CHX treated plant cells. FIG. 2C illustrates transcription of GUS from control, DEX, and DEX−CHX treated plant cells. Such a analysis shows that DEX-treated MYB46 induced expression from the promoters of C3H14 (FIG. 2C) but GUS activity was inhibited in the presence of 2 μM CHX (FIG. 2B). The expression level of the GUS reporter gene in the protoplasts transfected with no effector construct was used as the Control and the GUS expression from this construct was deemed to be 1. Error bars indicate the standard deviation of three biological replicates. FIG. 2D illustrates results of a real-time PCR analysis showing that the DEX activated MYB46-GR fusion protein directly regulates the expression of CESA4, CESA7 and CESA8 genes in the absence of new protein synthesis. Error bars represent the standard deviation of three biological replicates.

FIGS. 3A and 3B illustrate that MYB46 binds to e promoters of CESA4, CESA7 and CESA8. A GST-MYB46 fusion protein was first incubated with the wild type, double-stranded $^{32}$P-labeled oligodeoxynucleotides with the wild type CESA4, CESA7 and CESA8 promoter sequences shown in FIG. 3A. The GST protein was used as control protein. Unlabeled competitor promoter oligonucleotides were then added the assays to generate the assay mixtures identified FIG. 3B, where the competitors were oligonucleotides with wild type and mutated CESA4, CESA7 and CESA8 promoter sequences shown in FIG. 3A. FIG. 3A shows the CESA4 wild type promoter sequence that included SEQ ID NO:3 (ProCesA4wt) the CESA4 mutated promoter sequences that included SEQ ID NO:4 (ProCesA4m1) and SEQ NO:5 (ProCesA4m2); the CESA7 wild type promoter sequence that included SEQ ID NO:6 (ProCesA7wt); the CESA7 mutated promoter sequences that included SEQ ID NO:7 (ProCesA7m1) and SEQ ID NO: 8 (ProCesA7m2); the CESA8 wild type promoter sequence that included SEQ ID NO:9 (ProCesA8wt); and the CESA8 mutated promoter sequences that included SEQ ID NO:10 (ProCesA8m1) and SEQ ID NO:11 (ProCesA8m2) (dashes indicate no sequence difference). To generate the results shown FIG. 3B, each assay mixture was then subjected to an electrophoretic mobility shift assay (EMSA) by polyacrylamide gel electrophoresis (PAGE). Complexes formed between labeled wild type promoters and the MYB46 protein migrated more slowly than the non-complexed promoter oligonucleotides, and the complexes were detectable if the unlabeled wild type or mutant promoter did not displace the labeled promoter oligonucleotide. FIG. 3B shows that the GST-MYB46 fusion protein binds to CESA4, CESA7 and CESA8 promoter fragments, resulting in retardation of the mobility. The promoter regions used for the DNA probes in each experiment are indicated below the gel images. Competition for the protein-DNA binding was performed using 60× unlabeled probes. The free unbound DNA probes are indicated by the arrow.

FIG. 4A is a diagram of the construct (vector) used for the inducible expression of MY846-GFP. FIG. 4B illustrates the results of a real-time quantitative PCR analysis showing the enrichment of the C3H14 and CESA4, CESA7 and CESA8 promoter sequences after chromatin immunoprecipitation. The values were normalized against that of the control DNA (MYB46 promoter). C3H14 and MYB54 promoters were used as positive and negative control, respectively. Error bars represent the standard deviation of three biological replicates.

FIG. 5A is a bar graph showing the cell wall crystalline cellulose content from 3-weeks old *Arabidopsis* leaves of the indicated plant types. Crystalline cellulose content was increased in the OX8 and OX9 leaves that over-express MYB46, as well as in the MYB46 dexamethasone (−DEX) inducible leaves. FIG. 5B shows images of eight-week old *Arabidopsis* stem sections, where crystalline cellulose was detected by a carbohydrate-binding module (CBM3a) by indirect immunofluorescence. Scale bars=50 μm. The images are labeled with the plant types, with the exception that the image identified as −CBM3a had no CBM3a label. The arrows illustrate that MYB46 over-expression in the OX8 and OX9 plants gives rise to intensive cellulose recognition by CBM3a in the walls of epidermal cells compared with those of wild type (WT).

FIG. 13A is a schematic diagram of the constructs for expression of CESA coding regions driven by either a native (WT) or mutated promoter. The mRNA expression levels from these promoters operably linked to cesa4, cesa7 and cesa8 coding regions are shown in FIG. 13B-D. FIG. 13B shows images of wild type, control and transgenic *Arabidopsis* plants expressing CESA4 from the mutant (M) and native (WC) promoters. FIG. 13C shows images of wild type, control and transgenic *Arabidopsis* plants expressing CESA7 from the mutant (M) and native (WC) promoters. FIG. 13D shows images of wild type, control and transgenic *Arabidopsis* plants expressing CESA8 from the mutant (M) and native (WC) promoters. WT, wild-type (Col-0); VC, vector control (pCB308); M, T-DNA insertion mutants (cesa4, cesa7 and cesa8); WC, genetic complementation of the mutants with native promoter-driven CESA CDS; MC, genetic complementation of the mutants with mutated promoter-driven CESA CDS. Images are a representative of at least 15 plants observed in each wild-type and transgenic lines. The panels below the images of plants show electrophoretically separated RT-PCR products illustrating the expression of the CESAs. Total RNAs (500 ng) was extracted from 5-week-old stems and quantitatively amplified by RT-PCR (28-31 cycles of amplification). Actin was used as a control.

DETAILED DESCRIPTION OF THE INVENTION

Figure 1A:
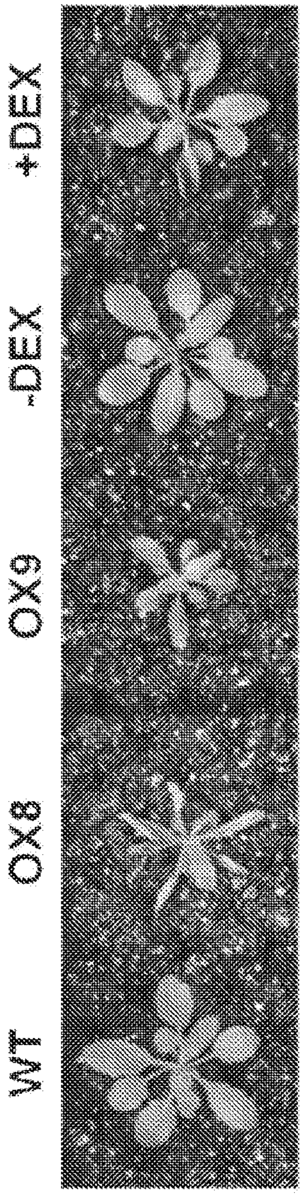
FIG. 1A-1C show images of transgenic plants and bar graphs illustrating phenotypic effects of the transcription factor MYB46 on the expression of the cellulose synthase genes CESA4, CESA7 and CESA8.

The invention relates to nucleic acids, proteins and methods useful for modulating the quality and quantity of cellulose in plants. Plants with such altered cellulose structure/content are useful sources of fiber, lumber and paper. In addition, plants with such altered cellulose structure/content may be hardier and less prone to damage by environmental forces (e.g., wind).

Cellulose

Cellulose is a major component of plant fiber and is composed of crystalline beta-1,4-glucan microfibrils. It is a polysaccharide with the formula $(C_6H_{10}O_5)_n$, where n is an integer of from 100-200,000. Thus, in general, cellulose consists of a linear chain of several hundred to over ten thousand β(1→4) linked D-glucose units. The β(1→4) linkage is distinct from the α(1→4)-glycosidic bonds present in starch, glycogen, and other carbohydrates. Unlike starch, cellulose is a straight chain polymer without coiling and branching. Instead, cellulose has an extended and substantially stiff rod-like conformation, where hydroxyl groups on the glucose from one chain form hydrogen bonds with oxygen molecules on the same or on a neighbor chains, holding the chains firmly together side-by-side and forming microfibrils.

These microfibrils are strong and can resist enzymatic and mechanical degradation. For example, by virtue of its ability to form semicrystalline microfibrils, the tensile strength of cellulose approaches that of some metals. Niklas, Plant Biomechanics: An engineering approach to plant form and function, The University of Chicago Press, p. 607 (1992). However, the bending strength of the culm of normal and brittle-culm mutants of barley has been found to be directly correlated with the concentration of cellulose in the cell wall. Kokubo, et al., (1989), Plant Physiology 91:876-882; Kokubo, et al., (1991) Plant Physiology 97:509-514.

Cellulose Synthases

Cellulose is synthesized by multimeric cellulose synthase (CESA) complexes at the plasma membrane (Somerville, 2006). In plants, two distinct groups of CESAs (each consisting of at least three different isoforms) are preferentially and coordinately expressed during primary and secondary cell wall deposition (Endler and Persson, 2011). The *Arabidopsis* genome contains 10 CESA genes (Pear et al., 1996; Richmond and Somerville, 2001). Recently, a cellulose synthase-interactive protein (CSI1) has been identified as a non-CESA component of the CESA complexes (Gu et al., 2010). Several proteins, such as KORRIGAN, COBRA, KOBITO1, are also known to negatively affect the synthesis of cellulose when mutated or misregulated (Endler and Persson, 2011).

Analyses of various cellulose synthesis mutants has revealed that CESA1, CESA3, CESA6, CESA2, CESA5, and CESA9 (Arioli et al., 1998; Fagard et al., 2000; Scheible et al., 2001; Desprez et al., 2002 and 2007; Persson et al., 2007) are associated with the CESA complexes that are active during primary wall formation.

In contrast, CESA4, CESA7, and CESA8 are necessary for secondary wall cellulose biosynthesis (Turner and Somerville, 1997; Taylor et al., 1999; 2000; 2003; Doblin et al., 2002; Williamson et al., 2002). Unlike the primary wall CESA complex, the three secondary wall CESA subunits appear to be equally important in the function of the complex in xylem vessels and cannot substitute for each other (Gardiner et al., 2003). None of the proteins has been reported to be directly associated with the CESA complex, suggesting that their effects on cellulose synthesis may be indirect. However, as shown herein, the expression of CESA4, CESA7, and CESA8 is directly regulated by binding of the transcription factor MYB46 to cis-acting regulatory motifs that reside in the promoter regions of the CESA4, CESA7 and CESA8 genes. In fact, MYB46 is a key factor that can increase CESA4, CESA7 and CESA8 gene expression.

Control of Cellulose Synthase Expression

Formation of secondary wall requires a coordinated transcriptional activation of the genes involved in the biosynthesis of secondary wall components such as cellulose, hemicellulose and lignin. Recent studies on transcription factors have provided some insight into the complex process of transcriptional regulation of secondary wall biosynthesis (Demura and Ye, 2010; Ko et al. 2007 and 2009; Mitsuda et al, 2005; Mitsuda et al., 2007; Zhong and Ye, 2007; Zhong et al., 2007, 2008, and 2010).

However, while CESAs appear to be the only group of proteins with the ability to synthesize new cellulose molecules, until the present invention little was known about how secondary wall-associated CESA genes were regulated. Prior to the invention described herein, no transcription factor binding, to any CESA promoter had yet been reported.

The data described herein shows that several transcription factors selectively bind to discrete CESA promoters and that CESA production may be a rate limiting factor for cellulose biosynthesis. The transcription factors active in production of CESAs include MYB46, HAM1, HAM2, MYB112, WRKY11, ERF6, as well as other transcription factors with at least 70%, or at least 75%, or at least 80%, or at least 85%, or at least 90%, or at least 95%, or at least 97% sequence identity to any of SEQ ID NO:1, 12, 14, 16, 18, and 20.

MYB46 Transcription Factor

For example, as illustrated herein, over-expression of the MYB46 transcription factor results in ectopic deposition of secondary walls in the cells that are normally parenchymatous, while suppression of MYB46 function reduces secondary wall thickening. Knockout of MYB46 function effectively knocks out CESA4, CESA7 and CESA8 gene expression.

The MYB46 transcription factor sequence is available from the National Center for Biotechnology Information (NCBI) database (see, e.g., the website at ncbi.nlm.nih.gov). For example, a nucleic acid sequence for the MYB46 transcription factor is available as accession number AT5G12870, and reproduced below as SEQ ID NO:1.

```
  1 ATGAGGAAGC CAGAGGTAGC CATTGCAGCT AGTACTCACC
 41 AAGTAAAGAA GATGAAGAAG GGACTTTGGT CTCCTGAGGA
 81 AGACTCAAAG CTGATGCAAT ACATGTTAAG CAATGGACAA
121 GGATGTTGGA GTGATGTTGC GAAAAACGCA GGACTTCAAA
161 GATGTGGCAA AAGCTGCCGT CTTCGTTGGA TCAACTATCT
201 TCGTCCTGAC CTCAAGCGTG GCGCTTTCTC TCCTCAAGAA
241 GAGGATCTCA TCATTCGCTT TCATTCCATC CTCGGCAACA
281 GGTGGTCTCA GATTGCAGCA CGATTGCCTG GTCGGACCGA
```

-continued

```
321 TAACGAGATC AAGAATTTCT GGAACTCAAC AATAAAGAAA
361 AGGCTAAAGA AGATGTCCGA TACCTCCAAC TTAATCAACA
401 ACTCATCCTC ATCACCCAAC ACAGCAAGCG ATTCCTCTTC
441 TAATTCCGCA TCTTCTTTGG ATATTAAAGA CATTATAGGA
481 AGCTTCATGT CCTTACAAGA ACAAGGCTTC GTCAACCCTT
541 CCTTGACCCA CATACAAACC AACAATCCAT TTCCAACGGG
581 AAACATGATC AGCCACCCGT GCAATGACGA TTTTACCCCT
601 TATGTAGATG GTATCTATGG AGTAAACGCA GGGGTACAAG
641 GGGAACTCTA CTTCCCACCT TTGGAATGTG AAGAAGGTGA
681 TTGGTACAAT GCAAATATAA ACAACCACTT AGACGAGTTG
721 AACACTAATG GATCCGGAAA CGCACCTGAG GGTATGAGAC
761 CAGTGGAAGA ATTTTGGGAC CTTGACCAGT TGATGAACAC
801 TGAGGTTCCT TCGTTTTACT TCAACTTCAA ACAAAGCATA
841 TGA
```

The amino acid sequence of the MYB46 polypeptide encoded by the SEQ ID NO:1 nucleic acid is as follows (SEQ ID NO:2).

```
  1 MRKPEVAIAA STHQVKKMKK GLWSPEEDSK LMQYMLSNGQ
 41 GCWSDVAKNA GLQRCGKSCR LRWINYLRPD LHRGAFSPQE
121 EDLIIRFHSI LGNRWSQIAA RLPGRTDNEI KNFWNSTIKK
161 RLKKMSDTSN LINNSSSSPN TASDSSSNSA SSLDIKDIIG
201 SFMSLQEQGF VNPSLTHIQT NNPFPTGNMI SHPCNDDFTP
241 YVDGIYGVNA GVQGELYFPP LECEEGDWYN ANINNHLDEL
281 NTNGSGNAPE GMRPVEEFWD LDQLMNTEVP SFYFNFKQSI
```

Experimental evidence is provided herein showing that MYB46 can directly regulate the expression of three secondary wall cellulose synthases (CESA4, CESA7 and CESA8) in *Arabidopsis* plants. Genome-wide analysis of promoter sequences in *Arabidopsis* by the inventors has revealed that many secondary wall biosynthetic genes, including CESA4, CESA7 and CESA8, have one or more cis-acting regulatory motifs (named 'M46REs') in their promoter regions. As demonstrated herein, MYB46 binds to such cis-acting regulatory motifs and stimulates expression of the secondary wall biosynthetic genes CESA4, CESA7 and CESA8.

One cis-acting regulatory motif that is recognized by MYB46 is naturally located in the promoter region of CESA4, and has the following sequence.

```
TCACTCACAG TTTGGTACAA CCTCA (SEQ ID NO: 3 also
called ProCesA4wt).
```

Two mutant cis-acting CESA4 regulatory motifs with point mutations have been tested and do not bind MYB46. These mutant cis-acting CESA4 regulatory motifs have the following sequences.

TCACTCACAG TGTGGTACAA CCTCA (SEQ ID NO: 4; also called ProCesA4m1).

TCACTCACAG TTTTGTACAA CCTCA (SEQ ID NO: 5; also called ProCesA4m2).

Another cis-acting regulatory motif that is recognized by MYB46 is naturally located in the promoter region of CESA7, and has the following sequence.

CAGAAAATTCACCTAATTAACGACA (SEQ ID NO: 6; also called ProCesA7wt).

Two mutant cis-acting CESA7 regulatory motifs with point imitations have been tested and do not bind MYB46. These mutant cis-acting CESA7 regulatory motifs have the following sequences.

CAGAAAATTCACCTGATTAAGGACA (SEQ ID NO: 7; also called ProCesA7m1).

CAGAAAATTCACATAATTAAGGACA (SEQ ID NO: 8; also called ProCesA7m2).

Another cis-acting regulatory motif that is recognized by MYB46 is naturally located in the promoter region of CESA8, and has the following sequence.

CTTATAGAAAGTTGGTGATTGAAAA (SEQ ID NO: 9; also called ProCesA8wt).

Two mutant cis-acting CESA8 regulatory motifs with point mutations have been tested and do not bind MYB46. These mutant cis-acting CESA8 regulatory motifs have the following sequences.

CTTATAGAAAGGTGGTGATTGAAAA (SEQ ID NO: 10; also called ProCesA8m1).

CTTATAGAAAGTTTGTGATTGAAAA (SEQ ID NO: 11; also called ProCesA8m2).

Nucleic acids encoding these wild type and mutant cis-acting regulatory motifs are therefore useful targets for regulated gene expression.

HAM1 and HAM2 Transcription Factors

As illustrated herein, the HAM1 and HAM2 transcription factors selectively bind to some, but not all cellulose synthase promoters. For example, the HAM1 binds to the regions of the CESA4 promoter, while the HAM2 transcription factor binds to regions of both the CESA4 promoter and the CESA7 promoter.

A nucleotide sequence for the HAM1 transcription factor is shown below (SEQ ID NO:12).

```
   1 ATGGGATCGT CTGCGGATAC AGAGACGGCG ATGATAATCG
  41 CCACACCGGC GTCGAACCAT AATAATCCGG CAACCAACGG
  81 CGGAGATGCG AATCAGAATC ATACTTCTGG TGCGATACTC
```

-continued

```
 121 GCTCTCACGA ATTCAGAATC GGATGCTTCG AAGAAGAGAA
 161 GAATGGGGGT GCTTCCGCTC GAGGTTGGTA CTCGCGTGAT
 201 GTGTCAATGG AGAGACGGAA AATACCATCC GGTGAAGGTT
 241 ATCGAGCGCC GAAAGAATTA TAATGGTGGT CACAATGATT
 231 ACGAGTACTA CGTTCATTAC ACAGAGTTTA ATAGAAGATT
 321 GGATGAATGG ATTAAGCTTG AACAGCTTGA CCTTGATTCA
 361 GTAGAGTGTG CTTTAGATGA AAAAGTTGAA GACAAGGTGA
 401 CTAGCTTGAA GATGACACGA CACCAGAAAC GGAAGATTGA
 441 TGAGACTCAT GTAGAGGGTC ATGAAGAGCT GGATGCTGCC
 481 AGTTTGCGTG AACACGAGGA GTTCACGAAA GTGAAGAACA
 521 TAGCTACGAT TGAGCTTGGG AAGTATGAGA TTGAGACGTG
 561 GTACTTCTCT CCTTTTCCTC CAGAATACAA TGACTGCGTG
 601 AAGCTCTTTT TCTGTGAGTT TTGCCTCAGT TTTATGAAGC
 641 GCAAAGAGCA GCTTCAAAGA CATATGAGGA AATGCGATTT
 681 GAAGCACCCC CCTGGGGATG AAATCTATCG AAGCTCTACT
 721 TTGTCAATGT TTGAGGTGGA TGGCAAGAAG AATAAGGTCT
 761 ATGCACAGAA CCTCTGTTAT CTGGCAAAGT TATTTCTTGA
 801 CCACAAAACT CTTTACTATG ACGTTGATTT GTTCCTGTTC
 841 TATATTCTCT GTGAATGTGA TGATCGTGGA TGCCACATGG
 881 TTGGATACTT TTCAAAGGAA AAACACTCAG AAGAAGCTTA
 921 CAACTTGGCT TGCATCCTTA CACTTCCTCC ATATCAAAGG
 961 AAGGGCTATG GCAAATTCTT AATAGCCTTC TCCTATGAAC
1001 TCTCAAAGAA AGAGGGCAAA GTCGGGACAC CGGAAAGGCC
1041 GCTCTCTGAT CTAGGGTTAG TGAGTTACAG AGGTTACTGG
1081 ACTCGGATTT TATTAGACAT TTTGAAAAAG CACAAGGGAA
1121 ACATATCTAT CAAGGAGCTG AGCGACATGA CAGCGATTAA
1161 AGCAGAAGAT ATATTAAGCA CCCTGCAGAG CTTGGAACTG
1201 ATACAATACA GGAAAGGACA ACACGTAATC TGCGCGGATC
1241 CTAAGGTACT GGACCGACAC TTGAAAGCGG CAGGCCGAGG
1231 TGGTCTTGAT GTGGATGTGA GCAAAATGAT ATGGACTCCT
1321 TACAAAGAGC AGAGCTAA
```

An amino acid sequence for the HAM1 transcription factor encoded by the SEQ ID NO:12 nucleic acid is shown below as SEQ ID NO:13.

```
  1 MGSSADTETA MIIATPASNH NNPATNGGDA NQNHTSGAIL
 41 ALTNSESDAS KKRRMGVLPL EVGTRVMCQW RDGKYHPVKV
 81 IERRKNYNGG HNDYEYYVHY TEFNRRLDEW IKLEQLDLDS
121 VECALDEKVE DKVTSLKMTR HQKRKIDETH VEGHEELDAA
161 SLREHEEFTK VKNIATIELG KYEIETWYFS PFPPEYNDCV
201 KLFFCEFCLS FMKRKEQLQR HMRKCDLKHP PGDEIYRSST
```

-continued

```
241  LSMFEVDGKK NKVYAQNLCY LAKLFLDHKT LYYDVDLFLF

281  YILCECDDRG CHMVGYFSKE KHSEEAYNLA CILTLPPYQR

321  KGYGKFLIAF SYELSKKEGK VGTPERPLSD LGLVSYRGYW

361  TRILLDILKK HKGNISIKEL SDMTAIKAED ILSTLQSLEL

401  IQYRKGQHVI CADPKVLDRH LKAAGRGGLD VDVSKMIWTP

441  YKEQS
```

Experiments described herein demonstrate that the HAM1 transcription factor binds to the CESA4 promoter in the region of nucleotide position −294 to −666 upstream of the coding region of the CESA4 gene.

A nucleotide sequence for the HAM2 transcription factor is shown below (SEQ ID NO:14).

```
   1  ATGGGATCGT CAGCGAATAC AGAAACCAAC GGCAACGCAC

  41  CGCCACCGTC GTCGAATCAA AAGCCTCCGG CTACGAACGG

  81  CGTTGATGGG TCTCATCCTC CTCCTCCTCC TTTAACTCCT

 121  GATCAAGCTA TTATAGAGTC GGATCCGTCG AAGAAGAGGA

 161  AAATGGGGAT GCTTCCTCTA GAAGTGGGTA CTCGTGTGAT

 201  GTGTCGGTGG AGAGACGGGA AACACCATCC GGTGAAAGTA

 241  ATTGAGCGCC GGCGGATACA TAACGGCGGT CAAAATGATT

 281  ACGAGTATTA CGTTCATTAC ACTGAGTTTA ATAGGAGGCT

 321  GGATGAATGG ACTCAGCTGG ACCAACTGGA CCTTGATTCA

 361  GTAGAGTGCG CTGTAGATGA AAAAGTGGAA GACAAGGTAA

 401  CAAGCTTGAA GATGACACGT CACCAGAAGA GGAAGATCGA

 441  TGAGACACAT ATAGAGGGTC ATGAAGAGCT GGATGCAGCA

 481  AGTTTGCGTG AACATGAAGA GTTCACGAAA GIGAAGAACA

 521  TATCAACAAT TGAGCTTGGA AAATATGAGA TTGAGACTTG

 561  GTACTTCTCC CCTTTTCCGC CAGAATACAA TGAGTGTGTG

 601  AAGCTCTTTT TTGTGAGTT TTGCCTGAAC TTCATGAAAC

 641  GCAAAGAGCA GCTTCAAAGG CATATGAGGA AGTGTGACCT

 681  GAAGCACCCA CCTGGTGATG AAATTTACCG AAGTGGTACC

 721  TTGTCAATGT TTGAGGTAGA TGGCAAAAAG AACAAGGTTT

 761  ATGCACAGAA TCTCTGCTAC CTGGCAAAGT TATTTCTTGA

 801  CCACAAAACT CTTTACTACG ATGTTGATTT GTTTCTATTC

 841  TACGTTCTTT GCGAATGTGA TGACCGAGGA TGCCACATGG

 881  TTGGGTACTT TTCAAAGGAG AAGCATTCGG AAGAAGCATA

 921  CAACTTAGCT TGCATTCTAA CCCTGCCTTC AIATCAAAGA

 961  AAAGGCTATG GAAAGTTCTT AATAGCCTTT TCCTATGAAC

1001  TGTCAAAGAA AGAGGGAAAA GTTGGGACAC CGGAAAGACC

1041  CTTGTCGGAT CTAGGCTTAC TAAGCTACAG AGGTTATTGG

1081  ACTCGTGTTC TATTAGAAAT CTTGAAAAAA CATAAGGGAA

1121  ACATTTCTAT CAAGGAGCTG AGCGACGTGA CAGCAATCAA

1161  AGCGGAAGAT ATATTAAGCA CACTTCAGAG CCTAGAACTG
```

-continued

```
1201  ATACAGTACA GGAAAGGACA GCATGTGATC TGTGCGGATC

1241  CAAAGGTTCT GGACCGACAT CTGAAAGCTG CAGGCCGAGG

1281  TGGTCTTGAT GTAGATGCTA GCAAACTGAT TTGGACACCT

1321  TACAAGGAGC AGAGTTAA
```

An amino acid sequence for the HAM2 transcription factor encoded by the SEQ ID NO:14 nucleic acid is shown below as SEQ ID NO:15.

```
  1  MGSSANTETN GNAPPPSSNQ KPPATNGVDG SHPPPPPLTP

 41  DQAIIESDPS KKRKMGMLPL EVGTRVMCRW RDGKHHPVKV

 81  IERRRIHNGG QNDYEYYVHY TEFNRRLDEW TQLDQLDLDS

121  VECAVDEKVE DKVTSLKMTR HQRKIDETH IEGHEELDAA

161  SLREHEEFTK VKNISTIELG KYEIETWYFS PFPPEYNDCV

201  KLFFCEFCLN FMKRKEQLQR HMRKCDLKHP PGDEIYRSGT

241  LSMFEVDGKK NKVYAQNLCY LAKLFLDHKT LYYDVDLFLF

281  YVLCECDDRG CHMVGYFSKF KHSEEAYNLA CILTLPSYQR

321  KGYGKFLIAF SYELSKKEGK VGTPERPLSD LGLLSYRGYW

361  TRVLLEILKK HKGNISIKEL SDVTAIKAED ILSTLQSLEL

401  IQYRKGQHVI CADPKVLDRH LKAAGRGGLD VDASKLIWTP

441  YKDQS
```

Experiments described herein demonstrate that, like the HAM1 transcription factor, the HA M2 transcription factor binds to the CESA4 promoter in the region of nucleotide position −294 to −666 upstream of the coding region of the CESA4 gene. In addition, the HAM2 transcription factor binds to the CESA7 promoter in the region of nucleotide position −1 to −260 upstream of the coding region of the CESA7 gene.

MYB112 Transcription Factor

As illustrated herein, the MYB112 transcription factor selectively binds to some, but not all cellulose synthase promoters. For example, the MYB112 binds selectively only to regions of the CESA4 promoter.

A nucleotide sequence for the MYB112 transcription factor is shown below (SEQ ID NO:16).

```
  1  ATGAATATAA GTAGAACAGA ATTCGCAAAC TGTAAAACCC

 41  TTATAAATCA TAAAGAAGAA GTCGAAGAAG TCGAGAAAAA

 81  GATGGAAATA GAAATAAGGA GAGGTCCATG GACTGTGGAA

121  GAAGACATGA AGCTCGTCAG TTACATTTCT CTTCACGGTG

161  AAGGAAGATG GAACTCCCTC TCTCGTTCTG CTGGACTGAA

201  TAGAACGGGG AAAAGTTGCA GATTGCGGTG GCTAAATTAT

241  CTCCGGCCGG ATATCCGCCG TGGAGACATA TCCCTTCAAG

281  AACAATTTAT CATCCTTGAA CTCCATTCTC GTTGGGGAAA

321  TCGGTGGTCA AAGATTGCTC AACATTTACC GGGAAGAACA

361  GATAACGAGA TAAAGAATTA TTGGAGAACA CGTGTTCAAA

401  AGCATGCAAA ACTTCTAAAA TGTGACGTGA ACAGCAAGCA
```

-continued

```
441  ATTCAAAGAC ACCATCAAAC ATCTCTGGAT GCCTCGTCTC
481  ATCGAGAGAA TCGCCGCCAC TCAAAGTGTC CAATTTACCT
521  CTAACCACTA CTCGCCTGAG AACTCCAGCG TCGCCACCGC
561  CACGTCATCA ACGTCGTCGT CTGAGGCTGT GAGATCGAGT
601  TTCTACGGTG GTGATCAGGT GGAATTTGGA ACGTTGGATC
641  ATATGACAAA TGGTGGTTAT TGGTTCAACG GCGGAGATAC
681  GTTTGAAACT TTGTGTAGTT TTGACGAGCT CAACAAGTGG
721  CTCATACAGT AG
```

An amino acid sequence for the MYB112 transcription factor encoded by the SEQ ID NO:16 nucleic acid is shown below as SEQ ID NO:17.

```
  1  MNISRTEFAN CKTLINHKEE VEEVEKKMEI EIRRGPWTVE
 41  EDMKLVSYIS LHGEGRWNSL SRSAGLNRTG KSCRLRWLNY
 81  LRPDIRRGDI SLQEQFIILE LHSRWGNRWS KIAQHLPGRT
121  DNEIKNYWRT RVQKHAKLLK CDVNSKQFKD TIKHLWMPRL
161  IERIAATQSV QFTSNHYSPE NSSVATATSS TSSSEAVRSS
201  FYGGDQVEFG TLDHMTNGGY WFNGGDTFET LCSFDELNKW
241  LIQ
```

Experiments described herein demonstrate that the MYB112 transcription factor binds to the CESA4 promoter in the region of nucleotide position −294 to −666 upstream of the coding region of the CESA44 gene.

WRKY11 Transcription Factor

As illustrated herein, the WRKY11 transcription factor selectively binds to some, but not all cellulose synthase promoters. For example, the WRKY11 binds selectively only to regions of the CESA4 promoter.

A nucleotide sequence for the WRKY11 transcription factor is shown below (SEQ ID NO:18).

```
  1  ATGGCCGTCG ATCTAATGCG TTTCCCTAAG ATAGATGATC
 41  AAACGGCTAT TCAGGAAGCT GCATCGCAAG GTTTACAAAG
 81  TATGGAACAT CTGATCCGTG TCCTCTCTAA CCGTCCCGAA
121  CAACAACACA ACGTTGACTG CTCCGAGATC ACTGACTTCA
161  CCGTTTCTAA ATTCAAAACC GTCATTTCTC TCCTTAACCG
201  TACTGGTCAC GCTCGGTTCA GACGCGGACC GGTTCACTCC
241  ACTTCCTCTG CCGCATCTCA GAAACTACAG AGTCAGATCG
281  TTAAAAATAC TCAACCTGAG GCTCCGATAG TGAGAACAAC
321  TACGAATCAC CCTCAAATCG TTCCTCCACC GTCTAGTGTA
361  ACACTCGATT TCTCTAAACC AAGCATCTTC GGCACCAAAG
401  CTAAGAGCGC CGAGCTGGAA TTCTCCAAAG AAAACTTCAG
441  TGTTTCTTTA AACTCCTCAT TCATGTCGTC GGCGATAACC
481  GGAGACGGCA GCGTCTCCAA TGGAAAAATC TTCCTTGCTT
521  CTGCTCCGTT GCAGCCTGTT AACTCTTCCG GAAAACCACC
```

-continued

```
561  GTTGGCTGGT CATCCTTACA GAAAGAGATG TCTCGAGCAT
601  GAGCACTCAG AGAGTTTCTC CGGAAAAGTC TCCGGCTCCG
641  CCTACGGAAA GTGCCATTGC AAGAAAAGCA GGAAAAATCG
681  GATGAAGAGA ACCGTGAGAG TACCGGCGAT AAGTGCAAAG
721  ATCGCCGATA TTCCACCGGA CGAATATTCG TGGAGGAAGT
761  ACGGACAAAA ACCGATCAAC GGCTCACCAC ACCCACGTGG
801  TTACTACAAG TGCAGTACAT TCAGAGGATG TCCAGCGAGG
841  AAACACGTGG AACGAGCATT AGATGATCCA GCGATGCTTA
881  TTGTGACATA CGAAGGAGAG CACCGTCATA ACCAATCCGC
921  GATGCAGGAG AATATTTCTT CTTCAGGCAT TAATGATTTA
961  GTGTTTGCCT CGGCTTGA
```

An amino acid sequence for the WRKY11 transcription factor encoded by the SEQ ID NO:18 nucleic acid is shown below as SEQ ID NO:19.

```
  1  MAVDLMRFPK IDDQTAIQEA ASQGLQSMEH LIRVLSNRPE
 41  QQHNVDCSEI TDFTVSKFKT VISLLNRTGH ARFRRGRVHS
 81  TSSAASQKLQ SQIVKNTQPE APIVRTTTNH PQIVPPPSSV
121  TLDFSKPSIF GTKAKSAELE FSKENFSVSL NSSFMSSAIT
161  GDGSVSNGKI FLASAPLQPV NSSGKPPLAG HPYRKRCLEH
201  EHSESFSGKV SGSAYGKCHC KKSRKNRMKR TVRVPAISAK
241  IADIPPDEYS WRKYGQKPIK GSPHPRGYYK CSTFRGCPAR
281  KHVERALDDP AMLIVTYEGE HRHNQSAMQE NISSSGINDL
321  VFASA
```

Experiments described herein demonstrate that the WRKY11 transcription factor binds to the CESA4 promoter in the region of nucleotide position −294 to −666 upstream of the coding region of the CESA4 gene.

ERF6 Transcription Factor

As illustrated herein, the ERF6 transcription factor selectively binds to some, but not all cellulose synthase promoters. For example, the ERF6 binds selectively only to regions of the CESA4 promoter.

A nucleotide sequence for the ERF6 transcription factor is shown below (SEQ ID NO:20).

```
  1  ATGGCTACAC CAAACGAAGT ATCAGCTCTT TTCCTCATCA
 41  AGAAGTATCT CCTCGACGAA TTGTCTCCGT TGCCTACTAC
 81  TGCCACCACC AATCGATGGA TGAACGATTT CACGTCATTT
121  GATCAAACCG GTTTCGAGTT TTCTGAATTT GAAACCAAAC
161  CGGAAATAAT CGATCTCGTC ACTCCCAAAC CGGAGATTTT
201  TGATTTCGAT GTGAAATCTG AAATTCCATC TGAATCGAAC
241  GATTCCTTCA CGTTCCAATC GAATCCTCCT CGCGTTACTG
281  TTCAATCCAA TCGAAAACCG CCGTTGAAGA TCGCACCACC
321  GAACCGAACC AAGTGGATTC AATTCGCAAC CGGAAATCCT
361  AAACCGGAAC TTCCCGTACC GGTTGTAGCA GCAGAGGAGA
```

-continued

```
401  AGAGGCATTA CAGAGGAGTG AGGATGAGGC CGTGGGGGAA

441  ATTCGCGGCG GAGATTCGAG ACCCGACTCG TCGTGGAACT

481  CGTGTTTGGC TCGGGACGTT TGAGACGGCG ATCGAAGCGG

521  CTAGAGCTTA CGACAAAGAA GCGTTTAGAC TACGAGGATC

561  AAAGGCGATT CTGAATTTCC CGCTTGAAGT TGACAAGTGG

601  AATCCACGCG CTGAAGATGG TCGTGGCCTG TACAACAAAC

641  GGAAGAGAGA CGGCGAGGAG GAGGAAGTGA CGGTGGTTGA

681  GAAAGTGCTA AAGACGGAGG AGAGTTACGA CGTTAGCGGC

721  GGCGAGAATG TTGAGTCAGG TTTGACGGCG ATAGATGACT

761  GGGATTTGAC GGAGTTTCTG AGCATGCCGC TTTTATCGCC

801  GTTATCTCCA CACCCACCGT TTGGTTATCC ACAATTGACC

841  GTTGTTTGA
```

An amino acid sequence for the ERF6 transcription factor encoded by the SEQ ID NO:20 nucleic acid is shown below as SEQ ID NO:21.

```
  1  MATPNEVSAL FLIKKYLLDE LSPLPTTATT NRWMNDFTSF

 41  DQTGFEFSEF ETKPEIIDLV TPKPEIFDFD VKSEIPSESN

 81  DSFTFQSNPP RVTVQSNRKP PLKIAPPNRT KWIQFATGNP

121  KPELPVPVVA AEEKRHYRGV RMRPWGKFAA EIRDPTRRGT

161  RVWLGTFETA IEAARAYDKE AFRLRGSKAI LNFPLEVDKW

201  NPRAEDGRGL YNKRKRDGEE EEVTVVEKVL KTEESYDVSG

241  GENVESGLTA IDDWDLTEFL SMPLLSPLSP HPPFGYPQLT

281  VV
```

Experiments described herein demonstrate that the ERF6 transcription factor binds to the CESA4 promoter in the region of nucleotide position −294 to −666 upstream of the coding region of the CESA4 gene.

Therefore, the MYB46, HAM1, HAM2, MYB112, WRKY11, and ERF6 transcription factors bind to and thereby modulate the expression of various cellulose synthases. The following table summarizes to which promoters the transcription factors bind.

| Transcription Factor | Cellulose Synthase Gene |
|---|---|
| MYB46 | CESA4, CESA7, CESA8 |
| HAM1 | CESA4 |
| HAM2 | CESA4, CESA7 |
| MYB112 | CESA4 |
| WRKY11 | CESA4 |
| ERF6 | CESA4 |

As described herein, modification of the expression of cellulose synthases can modify cellulose synthase activity, which can alter cellulose fiber quantity, either by producing more or less fiber in a particular plant species or in a specific organ or tissue of a particular plant. Modification of cellulose synthase activity can increase the value of the fiber to the end-user and may improve the structural integrity of the plant cell wall. In addition, because cellulose is a major cell wall component, inhibition of cellulose synthesis may be lethal. Inhibitors of cellulose synthase expression that target these cis-acting regulatory motifs may therefore serve as herbicides.

Plants Modified to Contain Transcription Factors and/or Promoter Sequences

In order to engineer plants with desired quantities of cellulose, one of skill in the art can introduce transcription factors or nucleic acids encoding transcription factors into the plants. Such transcription factors can bind to the promoter regions of cellulose synthases (e.g., CESA4, CESA7 and CESA8) and stimulate their expression. In some embodiments, the transcription factors can bind to any of SEQ ID NO:3, 6 and/or 9 and stimulate the expression of coding sequences that are operably linked to these SEQ ID NOs. In other embodiments, the transcription factors can bind to any nucleic acid sequence with at least 95% sequence identity to SEQ ID NO:3, 6 and/or 9 and stimulate the expression of coding sequences that are operably linked to nucleic acids with any of these SEQ ID NOs.

In some embodiments, one of skill in the art can inject transcription factors or nucleic acids encoding such transcription factors into young plants, or into selected regions of plants. Alternatively, one of skill in the art can generate genetically-modified plants that contain nucleic acids encoding transcription factors within their somatic and/or germ cells. In addition, those of skill in the art can use any of the promoters with any the SEQ ID NO:3, 6, and/or 9 promoter sequences with the transcription factors to drive the expression of other coding regions of interest, for example, by genetically modifying a plant to contain a promoter nucleic acid upstream of the coding region of interest and an expression cassette that can express the transcription factor. Such genetic modification can be accomplished by procedures available in the art. For example, one of skill in the art can prepare an expression cassette or expression vector that can express one or more encoded transcription factors while the promoter is operably linked to a coding region of interest in a separate expression cassette. Plant cells can be transformed by the expression cassettes or expression vector, and whole plants (and their seeds) can be generated from the plant cells that were successfully transformed with the promoter and/or transcription factor nucleic acids. Some procedures for making such genetically modified plants and their seeds are described below.

Plants modified to contain the isolated transcription factors described herein (e.g., expressed from a heterologous promoter and/or from a transgene and/or from an expression cassette) can have increased cellulose content relative to a wild type plant of the same species that does not have such an isolated transcription factor. For example, plants expressing one of the transcription factors described herein from an isolated nucleic acid can have at least about 2%, or at least about 4%, or at least about 5%, or at least about 7%, or at least about 10%, or at least about 12%, or at least about 13%, or at least about 15%, or at least about 17%, or at least about 20%, or at least about 22%, or at least about 25%, or at least about 30% increased cellulose content compared to a wild type plant of the same species (without the added isolated transcription factor).

Promoters: The transcription factor nucleic acids of the invention can be operably linked to a promoter, which provides for expression of mRNA from the transcription factor nucleic acids. The promoter is typically a promoter functional in plants and/or seeds, and can be a promoter functional during plant growth and development. A transcription factor nucleic acid is operably linked to the promoter when it is located downstream from the promoter, to thereby form an expression cassette.

Similarly, a nucleic acid segment encoding any of the cellulose synthase promoters described herein (e.g., any segment that includes SEQ ID NO:3-11, 65-71, or any segment that includes a sequence with at least 95% sequence identity to SEQ ID NO:3-11, 65-71) can be operably linked to a selected coding region of interest, for example, by inserting the promoter nucleic acid segment upstream of a coding region nucleic acid.

Promoters regulate gene expression. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences can also contain regulatory sequences such as enhancer sequences that can influence the level of gene expression. Some isolated promoter sequences can provide for gene expression of heterologous DNAs, that is a DNA different from the native or homologous DNA.

Promoter sequences can be strong or weak, or inducible. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. For example, a bacterial promoter such as the $P_{tac}$ promoter can be induced to vary levels of gene expression depending on the level of isothiopropylgalactoside added to the transformed cells.

Promoters can also provide for tissue specific or developmental regulation. In some embodiments, an isolated promoter sequence that is a strong promoter for heterologous DNAs is advantageous because it provides for a sufficient level of gene expression for easy detection and selection of transformed cells and provides for a high level of gene expression when desired.

In some embodiments, heterologous promoters can be operably linked to one or more cellulose synthase coding sequence segment (e.g., CESA4, CESA7 and/or CESA8), where the heterologous promoter is a strong promoter, weak promoter, inducible promoter, tissue specific promoter, developmentally regulated promoter, or some combination thereof.

The selected promoter-cellulose synthase construct can be placed in an expression cassette or expression vector.

Expression cassettes for the transcription factor can include, but are not limited to, a plant promoter with a sequence such as any of the SEQ ID NO:3-11, 65-71 (or a combination thereof). Expression cassettes for the transcription factor can also include, but are not limited to, a plant promoter such as the CaMV 35S promoter (Odell et al., *Nature*. 313: 810-812 (1985)), or others such as CaMV 19S (Lawton et al., *Plant Molecular Biology*. 9: 315-324 (1987)), nos (Ebert et al., *Proc. Natl. Acad. Sci. USA*. 84: 5745-5749 (1987)), Adhl (Walker et al., *Proc. Natl. Acad. Sci. USA*. 84: 6624-6628 (1987)), sucrose synthase (Yang et al., *Proc. Natl. Acad. Sci. USA*. 87: 4144-4148 (1990)), α-tubulin, ubiquitin, actin (Wang et al., *Mol. Cell. Biol*. 12: 3399 (1992)), cab (Sullivan et al., *Mol. Gen. Genet*. 215: 431 (1989)), PEPCase (Hudspeth et at, *Plant Molecular Biology*. 12: 579-589 (1989)) or those associated with the R gene complex (Chandler et al., *The Plant Cell*. 1: 1175-1183 (1989)). Further suitable promoters include the poplar xylem-specific secondary cell wall specific cellulose synthase 8 promoter, cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene (Coruzzi et al., *EMBO J*. 3: 1671 (1971)) and the actin promoter from rice (McElroy et al., *The Plant Cell*. 2: 163-171 (1990)). Seed specific promoters, such as the phaseolin promoter from beans, may also be used (Sengupta-Gopalan, *Proc. Natl. Acad. Sci. USA*. 83: 3320-3324 (1985). Other promoters useful in the practice of the invention are known to those of skill in the art.

The novel tissue specific promoter sequences described here, as well as other promoter sequences, can therefore be employed for the expression of the transcription factor(s). cDNA clones from a particular tissue can be isolated and those clones that are expressed specifically in a tissue of interest are identified, for example, using Northern blotting, quantitative PCR and other available methods. In some embodiments, the gene isolated is not present in a high copy number, but is relatively abundant in specific tissues. The promoter and control elements of corresponding genomic clones can then be identified, isolated and utilized using techniques well known to those of skill in the art.

A transcription factor nucleic acid can be combined with a selected promoter by standard methods to yield an expression cassette, for example, as described in Sambrook et al. (Molecular Cloning: A Laboratory Manual. Second Edition (Cold Spring Harbor, N.Y.: Cold Spring Harbor Press (1989); Molecular Cloning: A Laboratory Manual. Third Edition (Cold Spring Harbor, N.Y.: Cold Spring Harbor Press (2000)). Briefly, a plasmid containing a promoter such as the 35S CaMV promoter can be constructed as described in Jefferson (*Plant Molecular Biology Reporter* 5: 387-405 (1987)) or obtained from Clontech Lab in Palo Alto, Calif. (e.g., pBI121 or pBI221). Typically, these plasmids are constructed to have multiple cloning sites having specificity for different restriction enzymes downstream from the promoter. The transcription factor nucleic acids can be subcloned downstream from the promoter using restriction enzymes and positioned to ensure that the transcription factor DNA is inserted in proper orientation with respect to the promoter so that the DNA can be expressed. Once the transcription factor nucleic acid is operably linked to a promoter, the expression cassette so formed can be subcloned into a plasmid or other vector (e.g., an expression vector).

In some embodiments, a cDNA clone encoding a transcription factor protein is isolated from *Arabidopsis*. In other embodiments, cDNA clones from other species (that encode a transcription factor protein) are isolated from selected plant tissues, or a nucleic acid encoding a mutant or modified transcription factor protein is prepared by available methods or as described herein. For example, the nucleic acid encoding a mutant or modified transcription factor protein can be any nucleic acid with a coding region that hybridizes to SEQ ID NO:1, 12, 14, 16, 18, or 20, and that can promote expression of a cellulose synthase enzyme. Using restriction endonucleases, the entire coding sequence for the transcription factor is subcloned downstream of the promoter in a 5' to 3' sense orientation. The transcription factor protein can be operably linked to a promoter sequence that is not a nucleic acid segment with a sequence that includes SEQ ID NO:3-11, 65-71, or a combination thereof. In other words, while expression of the transcription factor protein can be self-regulating (e.g., driven by binding of the transcription factor protein to its own promoter), the expression of the transcription factor protein can also be controlled by a heterologous promoter that is a strong, weak, inducible, tissue specific, developmentally regulated or some combination thereof (and that does not include SEQ ID NO:3-11, 65-71, or a combination thereof).

Targeting Sequences:

Additionally, expression cassettes can be constructed and employed to target the transcription factors or other polypeptides of interest to intracellular compartments within plant cells, or to target the transcription factors or polypeptides of interest for extracellular secretion.

In general, transcription factors bind to plant chromosomal DNA within the nucleus. Therefore, the transcription factor is preferably targeted to the nucleus and not directed to other plant organelles or the extracellular environment. However, there may be instances where is it desirable to secrete or sequester the transcription factor within organelles or storage vesicles (e.g., to facilitate isolation and/or purification of the transcription factor protein). Similarly, polypeptides of interest can be encoded within expression cassettes containing one of the cellulose synthase promoters described herein, and it may be desirable to target those polypeptides to various intracellular compartments or to the extracellular environment. Therefore, the invention contemplates targeting the transcription factor(s) as well as polypeptides of interest to various intracellular and extracellular locations.

A nuclear localization signal or sequence is an amino acid sequences that 'tags' a protein for import into the cell nucleus by nuclear transport. Transcription factors may naturally have such a nuclear localization signal or sequence. Alternatively, a nuclear localization signal or sequence can be operably linked to the transcription factor sequence. Transit peptides act by facilitating the transport of proteins through intracellular membranes, e.g., vacuole, vesicle, plastid and mitochondrial membranes, whereas signal peptides direct proteins through the extracellular membrane. Polypeptides of interest can be operably linked to nuclear localization signals/sequences, to transit peptides or to signal peptides.

Targeting to selected intracellular regions can generally be achieved by joining a DNA sequence encoding a nuclear localization sequence, or a transit peptide or a signal peptide sequence to the coding sequence of the transcription factor or the polypeptide of interest. The resultant nuclear localization sequence (or transit, or signal, peptide) will transport the protein to a particular intracellular (or extracellular) destination. Such sequences (nuclear localization sequences, transit peptides or signal peptides) may be posttranslationally removed by cellular enzymes. By facilitating transport of the protein into compartments inside or outside the cell, these sequences can increase the accumulation of a particular gene product in a particular location.

3' Sequences:

The expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. For example, 3' elements that can be used include those derived from the nopaline synthase gene of *Agrobacterium tumefaciens* (Bevan et al., *Nucleic Acid Research.* 11:369-385 (1983)), or the terminator sequences for the T7 transcript from the octopine synthase gene of *Agrobacterium tumefaciens*, and/or the 3' end of the protease inhibitor I or II genes from potato or tomato. Other 3' elements known to those of skill in the art can also be employed. These 3' nontranslated regulatory sequences can be obtained as described in An (*Methods in Enzymology,* 153:292 (1987)). Many such 3' nontranslated regulatory sequences are already present in plasmids available from commercial sources such as Clontech, Palo Alto, Calif. The 3' nontranslated regulatory sequences can be operably linked to the 3' terminus of the transcription factor or other polypeptide nucleic acids by standard methods.

Selectable and Screenable Marker Sequences: In order to improve identification of transformants, a selectable or screenable marker gene can be employed with the expressible transcription factor or other polypeptide nucleic acids. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for the marker by chemical means, i.e., through the use of a selective agent (e.g., a herbicide, antibiotic, or the like), or whether marker is simply a trait that one can identify through observation or testing, i.e., by 'screening' (e.g., the R-locus trait). Many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a polypeptide that becomes sequestered in the cell wall, where the polypeptide includes a unique epitope may be advantageous. Such a secreted antigen marker can employ an epitope sequence that would provide low background in plant tissue, a promoter-leader sequence that imparts efficient expression and targeting across the plasma membrane, and can produce protein that is bound in the cell wall and yet is accessible to antibodies. A normally secreted wall protein modified to include a unique epitope would satisfy such requirements.

Examples of marker proteins suitable for modification in this manner include extensin or hydroxyproline rich glycoprotein (HPRG). For example, the maize IIPRG (Stiefel et al., *The Plant Cell.* 2: 785-793 (1990)) is well characterized in terms of molecular biology, expression, and protein structure and therefore can readily be employed. However, any one of a variety of extensins and/or glycine-rich wall proteins (Keller et al., *EMBO J.* 8: 1309-1314 (1989)) could be modified by the addition of an antigenic site to create a screenable marker.

Elements of the present disclosure are exemplified in detail through the use of particular marker genes. However in light of this disclosure, numerous other possible selectable and/or screenable marker genes will be apparent to those of skill in the art in addition to the one set forth herein below. Therefore, it will be understood that the following discussion is exemplary rather than exhaustive. In light of the techniques disclosed herein and the general recombinant techniques that are known in the art, the present invention readily allows the introduction of any gene, including marker genes, into a recipient cell to generate a transformed plant cell, e.g., a monocot cell or dicot cell.

Possible selectable markers for use in connection with the present invention include, but are not limited to, a neo gene (Potrykus et al., *Mol. Gen. Genet.* 199: 183-188 (1985)) which codes for kanamycin resistance and can be selected for using kanamycin, G418, and the like; a bar gene which codes for bialaphos resistance; a gene which encodes an altered EPSP synthase protein (Hinchee et al., *Bio/Technology.* 6: 915-922 (1988)) thus conferring glyphosate resistance; a nitrilase gene such as barn front *Klebsiella ozaenae* which confers resistance to bromoxynil (Stalker et at, *Science.* 242: 419-423 (1988)); a mutant acetolactate synthase gene (ALS) which confers resistance to imidazolinone, sulfonylurea or other ALS-inhibiting chemicals (European Patent Application 154,204 (1985)); a methotrexate-resistant DHFR gene (Thillet et al., *J. Biol. Chem.* 263: 12500-12508 (1988)); a dalapon dehalogenase gene that confers resistance to the herbicide dalapon; or a mutated anthranilate synthase gene that confers resistance to 5-methyl tryptophane. Where a mutant EPSP synthase gene is employed, additional benefit may be realized through the incorporation of a suitable chloroplast transit peptide, CTP (European Patent Application 0 218 571 (1987)).

Another selectable marker gene capable of being used in for selection of transformants is the gene that encode the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.* 205: 42-50 (1986); Twell et al., *Plant Physiol.* 91: 1270-1274 (1989)) causing rapid accumulation of ammonia and cell death. The success in using this selective system in conjunction with monocots was surprising because of the major difficulties that have been reported in transformation of cereals (Potrykus, *Trends Biotech.* 7:269-273 (1989)).

Screenable markers that may be employed include, but are not limited to, a β-glucuronidase or uidA gene (GUS) that encodes an enzyme for which various chromogenic substrates are known; an R-locus gene, which encodes a product that regulates the production of anthocyanin pigments (red color) in plant tissues (Dellaporta et al., In: *Chromosome Structure and Function: Impact of New Concepts,* $18^{th}$ Stadler Genetics Symposium, J. P. Gustafson and R. Appels, eds. (New York: Plenum Press) pp. 263-282 (1988)); a β-lactamase gene (Sutcliffe, *Proc. Natl. Acad. Sci. USA.* 75: 3737-3741 (1978)), which encodes an enzyme for which various chromogenic substrates are known (e.g., PADAC, a chromogenic cephalosporin); a xylE gene (Zukowsky et al., *Proc. Natl. Acad. Sci. USA.* 80:1101 (1983)) which encodes a catechol dioxygenase that can convert chromogenic catechols; an α-amylase gene (Ikuta et al., *Bio/technology* 8: 241-242 (1990)); a tyrosinase gene (Katz et al., *J. Gen. Microbiol.* 129: 2703-2714 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science.* 234: 856-859, 1986), which allows for bioluminescence detection; or an aequorin gene (Prasher et al., *Biochem. Biophys. Res. Comm.* 126: 1259-1268 (1985)), which may be employed in calcium-sensitive bioluminescence detection, or a green or yellow fluorescent protein gene (Niedz et al., *Plant Cell Reports.* 14: 403 (1995).

For example, genes from the maize R gene complex can be used as screenable markers. The R gene complex in maize encodes a protein that acts to regulate the production of anthocyanin pigments in most seed and plant tissue. Maize strains can have one, or as many as four, R alleles that combine to regulate pigmentation in a developmental and tissue specific manner. A gene froth the R gene complex does not harm the transformed cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 that contains the rg-Stadler allele and TR112, a K55 derivative that is r-g, b, P1. Alternatively any genotype of maize can be utilized if the C1 and R alleles are introduced together.

The R gene regulatory regions may be employed in chimeric constructs in order to provide mechanisms for controlling the expression of chimeric genes. More diversity of phenotypic expression is known at the R locus than at any other locus (Coe et al., in *Corn and Corn Improvement*, eds. Sprague, G. F. & Dudley, J. W. (Am. Soc. Agron., Madison, Wis.), pp. 81-258 (1988)). It is contemplated that regulatory regions obtained from regions 5' to the structural R gene can be useful in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, one that can be used is Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for population screening for bioluminescence, such as on tissue culture plates, or even for whole plant screening.

Other Optional Sequences:

An expression cassette of the invention can also further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes (e.g., antibiotic or herbicide resistance), unique multiple cloning sites providing for multiple sites to insert DNA sequences or genes encoded in the expression cassette and sequences that enhance transformation of prokaryotic and eukaryotic, cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An (*Methods in Enzymology,* 153: 292 (1987)) and is available from Dr. An. This binary Ti vector can be replicated in prokaryotic bacteria such as *E. coli* and *Agrobacterium*. The *Agrobacterium* plasmid vectors can be used to transfer the expression cassette to dicot plant cells, and under certain conditions to monocot cells, such as rice cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform dicot plant cells.

In Vitro Screening of Expression Cassettes:

Once the expression cassette is constructed and subcloned into a suitable plasmid, it can be screened for the ability to express the transcription factor or another polypeptide of interest. For example, an expression cassette encoding a transcription factor can be screened to ascertain whether it can promote expression of a cellulose synthase by methods described herein or other available methods for detecting cellulose. An expression cassette encoding a other polypeptides of interest (with a promoter that includes a segment with a sequence such as any of SEQ ID NOs: 3-11, 65-71, or a combination thereof) can be screened to ascertain whether it can promote expression of the polypeptide, for example, by immunological detection of the polypeptide of interest, by detection of the activity of the polypeptide, by hybridization or PCR detection of transcripts encoding the polypeptide, or by other procedures available to those of skill in the art.

DNA Delivery of the DNA Molecules into Host Cells:

Nucleic acids encoding a transcription factor or another polypeptide can be introduced into host cells by a variety of methods. For example, a preselected cDNA encoding the selected transcription factor or other polypeptide can be introduced into a recipient cell to create a transformed cell by available procedures. The frequency of occurrence of cells taking up exogenous (foreign) DNA may be low. Moreover, it is most likely that not all recipient cells receiving DNA segments or sequences will result in a transformed cell wherein the DNA is stably integrated into the plant genome and/or expressed. Some may show only initial and transient gene expression. However, certain cells from virtually any dicot or monocot species may be stably transformed, and these cells can be regenerated into transgenic plants, through the application of the techniques disclosed herein.

Another aspect of the invention is an isolated plant or plant cell that has one of the transcription factors or promoters described herein introduced into the plant or cell, e.g., as a nucleic acid encoding the transcription factor or promoter. The isolated plant or plant cell can also have any of the isolated transcription factors described herein as a protein product. The plant can be a monocotyledon or a dicotyledon. Another aspect of the invention includes plant cells (e.g., embryonic cells or other cell lines) that can regenerate fertile transgenic plants and/or seeds. The cells can be derived from either monocotyledons or dicotyledons. Suitable examples of plant species include wheat, rice, *Arabidopsis*, tobacco, maize, soybean, poplar, and the like. In some embodiments, the plant or cell is a monocotyledon plant or cell. For example, the plant or cell can be a maize plant or cell. The cell(s) may be in a suspension cell culture or may be in an intact plant part, such as an immature embryo, or in a specialized plant tissue, such as callus, such as Type I or Type II callus.

Plants or plant cells that can have one of the transcription factors or promoters described herein introduced therein include but are not limited to grass species, oil and/or starch plants (canola, potatoes, lupins, sunflower and cottonseed), forage plants (alfalfa, clover and fescue), grains (maize, wheat, barley, oats, rice, sorghum, millet and rye), grasses (switchgrass, prairie grass, wheat grass, sudangrass, sorghum, straw-producing plants), softwood, hardwood and other woody plants (e.g., those used for paper production such as poplar species, pine species, and eucalyptus). In some embodiments the plant is a gymnosperm. Examples of plants useful for pulp and paper production include most pine species such as loblolly pine, Jack pine, Southern pine, Radiata pine, spruce, Douglas fir and others. Hardwoods that can be modified as described herein include aspen, poplar, eucalyptus, and others. Plants useful for making biofuels and ethanol include corn, grasses (e.g., miscanthus, switchgrass, and the like), as well as trees such as poplar, aspen, willow, and the like. Plants useful for generating dairy forage include legumes such as alfalfa, as well as forage grasses such as bromegrass, and bluestem.

Transformation of the cells of the plant tissue source can be conducted by any one of a number of methods known to those of skill in the art. Examples are: Transformation by direct DNA transfer into plant cells by electroporation (U.S. Pat. No. 5,384,253 and U.S. Pat. No. 5,472,869, Dekeyser et al., *The Plant Cell.* 2: 591-602 (1990)); direct DNA transfer to plant cells by PEG precipitation (Hayashimoto et al., *Plant Physiol.* 93: 857-863 (1990)); direct DNA transfer to plant cells by microprojectile bombardment (McCabe et al., *Bio/Technology.* 6: 923-926 (1988); Gordon-Kamm et al., *The Plant Cell.* 2: 603-618 (1990); U.S. Pat. Nos. 5,489,520; 5,538,877; and 5,538,880) and DNA transfer to plant cells via infection with *Agrobacterium*. Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack functions for disease induction.

One method for dicot transformation, for example, involves infection of plant cells with *Agrobacterium tumefaciens* using the leaf-disk protocol (Horsch et al., *Science* 227: 1229-1231 (1985). Monocots such as *Zea mays* can be transformed via microprojectile bombardment of embryogenic callus tissue or immature embryos, or by electroporation following partial enzymatic degradation of the cell wall with a pectinase-containing enzyme (U.S. Pat. Nos. 5,384,253; and 5,472,869). For example, embryogenic cell lines derived from immature *Zea mays* embryos can be transformed by accelerated particle treatment as described by Gordon-Kamm et al. (*The Plant Cell.* 2: 603-618 (1990)) or U.S. Pat. Nos. 5,489,520; 5,538,877 and 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing *Agrobacterium tumefaciens* have been described by Hiei et at (European Patent 0 604 662, 1994) and Saito et al. (European Patent 0 672 752, 1995).

Methods such as microprojectile bombardment or electroporation are carried out with "naked" DNA where the expression cassette may be simply carried on any *E. coli*-derived plasmid cloning vector. In the case of viral vectors, it is desirable that the vectors retain replication functions, but not have functions for disease induction.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are preferred *Zea mays* tissue sources. Selection of tissue sources for transformation of monocots is described in detail in U.S. application Ser. No. 08/112,245 and PCT publication WO 95/06128.

The transformation is carried out under conditions directed to the plant tissue of choice. The plant cells or tissue are exposed to the DNA or RNA carrying the transcription factor nucleic acids for an effective period of time. This may range from a less than one second pulse of electricity for electroporation to a 2-3 day co-cultivation in the presence of plasmid-bearing *Agrobacterium* cells. Buffers and media used will also vary with the plant tissue source and transformation protocol. Many transformation protocols employ a feeder layer of suspended culture cells (tobacco or Black Mexican Sweet corn, for example) on the surface of solid media plates, separated by a sterile filter paper disk from the plant cells or tissues being transformed.

Electroporation:

Where one wishes to introduce DNA by means of electroporation, it is contemplated that the method of Krzyzek et al. (U.S. Pat. No. 5,384,253) may be advantageous. In this method, certain cell wall-degrading enzymes, such as pectin-degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

Microprojectile Bombardment:

A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. For example, non-embryogenic Black Mexican Sweet maize cells can be bombarded with intact cells of the bacteria *E. coli* or *Agrobacterium tumefaciens* containing plasmids with either the β-glucuronidase or bar gene engineered for expression in maize. Bacteria can be inactivated by ethanol dehydration prior to bombardment. A low level of transient expression of the β-glucuronidase gene may be observed 24-48 hours following DNA delivery. In addition, stable transformants containing the bar gene can be recovered following bombardment with either *E. coli* or *Agrobacterium tumefaciens* cells. It is contemplated that particles may contain DNA rather than be coated with DNA. Hence it is proposed that particles may increase the level of DNA delivery but are not, in and of themselves, necessary to introduce DNA into plant cells.

An advantage of microprojectile bombardment, in addition to it being an effective means of reproducibly stably transforming monocots, is that the isolation of protoplasts (Christou et al., PNAS. 84: 3962-3966 (1987)), the formation of partially degraded cells, or the susceptibility to *Agrobacterium* infection is not required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon-Kamm et al., *The Plant Cell.* 2:603-618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of such techniques one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

After effecting delivery of a transcription factor nucleic acid (or other nucleic acid encoding a desirable polypeptide) to recipient cells by any of the methods discussed above, the transformed cells can be identified for further culturing and plant regeneration. As mentioned above, in order to improve the ability to identify transformants, one may employ a selectable or screenable marker gene as, or in addition to, the expressible transcription factor nucleic acids. In this case, one would then generally assay the potentially transformed cell population by exposing the cells to a selective agent or agents, or one would screen the cells for the desired marker gene trait.

Selection:

An exemplary embodiment of methods for identifying transformed cells involves exposing the bombarded cultures to a selective agent, such as a metabolic inhibitor, an antibiotic, herbicide or the like. Cells that have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about. 0.1-50 mg/l bialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells front colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In an illustrative embodiment embryogenic Type II callus of *Zea mays* L. can be selected with sublethal levels of bialaphos. Slowly growing tissue was subsequently screened for expression of the luciferase gene and transformants can be identified.

Regeneration and Seed Production:

Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soil-less plant growth mix, and hardened, e.g., in an environmentally controlled chamber at about 85% relative humidity, about 600 ppm $CO_2$, and at about 25-250 microeinsteins/sec·$m^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that are known to express the trait. In some embodiments, the regenerated plants are self pollinated. In addition, pollen obtained from the regenerated plants can be crossed to seed grown plants of agronomically important inbred lines. In some cases, pollen front plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the transcription factor nucleic acids into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced transcription factor or other promoter-polypeptide encoding nucleic acids, the plant is self-pollinated at least once in order to produce a homozygous backcross converted inbred containing the transcription factor or other promoter-polypeptide nucleic acids. Progeny of these plants are true breeding.

Alternatively, seed from transformed monocot plants regenerated from transformed tissue cultures is grown in the field and self-pollinated to generate true breeding plants.

Seed from the fertile transgenic plants can then be evaluated for the presence and/or expression of the transcription factor or other polypeptide nucleic acids (or the encoded transcription factor or other polypeptide). Transgenic plant and/or seed tissue can be analyzed for transcription factor expression using standard methods such as SDS polyacrylamide gel electrophoresis, liquid chromatography (e.g., HPLC) or other means of detecting a product of transcription factor activity (e.g., increased cellulose or heightened expression of a cellulose synthase) or a product of the polypeptide of interest.

Once a transgenic seed expressing the transcription factor or other polypeptide sequence is identified, the seed can be used to develop true breeding plants. The true breeding plants are used to develop a line of plants that express the transcription factor, contain one of the cellulose synthase promoters described herein and/or contain a nucleic acid encoding such a promoter linked to a polypeptide of interest, while still maintaining other desirable functional agronomic traits. Adding the trait of increased transcription factor or other polypeptide expression to the plant can be accomplished by back-crossing with this trait with plants that do not exhibit this trait and by studying the pattern of inheritance in segregating generations. Those plants expressing the target trait in a dominant fashion are preferably selected. Back-crossing is carried out by crossing the original fertile transgenic plants with a plant from an inbred line exhibiting desirable functional agronomic characteristics while not necessarily expressing the trait of expression of a transcription factor and/or other desired polypeptide in the plant. The resulting progeny are then crossed back to the parent that expresses the trait. The progeny from this cross will also segregate so that some of the progeny carry the trait and some do not. This back-crossing is repeated until an inbred line with the desirable functional agronomic trails, and with expression of the desired trait within the plant. Such expression of the increased expression of the transcription factor or other polypeptide in plant can be expressed in a dominant fashion.

Subsequent to back-crossing, the new transgenic plants can be evaluated for expression of the transcription factor or other polypeptide. For example, when the transcription factor is expressed the weight percent of cellulose within the plant or within selected tissues of the plant is increased. Detection of increased cellulose can be done, for example, by staining plant tissues for cellulose or by observing whether the tensile strength of plant fibers is increased or otherwise modulated relative to a plant that does not contain the exogenously added transcription factor. The new transgenic plants can also be evaluated for a battery of functional agronomic characteristics such as lodging, kernel hardness, yield, resistance to disease and insect pests, drought resistance, and/or herbicide resistance.

Plants that may be improved by these methods include but are not limited to fiber-containing plants, trees, flax, grains (maize, wheat, barley, oats, rice, sorghum, millet and rye), grasses (switchgrass, prairie grass, wheat grass, sudangrass, sorghum, straw-producing plants), softwood, hardwood and other woody plants (e.g., those used for paper production such as poplar species, pine species, and eucalyptus), oil and/or starch plants (canola, potatoes, lupins, sunflower and cottonseed), and forage plants (alfalfa, clover and fescue). In some embodiments the plant is a gymnosperm Examples of plants useful for pulp and paper production include most pine species such as loblolly pine, Jack pine, Southern pine, Radiata pine, spruce, Douglas fir and others. Hardwoods that can be modified as described herein include aspen, poplar, eucalyptus, and others. Plants useful for making biofuels and ethanol include corn, grasses (e.g., miscanthus, switchgrass, and the like), as well as trees such as poplar, aspen, willow, and the like. Plants useful for generating dairy forage include legumes such as alfalfa, as well as forage grasses such as bromegrass, and bluestem.

Determination of Stably Transformed Plant Tissues:

To confirm the presence of the transcription factor or other promoter-polypeptide-encoding nucleic acids in the regenerating plants, or in seeds or progeny derived from the regenerated plant, a variety of assays may be performed. Such assays include, for example, molecular biological assays available to those of skill in the art, such as Southern and Northern blotting, and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from introduced transcription factor nucleic acids. PCR also be used to reverse transcribe RNA into DNA, using enzymes such as reverse transcriptase, and then this DNA can be amplified through the use of conventional PCR techniques. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and also demonstrate the presence or absence of an RNA species.

While Southern blotting and PCR may be used to detect the transcription factor nucleic acid in question, they do not provide information as to whether the preselected DNA segment is being expressed. Expression may be evaluated by specifically identifying the protein products of the introduced transcription factor nucleic acids or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the transcription factor or other polypeptide such as evaluation by amino acid sequencing following purification. The Examples of this application also provide assay procedures for detecting and quantifying transcription factor or other polypeptide or enzyme activities. Other procedures may be additionally used.

The expression of a gene product can also be determined by evaluating the phenotypic results of its expression. These assays also may take many forms including but not limited to analyzing changes in the chemical composition, morphology, or physiological properties of the plant.

Definitions

As used herein, "isolated" means a nucleic acid or polypeptide has been removed from its natural or native cell. Thus, the nucleic acid or polypeptide can be physically isolated from the cell, or the nucleic acid or polypeptide can be present or maintained in another cell where it is not naturally present or synthesized.

As used herein, a "native" nucleic acid or polypeptide means a DNA, RNA or amino acid sequence or segment that has not been manipulated in vitro, i.e., has not been isolated, purified, and/or amplified.

As used herein, "natural promoter" means a nucleic acid segment with promoter function that is naturally operably linked to a coding region in the native genome of an organism (e.g., a plant). For example, a natural promoter for a CESA gene is the promoter that is present in the native genome of a plant species.

As used herein, "transgene" means a recombinantly engineered nucleic acid that includes at least a promoter segment that is operably linked to a segment encoding an amino acid sequence. The promoter can be (but need not be) heterologous to the segment encoding an amino acid sequence.

The following non-limiting Examples illustrate how aspects of the invention have been developed and can be made and used.

Example 1: Materials and Methods

This Example describes some of the materials and methods used in development of the invention.

Plant Materials and Growth Conditions

*Arabidopsis thaliana*, ecotype Columbia (Col-0), was used in both the wild-type and transgenic experiments. Plants were grown on soil in a growth chamber (16 h light/8 h dark) at 23° C.

RNA Extraction and Quantitative Real-Time PCR

Total RNA was extracted from liquid nitrogen-frozen samples using Plant RNeasy extraction kit (Qiagen). For quantitative real-time PCR analysis, total RNA was treated with DNase I and used for first-strand cDNA synthesis by SuperScript II Reverse Transcriptase (Invitrogen). Real-time PCR was performed using SYBR Premix Ex Taq™ (Takara) and ABI Prism 7900HT Sequence Detection System (ABI). The relative mRNA levels were determined by normalizing the PCR threshold cycle number of each gene with that of the ACT8 reference gene. Three biological replicates were used in the experiments.

Protein Expression and Purification

MYB46 was fused in frame with GST and expressed in *Escherichia coli* strain Rosetta gami (Novagen). The expression of the recombinant GST-MYB46 protein was induced by culturing the *E. coli* cells for 16 h at 16° C. in LB medium supplemented with 0.3 mM IPTG (isopropyl β-D-thiogalactopyranoside). The recombinant proteins for electrophoretic mobility shift assays (EMSAs) were purified using MagneGST™ Protein Purification System (Promega) according to the protocol provided in the kit.

Electrophoretic Mobility Shift Assay (EMSA)

DNA fragments for EMSA were obtained by PCR-amplification and labeled with [γ-$^{32}$P]ATP using T4 polynucleotide kinase (NEB). The end-labeled probes were purified with Microspin S-200 HR column (GE Healthcare). The labeled DNA fragments were incubated for 25 min with 50 ng of GST-MYB46 in a binding buffer [10 mM. Tris (pH 7.5), 50 mM KCl, 1 mM DTT, 2.5% glycerol, 5 mM $MgCl_2$, 100 μg/ml BSA, and 50 ng/μL poly(dI-dC)]. Five percent polyacrylamide gel electrophoresis (PAGE) was used to separate the recombinant protein-bound DNA fragments from the unbound ones. The gel was dried and placed in a film cassette and exposed to X-ray film (Kodak) for overnight. Radioactive fragments were visualized by autoradiography.

Dexamethasone Inducible Activation System for Confirmation of Direct Targets.

The full-length cDNA of MYB46 was fused to the N terminus of the glucocorticoid receptor (GR) coding sequence and ligated between the CaMV 35S promoter and the nopaline synthase terminator in pTrGUS vector (Ko et al., 2009). The MYB46-GR expression construct was introduced into *Arabidopsis* leaf protoplasts alone or together with the AtC3H14 promoter GUS construct (Ko et al., 2009). The primers used for the PCR amplification of the full-length MYB46 glucocorticoid receptor and AtC3H14 promoter were shown in Table S1. Preparation of *Arabidopsis* leaf protoplasts and transfection were carried out as described previously (Ko et al., 2009; Sheen, 2001). To activate MYB46, the protoplasts were treated with 10 μM dexamethasone (DEX, Sigma) for 5 h. The control protoplasts were mock-treated with the same concentration (0.01%) of ethanol used to dissolve DEX. To inhibit new protein synthesis, the protein synthesis inhibitor cycloheximide (2 μM) was added 30 min before addition of DEX (Zhong et al. 2008). After the treatments, the protoplasts were harvested for quantitative real-time PCR analysis and GUS activity analysis (Ko et al., 2009). The expression level of each gene in the control protoplasts without DEX treatment was set to 1, and three biological replications were used in the experiments.

Chromatin Immunoprecipitation Analysis

The full-length cDNA of MYB46 was fused in frame with GFP and ligated down-stream of the GAL4 upstream activation sequence in pTA7002 binary vector (Aoyama and Chua, 1997). The vector construct was used in the *Agrobacterium*-mediated transformation of *Arabidopsis thaliana* (Col-0) plants.

The MYB46-GFP/pTA7002 transgenic plants were grown on soil for three weeks before the DEX treatment. DEX (10 μM) was applied by spraying with 0.02% silwet surfactant (Lehle Seeds). Eight hours after the DEX treatment, aboveground portion of the plants were harvested and cross-linked with 1% formaldehyde for 10 min under vacuum. The cross-linking was quenched in 0.125 M glycine for 5 min. The cross-linked samples were washed twice with deionized water and then ground in liquid nitrogen into a fine powder for extraction of chromatin. To extract chromatin, 2 g of the ground powder was resuspended in 30 ml of Extraction Buffer 1 [10 mM Tris-HCl (pH 8.0), 0.4 M sucrose, 5 mM 2-mercaptoethanol, 1 mM PMSF, 1 tablet/50 ml protease inhibitor cocktail, and 4 μg/ml pepstain A] and filtered through two layers of Miracloth before centrifugation at 2500 g for 20 min at 4° C. The pellet was resuspended in 1 ml of Extraction Buffer 2 [10 mM Tris-HCl (pH 8.0), 0.25 M sucrose, 10 mM $MgCl_2$, 1% Triton X-100, 5 mM 2-mercaptoethanol, 1 mM. PMSF, 1× protease inhibitor cocktail, and 4 μg/ml pepstain A] and centrifuged at 14,000 g for 10 min at 4° C. The pellet was resuspended in 300 μl of Extraction Buffer 3 [10 mM Tris-HCl (pH 8.0), 1.7 M sucrose, 0.15% Triton X-100, 2 mM $MgCl_2$, 5 mM 2-mercaptoethanol, 1 mM PMSF, 1× protease inhibitor cocktail, and 4 μg/ml pepstain A] and then layered on top of a cushion of 300 μl of Extraction Buffer 3 and centrifuged at 14,000 g for 1 h at 4° C. The chromatin pellet was resuspended in 500 μl of ice cold Nuclei Lysis Buffer [50 mM Tris-HCl (pH 8.0), 10 mM EDTA, 1% SDS, 1 mM PMSF, 1× protease inhibitor cocktail, and 4 μg/ml pepstain A] and sonicated to small fragments with an average fragment size of 600-800 bp. The sonicated chromatin was diluted 10 times in ChIP Dilution Buffer [16.7 mMTris-HCl (pH 8.0), 1.1% Triton X-100, 1.2 mM EDTA, 167 mM NaCl, 1 mM PMSF, 1× protease inhibitor cocktail, and 4 μg/ml pepstain A] and precleared by incubation with Protein A agarose beads (Roch Applied Science) for 1 h at 4° C. The precleared chromatin was then incubated with 2 μg of GFP antibody (Abcam) overnight at 4° C. The MYB46-GFP-bound chromatin was purified by incubation with Protein A agarose beads for 1 h at 4° C. The agarose beads was washed sequentially with 1 ml each of the following wash buffers by gently rocking on a shaker for 5 min at 4° C.: (1) Low-Salt Wash Buffer [20 mM Tris-HCl (pH 8.0), 150 mM NaCl, 0.2% SDS, 0.5% Triton X-100 and 2 mM EDTA], (2) High-Salt Wash Buffer [20 mM Tris-HCl (pH 8.0), 500 mM NaCl, 0.2% SDS, 0.5% Triton X-100 and 2 mM EDTA], (3) LiCl Wash Buffer [10 mM Tris-HCl (pH 8.0), 0.25 M LiCl, 0.5% NP-40, 0.5% sodium deoxycholate and 1 mM EDTA] and (4) 2 times with TE buffer. The purified chromatin was eluted with 500 μl Elution Buffer (1% SDS and 0.1 M sodium bicarbonate at 65° C. for 15 min with gentle agitation in a gyratory shaking incubator. The eluted chromatin was incubated with 0.2 M NaCl to reverse the protein-DNA cross-linking at 65° C. overnight without agitation. Chromatin DNA was further purified by incubation with proteinase K (0.2 mg/mL) for 1 h to remove any residual proteins before the quantitative PCR analysis. Chromatin samples without GFP antibody immunoprecipitation was used as control. C3H14 and MYB54 promoters were used as positive and negative control, respectively. Three biological replications were used in the experiments.

Labeling for CBM3a and Immunofluorescence Microscopy

*Arabidopsis* thaliana plants, ecotype Columbia (Col-0) wild type and 35S:AtMYB46 transgenics, were grown on soil in a growth chamber (16 h light/8 h dark) at 23° C. for 8 weeks. Lower parts of the stems were fixed in FAA solution (50% ethanol, 5% glacial acetic acid and 3.7% formaldehyde) for 12 h at 4° C. After fixation, the fixed stems were embedded in paraffin and sectioned into 20 μm thin sections. The stem sections were labeled with a crystalline cellulose-specific carbohydrate-binding module CBM3a as described by McCartney et al. (2004). In brief, the sections were incubated in PBS containing 5% (w/v) milk protein (MP/PBS) and 10 μg/ml of the CBM3a for 1.5 h. Samples were then washed in PBS at least three times and incubated with a 100-fold dilution of mouse anti-his monoclonal antibody (Sigma) in MP/PBS for 1.5 h. After washing with PBS, anti-mouse antibody linked to fluorescein isothiocyanate (anti-mouse FITC; Sigma) was applied for 1.5 h as a 50-fold dilution in MP/PBS in darkness. The samples were washed with PBS, mounted in a ProLong® Gold anti-fade solution (Invitrogen), and observed on a confocal laser scanning microscope, fitted with 488 nm laser and 505-550 nm band-pas filter.

Cell Wall Crystalline Cellulose Composition Analysis

Cell wall crystalline cellulose compositions were determined as described previously (Ko et al., 2007). In brief, 3-weeks-old rosette leaves were collected from soil grown wild-type. 35S:AtMYB46 and DEX-inducible MYB46 over-expression plants, and ground in liquid nitrogen using a mortar and pestle. The ground samples (60-70 mg) were washed using 1.5 ml of 70% ethanol and centrifuged for 10 min at 10,000 g. The pellets were washed with 1.5 ml of chloroform:methanol (1:1 v/v) and again with 500 μl acetone. The remaining pellet was considered to be the cell walls and dried under nitrogen gas (N2). The cell wall materials were re-suspended in 250 μl of 2 M trifluoroacetic acid (TFA) and hydrolyzed for 90 min at 121° C. After the hydrolysis, samples were centrifuged for 10 min at 10,000 g to separate a TFA-soluble fraction (non-cellulosic monosaccharides) and TFA-insoluble fraction (cellulose). The TFA-insoluble fraction was washed with 300 μl of 2-propanol and evaporated at 40° C. The washed samples were treated with Updegraff reagent (Acetic acid:nitric acid:water, 8:1:2 v/v/v) and heated in aluminum block for 30 min at 100° C. (Undegraff D M, 1969). Then, the samples were centrifuged for 10 min at 10,000 g. The pellets were washed with water once and then 3 times with acetone. Air-dried pellet was Seaman hydrolyzed with 72% sulfuric acid for 30 min at room temperature (Selvendran and O'Neill, 1987). Final samples were precipitated for 5 min at 10,000 g and analyzed with Anthrone method.

Example 2: MYB46 Expression Increases Cellulose Synthase Activity

This example shows that while many CESA genes exist in *Arabidopsis*, and while MYB46 may stimulate expression of a number of different types of genes, MYB46 stimulates expression of only three secondary wall cellulose synthases. The data provided herein demonstrates that such up-regulation of these three CESA genes resulted in a substantial increase (up to 30%) in crystalline cellulose content in transgenic *Arabidopsis* plants.

Expression of the CESA4, CESA7 and CESA8 is up-regulated by MYB46

The inventors have identified a total of 37 genes whose expression may be modulated by a master regulator of secondary wall formation, MYB46 (At5g12870), in genome-wide survey of promoter sequences by using a MYB46-responsive cis-regulatory element (M46RE). Target genes that may be modulated by MYB46 were selected based on three criteria: (1) they have at least one M46RE in the promoter region, (2) they are up-regulated by MYB46, and (3) they are co-expressed with MYB46.

Figure 1B:
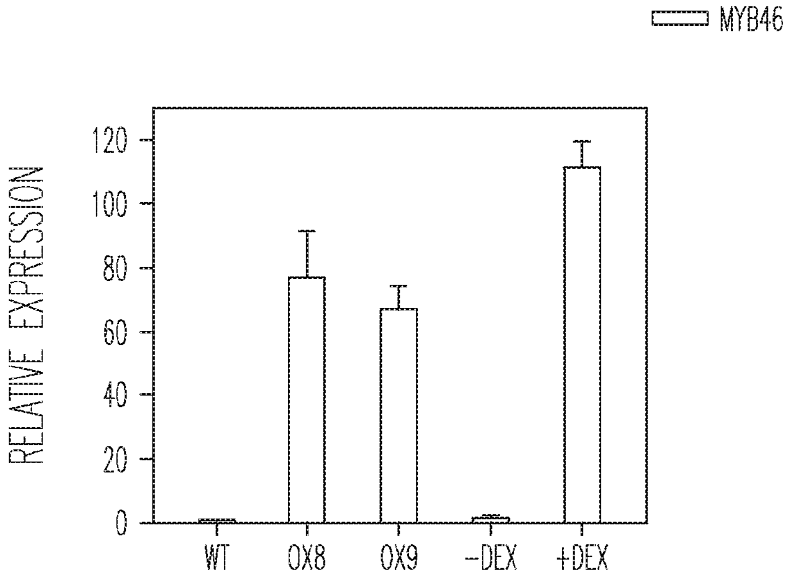
Figure 1C:
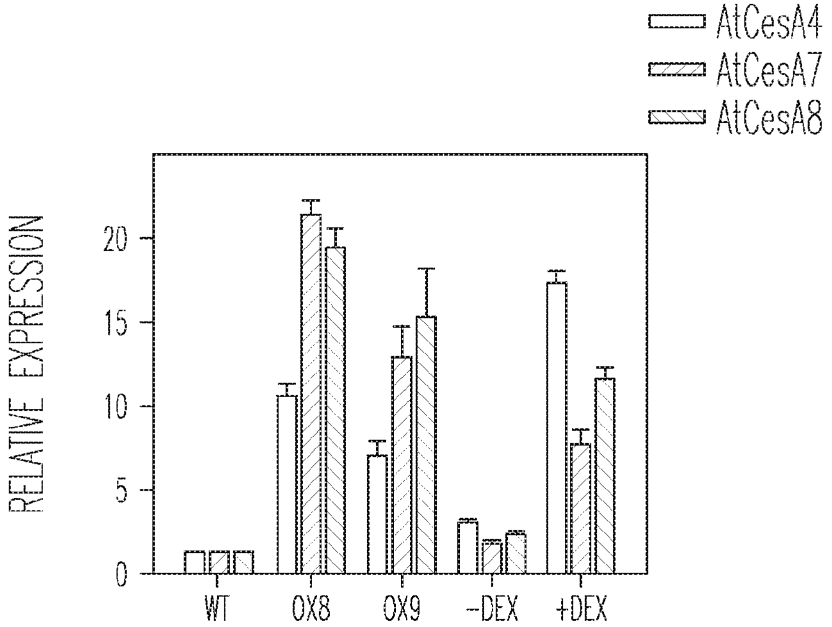

Genes that can be regulated by MYB46 include all three secondary wall cellulose synthases, CESA4 (At5g4430), CESA7 (At5g17420) and CESA8 (At4g18780). As a step toward verifying whether expression of CESA4 (At5g4430), CESA7 (At5g17420) and CESA8 (At4g18780) can actually be regulated by MYB46, the inventors performed real time-PCR to examine the expression pattern of these CESA genes in transgenic *Arabidopsis* plants that exhibited either constitutive or inducible over-expression of MYB46, These real time-PCR analyses showed that all of the three CESAs were highly up-regulated by either constitutive or inducible over-expression of MYB46 (FIG. 1).

Transcription of the CESA4, CESA7 and CESA8 is directly activated by MYB46

To investigate whether MYB46 can directly activate the transcription of these three CESAs, a steroid receptor-based inducible activation system was employed. In this system, a transcription factor fused with a steroid binding domain is sequestered in the cytoplasm by binding to a cytoplasmic complex. Upon steroid treatment, the complex disrupts and then transcription factor can enter the nucleus and regulate the expression of downstream target genes. Coupled with a protein synthesis inhibitor, this steroid-mediated activation system has been widely used to identify direct targets of a transcription factor in plants (Sablowski and Meyerowitz, 1998; Wagner et al., 1999; Baudry et al., 2004; Zhong et al., 2008).

Figure 2A:
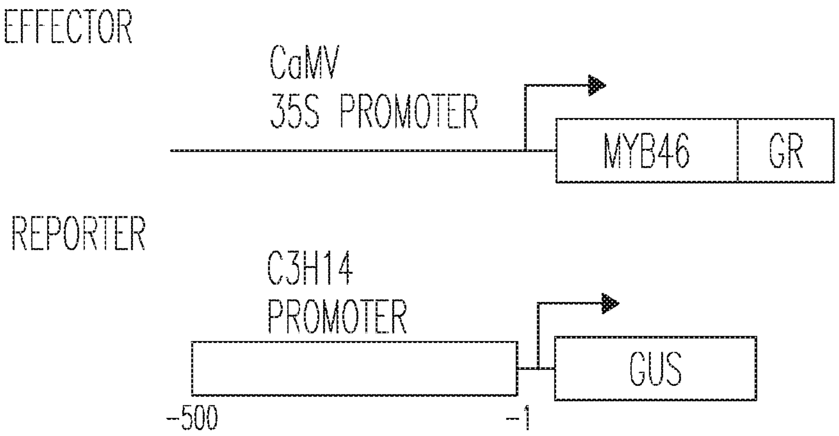
FIG. 2A-D illustrate that MYB46 directly activates the expression of CESA4, CESA7 and CESA8.
Figure 2B:
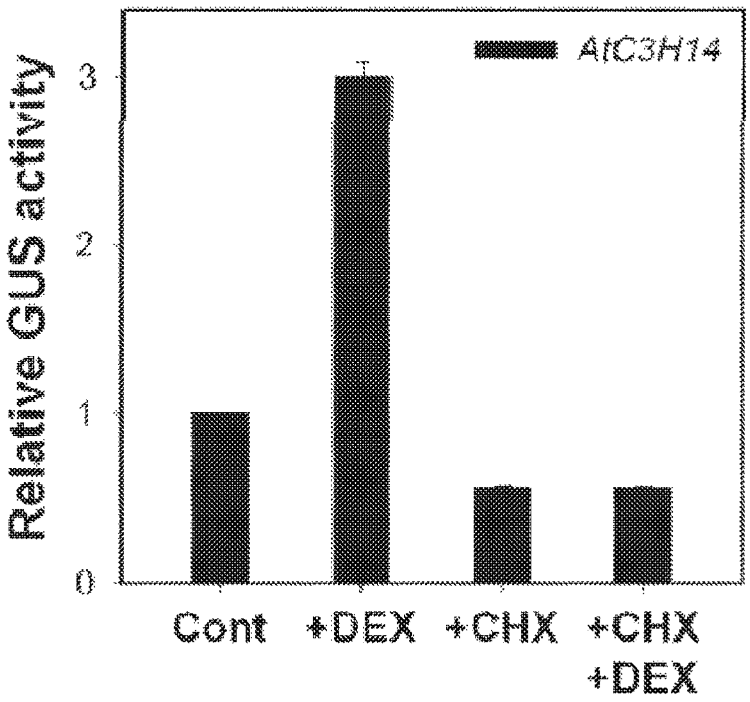
Figure 2C:
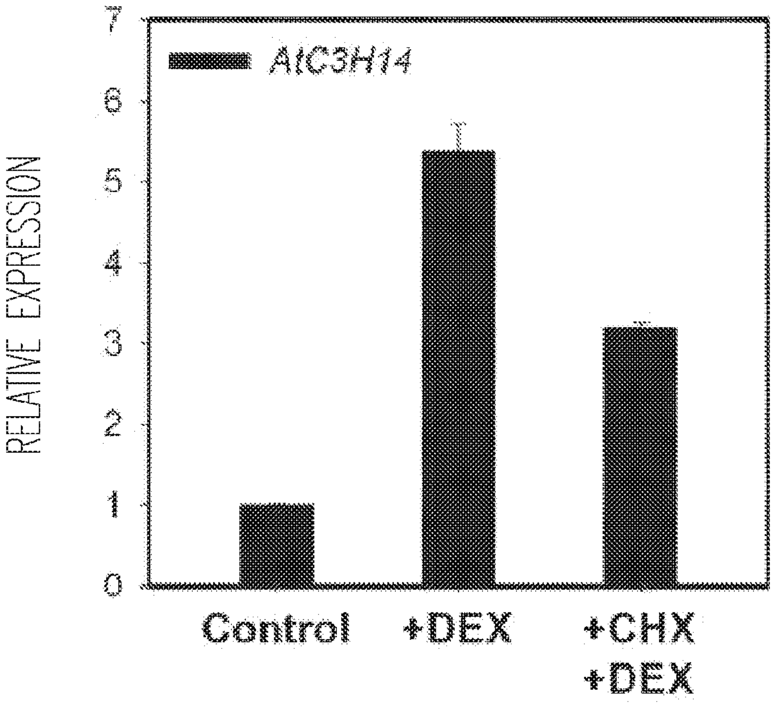
Figure 2D:
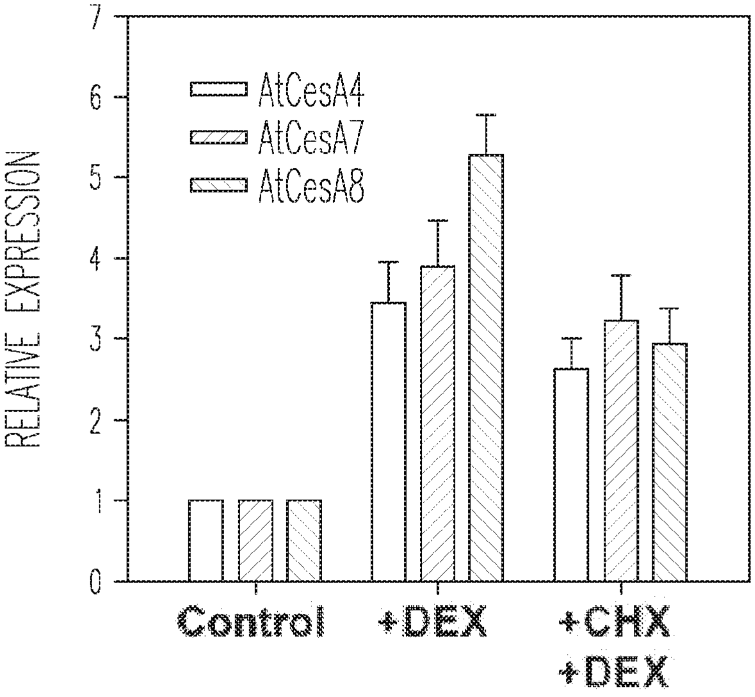

In this study, MYB46 was fused with the regulatory region of glucocorticoid receptor (MYB46-GR) and constitutively expressed as the MYB46-GR fusion protein under the control of CaMV 35S promoter in *Arabidopsis* leaf protoplasts (FIG. 2A). As a positive control of the experimental system, the promoter sequence of a known direct target, AtC3H14, of MYB46 (Ko et al., 2009) was used to drive a GUS reporter gene. Upon dexamethasone (DEX) treatment, the MYB-GR chimeric protein became functional to activate GUS reporter activity driven by the AtC3H14 promoter (FIGS. 2A, B). While the GUS activity induced by the DEX-activated MYB46-GR was completely abolished by cycloheximide (CHX) treatment, an inhibitor of protein synthesis (FIG. 2B), the expression of the positive control AtC3H14 was clearly induced by the DEX-activated MYB46-GR with CHX pretreatment (FIG. 2C). The induction level of AtC3H14 by MYB46-GR was lower with the cycloheximide treatment compared to no treatment, which may reflect cycloheximide inhibition of the overall protein synthesis, including that of MYB46-GR (FIG. 2C). Likewise, the DEX-activated MYB46-GR could activate the expression of all of the three secondary wall CESA genes, even with the cycloheximide treatment (FIG. 2D). This result indicates that MYB46 directly activates the transcription of all of the three CESA genes tested.

MYB46 Binds to the Promoters of CESA4, CESA7 and CESA8 Genes

Figure 3B:
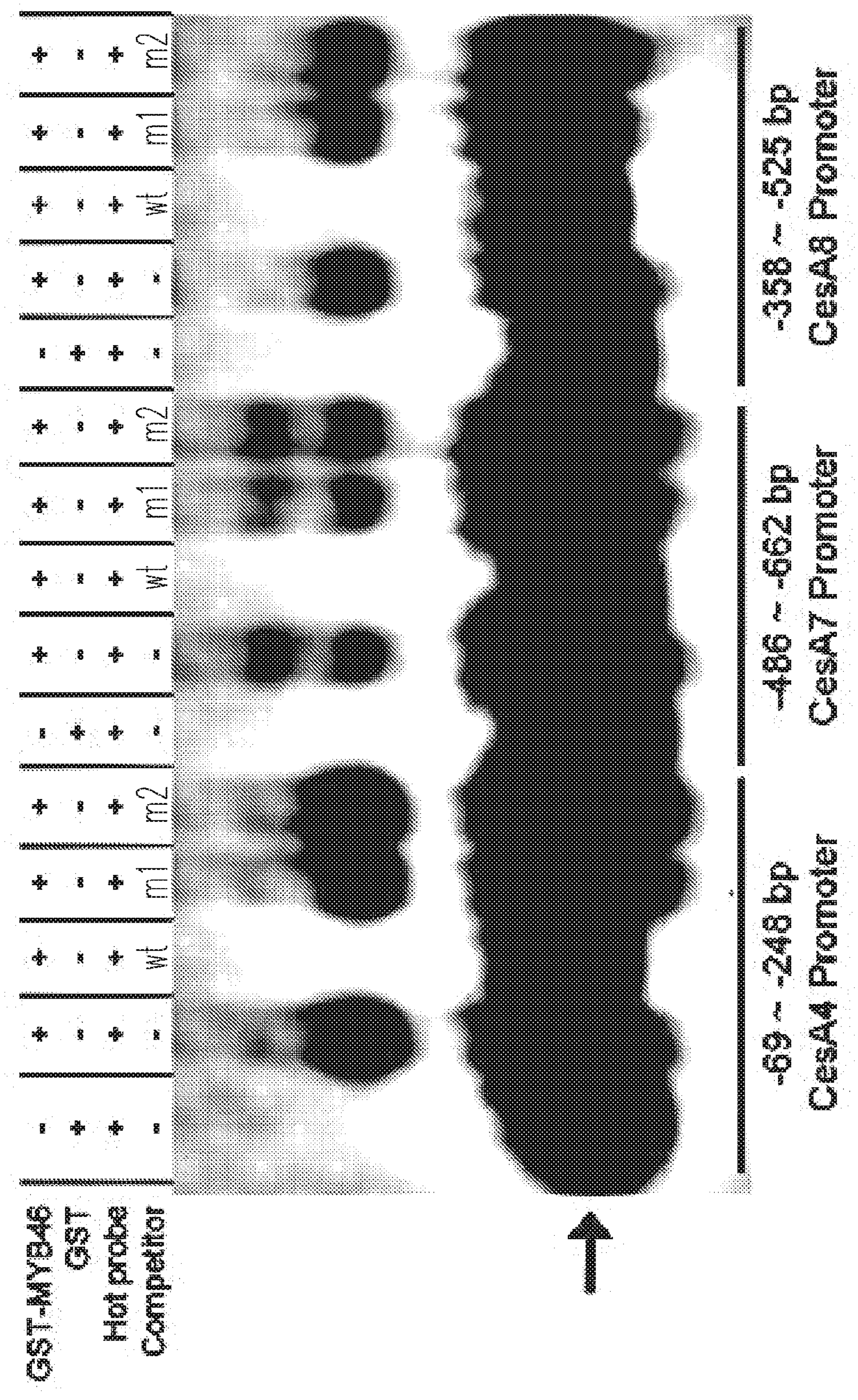

To confirm the physical interaction of MYB46 protein with the promoter regions of CESA4, CESA7 and CESA8 genes, we performed electrophoretic mobility shift assays (EMSA) using recombinant MYB46 proteins fused with glutathione S-transferase (GST-MYB46) and CESA promoter fragment containing a M46RE motif (FIG. 3). Specific binding of MYB46 to the $^{32}P$-labeled promoter fragments, ProCESA4 (−248 to −69), ProCeA7 (−662 to −486), and ProCESA8 (−525 to −358) was established using; non-labeled promoter fragments (e.g., ProCESA4_wt, FIG. 3A) as a competitor (FIG. 3B). The binding specificity was further confirmed by using non-labeled promoter fragments with single base mutation in the M46RE (e.g., ProCESA4_m1 or m2) as a competitor. As expected, the MYB46 protein could bind to the CESA promoter fragments while the GST protein alone could not bind to the fragments (FIG. 3B), demonstrating the interaction of MYB46 protein with the promoters of the three CESA genes in vitro.

Figure 4A:
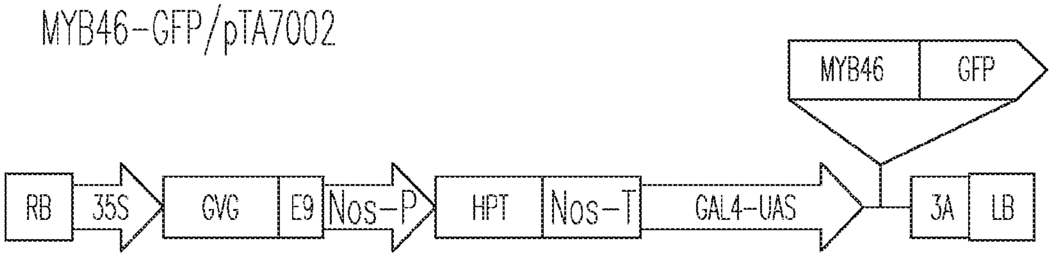
FIG. 4A-B illustrate a chromatin immunoprecipitation (ChIP) analysis of MYB46 binding to the CESA promoter sequences in vivo.
Figure 4B:
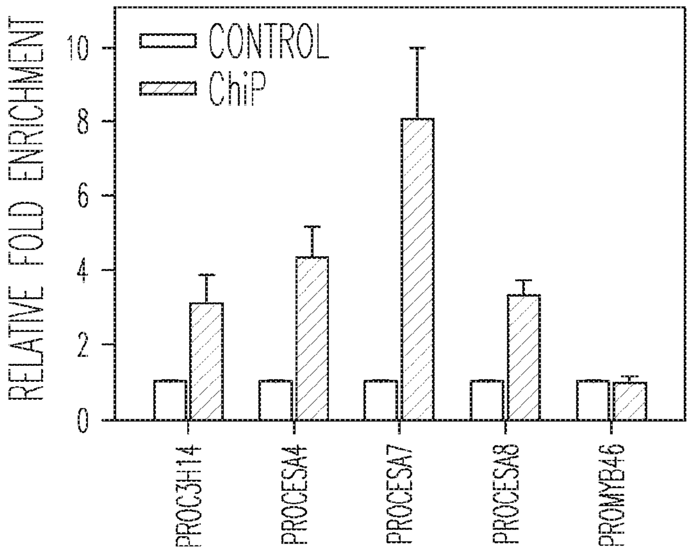

To further corroborate the interaction of MYB46 protein with the three CESA promoters in vivo, the chromatin immunoprecipitation assay (ChIP) was performed using transgenic *Arabidopsis* plants that are over-expressing GFP-tagged MYB46 gene under the control of DEX-inducible promoter (FIG. 4A). DEX treatment of the MYB46-GFP over-expression plants caused ectopic secondary wall thickening in the leaf epidermal and mesophyll cells (data not shown), which is a typical phenotype of ectopic MYB46 over-expression as described previously (Ko et at, 2009). This indicates that the MYB46-GFP fusion protein can be used for analysis of MYB46 binding sequences. Formaldehyde cross-linked chromatin from the leaf tissues collected from 3-week-old transgenic plants with or without DEX treatment was isolated and fragmented. Chromatin fragments from without DEX treatment were used as a negative control. MYB46-GFP-bound DNA fragments were immunoprecipitated by using GFP antibody and used as templates in the quantitative real-time PCR analysis of CESA promoter sequences. All of the three CESA promoters were highly enriched (3-8 fold) compared to control DNA (FIG. 4B). In the ChIP analysis, we used AtC3H14 and MYB54 as a positive and a negative control, respectively, since MYB54 is not a direct target of MYB46.

Along with the finding that the expression of CESA4, CESA7 and CESA8 are directly activated by MYB46, these results provide both in vitro and in vivo evidence that MYB46 directly binds to the promoter of all of the three secondary wall-associated CESA genes to activate their expression.

Increase of Cellulose Contents by Up-Regulation of MYB46

Figure 5A:
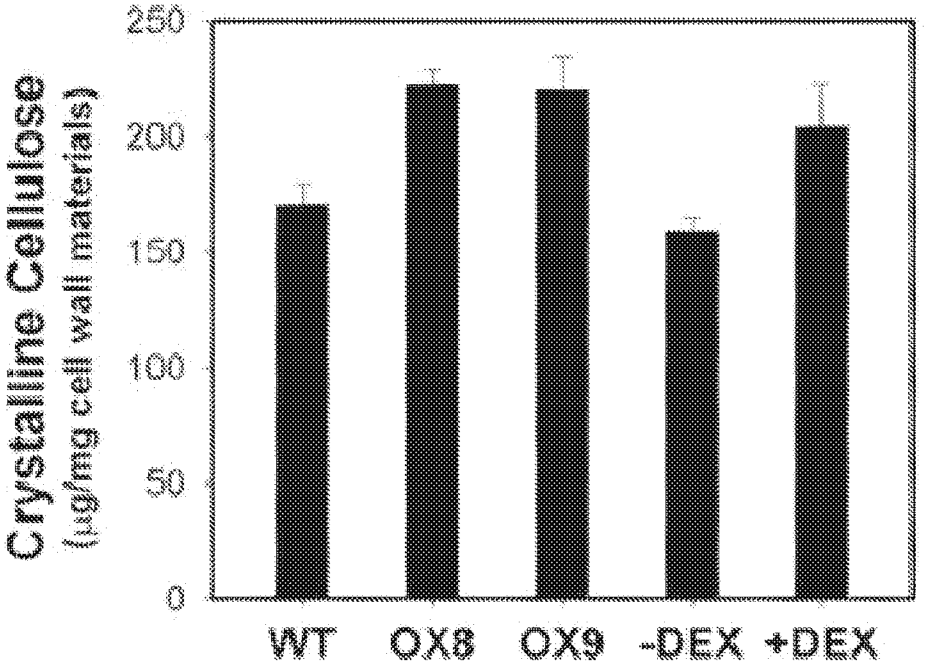
FIG. 5A-B illustrate changes in cell wall crystalline cellulose composition detected when MYB46 is over-expressed in wild type *Arabidopsis* (WT) and transgenic *Arabidopsis* plants. The transgenic *Arabidopsis* plants OX8 and OX9 over-express the MYB46 transcription factor, while the DEX transgenic *Arabidopsis* plant has a dexamethasone-inducible MYB46 transgene. MYB46 expression in the DEX plants was induced by 24 hr of dexamethasone treatment (+DEX). As a control, a DEX plant was mock-treated for 24 hr with 0.05% ethanol and of 0.02% silwet surfactant (−DEX).

MYB46 directly regulate the expression of CESA4, CESA7 and CESA8 genes. An increase of cellulose content may be observed when MYB46 expression is increased. To test this hypothesis, the crystalline cellulose content was measured of transgenic *Arabidopsis* plants with either constitutive or inducible over-expression of MYB46 (FIG. 5A). Compared to that of wild-type plants, two independent lines of constitutive overexpressors of MYB46 (OX8 and OX9) had a substantial increase (about 30%) increase in crystalline cellulose content in the leaf tissues of 3-week-old plants. Furthermore, just 24-hr induction of MYB46 resulted in up to 27% increase compared to that of non-induced plants (FIG. 5A).

Figure 5B:
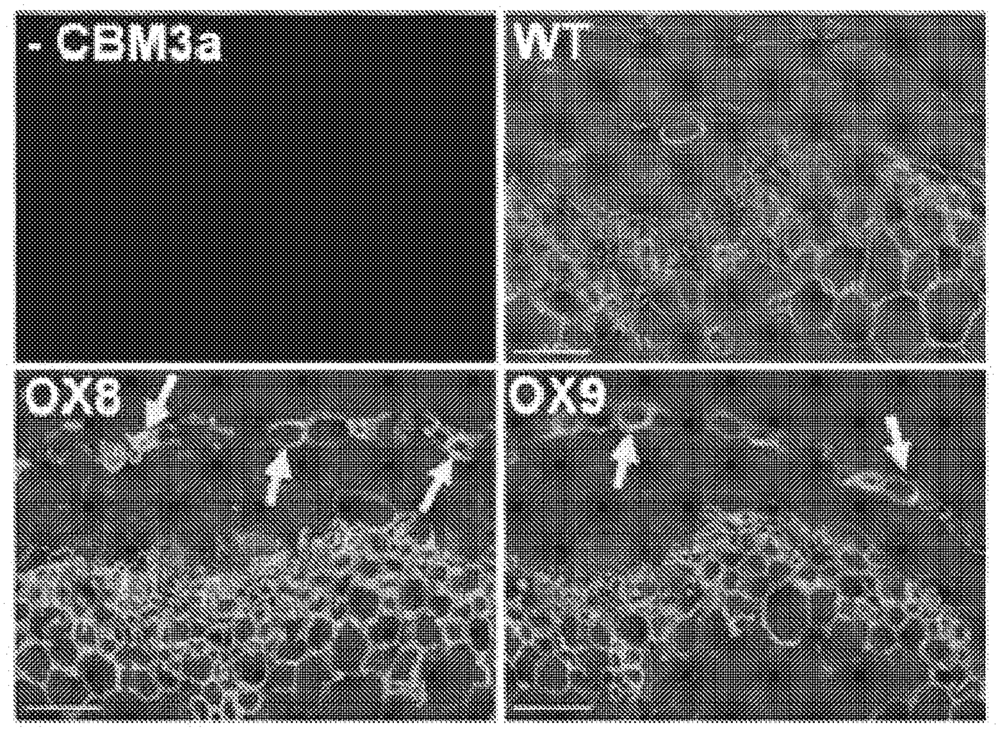

Crystalline cellulose accumulation in the stems of MYB46 overexpressors was visualized by immune-histological staining of cellulose using CBM3a, a carbohydrate-binding module for crystalline cellulose (Blake et al., 2006). Compared to wild-type plants, fluorescent signal driven by cellulose accumulation was more evident in the xylem and interfascicular regions of the two constitutive MYB46 overexpressors (OX8 and OX9) (FIG. 5B). Furthermore, in both of the two constitutive overexpressors, fluorescent signals were detected in epidermal cells where secondary wall formation does not occur normally, while no signals were noted in the wild-type plants (FIG. 5B).

Taken together, these results confirm that ectopic up-regulation of MYB46 resulted in substantial increase of cellulose contents through activation of the three secondary wall CESA genes in plants.

Example 3: HAM1 and HAM2 Transcription Factors Bind to CESA Promoters

This Example describes experiments illustrating that while the HAM1 transcription factor binds to the CESA4 promoter, the HAM2 transcription factor binds to both the CESA4 and the CESA7 promoters.

Procedures similar to those described in Examples 1 and 2 were used to ascertain whether the HAM1 or HAM2 transcription factors physically interact with any the promoter regions of CESA genes. Briefly, electrophoretic mobility shift assays (EMSA) were performed using recombinant HAM1 and HAM2 proteins fused with glutathione S-transferase to ascertain whether these proteins hound to a selected CESA promoter fragment. Specific binding of HAM1 and HAM2 to the following $^{32}P$-labeled promoter fragments was tested: CESA4 Pro1 (−666 to −294), CESA4 Pro2 (−248 to −1), and CesA7 Pro4 (−260 to −1). Binding was established using a fifty-fold excess of corresponding non-labeled promoter fragment as a competitor.

Figure 6:
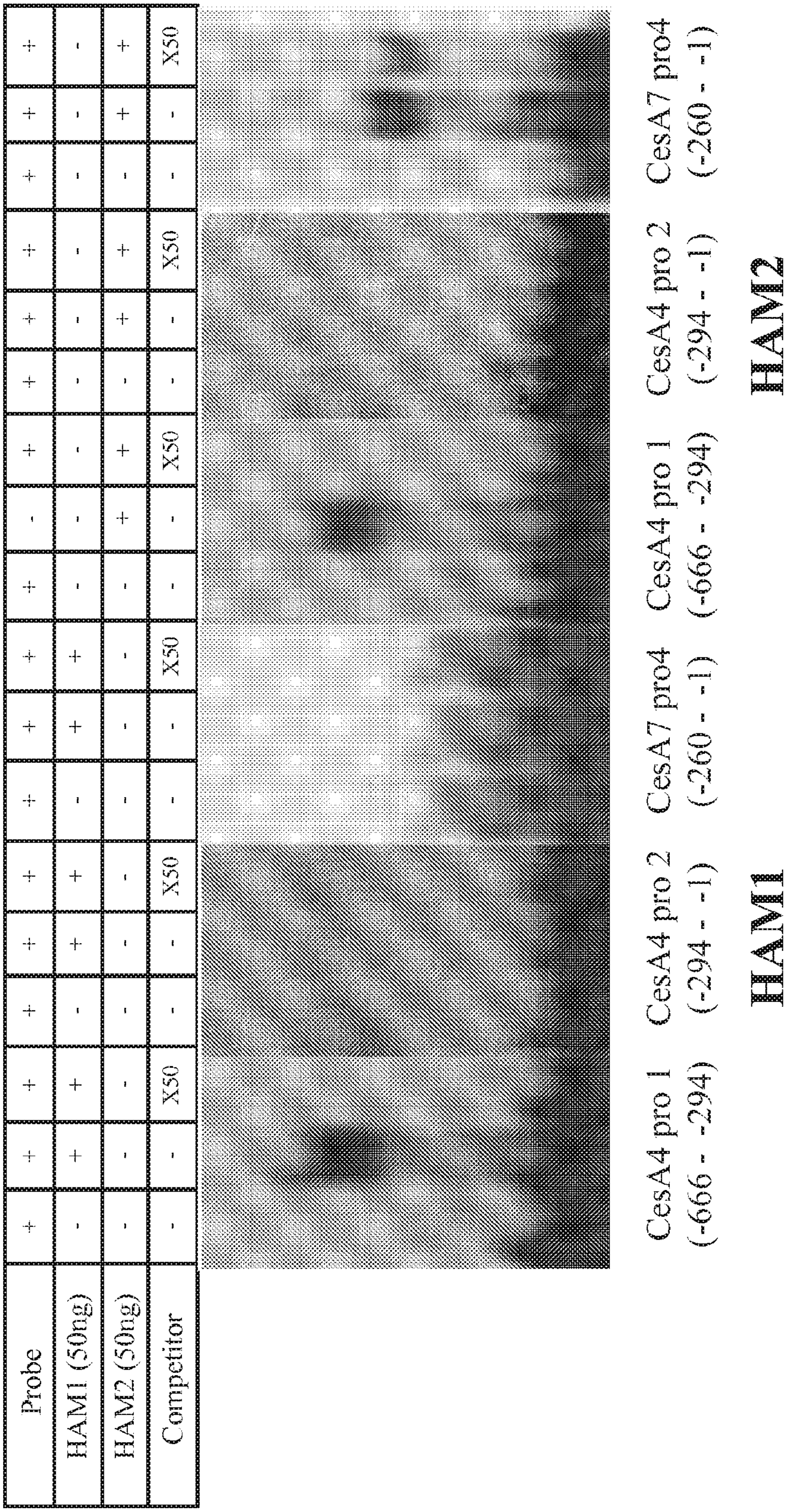
FIG. 6 illustrates to which CESA promoters the HAM1 and HAM2 factors bind, as detected by electrophoretic mobility shift assays. As shown, both HAM1 and HAM2 bind to the CESA4 promoter in the region of nucleotide position −666 to −294 upstream from the coding region of CESA4. The HAM2 factor also bound to the CESA7 promoter in the region of nucleotide position −260 to −1 upstream from the coding region of CESA7. Procedures similar to those described above for FIG. 3 were employed.

The HAM1 protein bound to the CESA4 Pro1 (−666 to −294) fragment but no significant binding was observed to the CESA4 Pro2 (−294 to −1) promoter or to the CesA7 Pro4 (−260 to −1) promoter fragment (FIG. 6).

In contrast, the HAM2 protein hound to the CESA4 Pro1 (−666 to −294) and ProCeA7 (−260 to −1) promoter fragments, but no significant binding was observed to the CESA4 Pro2 (−294 to −1) promoter fragment (FIG. 6).

Example 4: MYB112 Transcription Factor Binds to a CESA Promoter

This Example describes experiments illustrating that the MYB112 transcription factor binds to upstream regions of the CESA4 promoter.

Procedures similar to those described in Examples 1-3 were used to ascertain whether the MY B112 transcription factor physically interacts with the promoter regions of CESA genes. Briefly, electrophoretic mobility shift assays (EMSA) were performed using recombinant MYB112 protein fused with glutathione S-transferase to ascertain whether the MYB112 protein bound to a selected CESA promoter fragment. Specific binding of MYB112 to the following $^{32}$P-labeled promoter fragments was tested: CESA4 Pro1 (−666 to −294) and CESA4 Pro2 (−294 to −1). Binding was established using a ten- or fifty-fold excess of corresponding non-labeled promoter fragment as a competitor.

Figure 7:
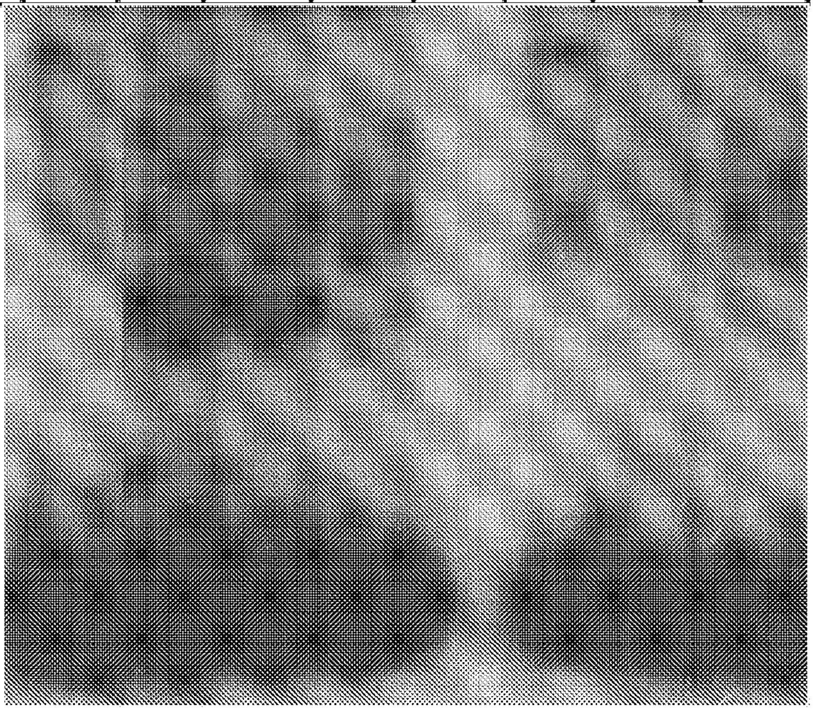
FIG. 7 illustrates to which CESA promoters the MYB112 factor binds, as detected by electrophoretic mobility shift assays. As shown, the MYB112 factor binds to the CESA4 promoter in the region of nucleotide position −666 to −294 upstream from the coding region of CESA4. Procedures similar to those described above for FIG. 3 were employed.

The MYB112 protein bound to the CESA4 Pro1 (−666 to −294) fragment but no significant binding was observed to the CESA4 Pro2 (−294 to −1) promoter fragment (FIG. 7).

Example 5: The WRKY11 Transcription Factor Binds to a CESA Promoter

This Example describes experiments illustrating that the WRKY11 transcription factor binds to upstream regions of the CESA4 promoter.

Procedures similar to those described in Examples 1-4 were used to ascertain whether the WRKY11 transcription factor physically interacts with the promoter regions of CESA genes. Briefly, electrophoretic mobility shift assays (EMSA) were performed using recombinant WRKY11 protein fused with glutathione S-transferase to ascertain whether the WRKY11 protein bound to a selected CESA promoter fragment. Specific binding of MYB112 to the following $^{32}$P-labeled promoter fragments was tested: CESA4 Pro1 (−666 to −294) and CESA4 Pro2 (−294 to −1). Binding was established using a fifty-fold excess of corresponding non-labeled promoter fragment as a competitor.

Figure 8:
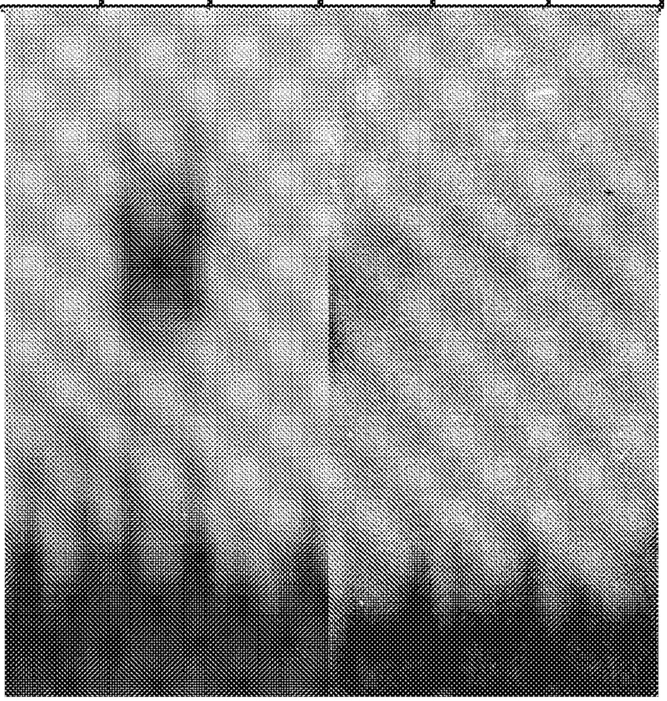
FIG. 8 illustrates to which CESA promoters the WRKY11 factor binds, as detected by electrophoretic mobility shift assays. As shown, the WRKY11 factor binds to the CESA4 promoter in the region of nucleotide position −666 to −294 upstream from the coding region of CESA4. Procedures similar to those described above for FIG. 3 were employed.

The WRKY11 protein bound to the CESA4 Pro1 (−666 to −294) fragment but no significant binding was observed to the CESA4 Pro2 (−294 to −1) promoter fragment (FIG. 8).

Example 6: The ERF6 Transcription Factor Binds to a CESA Promoter

This Example describes experiments illustrating that the ERF6 transcription factor binds to upstream regions of the CESA4 promoter.

Procedures similar to those described in Examples 1-5 were used to ascertain whether the ERF6 transcription factor physically interacts with the promoter regions of CESA genes. Briefly, electrophoretic mobility shift assays (EMSA) were performed using recombinant ERF6 protein fused with glutathione S-transferase to ascertain whether the ERF6 protein bound to a selected CESA promoter fragment. Specific binding of ERF6 to the following $^{32}$P-labeled promoter fragments was tested: CESA4 Pro1 (−666 to −294) and CESA4 Pro2 (−294 to −1). Binding was established using a fifty-fold excess of corresponding non-labeled promoter fragment as a competitor.

Figure 9:
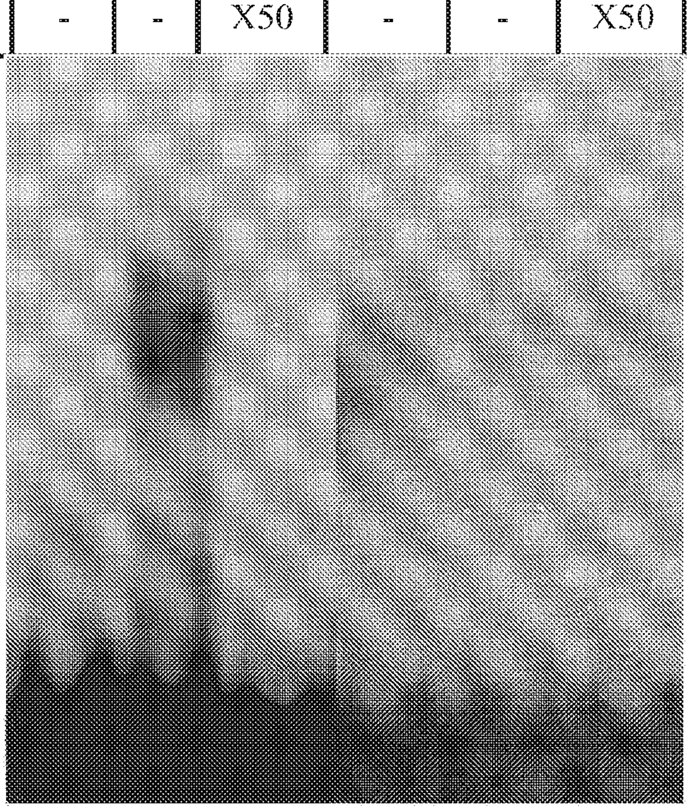
FIG. 9 illustrates to which CESA promoters the ERF6 factor binds, as detected by electrophoretic mobility shift assays. As shown, the ERF6 factor binds to the CESA4 promoter in the region of nucleotide position −666 to −294 upstream from the coding region of CESA4 Procedures similar to those described above for FIG. 3 were employed.

The ERF6 protein bound to the CESA4 Pro1 (−666 to −294) fragment but no significant binding was observed to the CESA4 Pro2 (−294 to −1) promoter fragment (FIG. 9).

Example 7: MYB46 is Needed for Expression of Secondary Wall-Associated Cellulose Synthases in *Arabidopsis*

This Example further illustrates the function of MYB46 and demonstrates that it is a key transcription factor for up-regulation of CESA4, CESA7 and CESA8 gene expression.

Materials and Methods

Plant Materials and Growth Conditions.

*Arabidopsis thaliana* ecotype Columbia (Col-0) and three T-DNA insertional mutants of cesa [cesa4 (SALK_084627), cesa7 (SALK_029940) and cesa8 (SALK_026812)](FIG. 10) were used in the experiments. Plants were grown on soil in a growth chamber (16 h light/8 h dark) at 23° C. All experiments were performed in triplicates and repeated at least three times.

Plasmids Construction and Plant Transformation.

Figure 11:
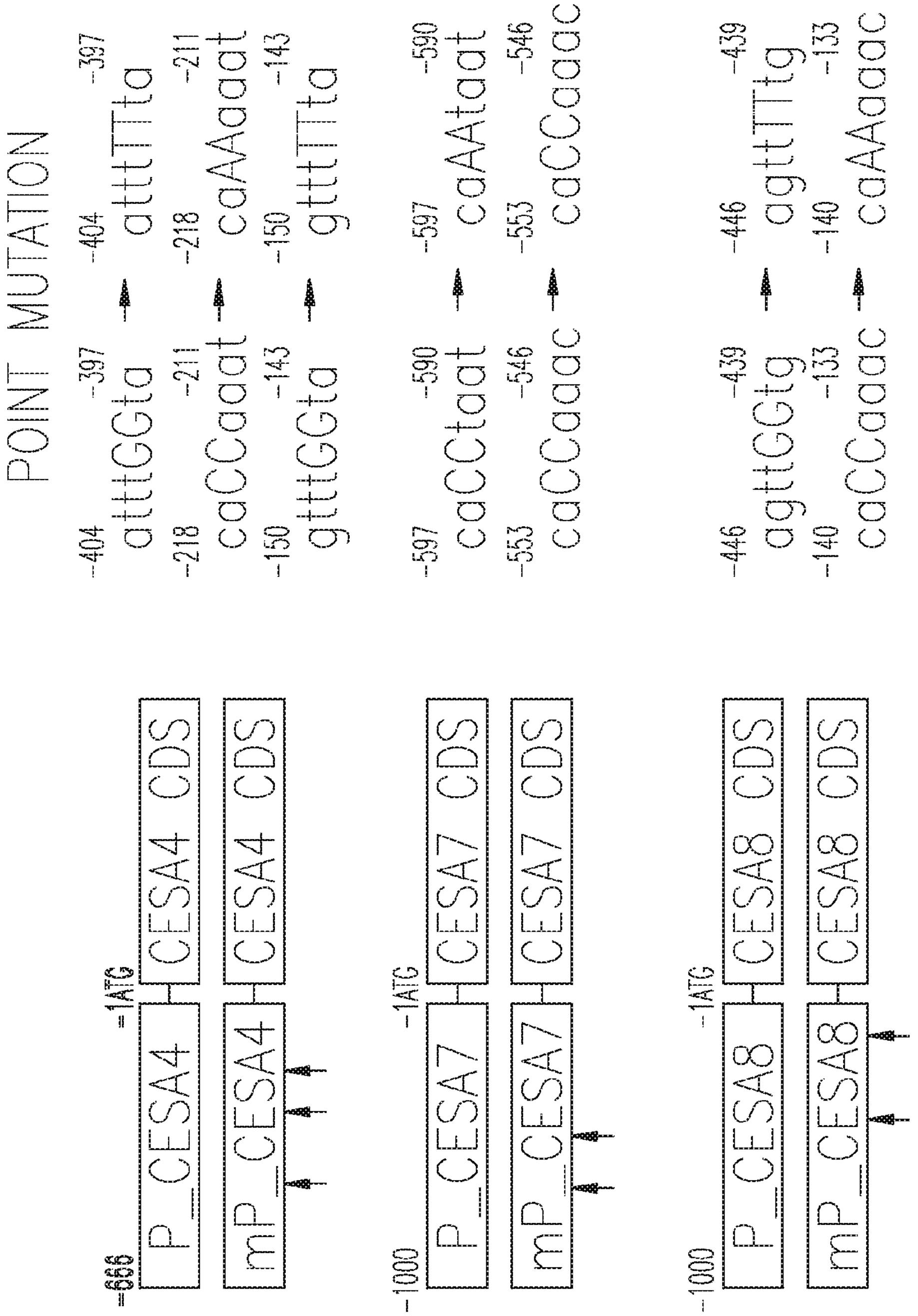
FIG. 11 is a schematic diagram showing point mutations n the promoters of CESA4, CESA7 and CESA8 (SEQ ID NO: 65-78). The vertical arrows indicate the locations of the mutation points and the sequences shown are listed in Table 2.

All of the constructs used in this study were verified by DNA sequencing. The coding regions of CESA4 (At5g44030), CESA7 (At5g17420) and CESA8 (At4g18780) were obtained by PCR amplification from stein cDNAs of *Arabidopsis*. For the genetic complementation, the PCR-amplified coding region was fused with either native or mutated promoter from the CESA genes (FIG. 11). The mutated promoter was created by PCR-based point mutations of the two base pairs critical in the M46RE (Kim et al., *Plant Molecular Biology* 78: 489-501 (2012)) as shown in FIG. 11. The primers used in this experiment are listed in Table 1.

TABLE 1

Primer sequences

| Primers | Sequence | SEQ ID NO: |
|---|---|---|
| | CESA4 - AGI No. AT5G44030 | |
| Pro-Forward | CCCACTAGTTAAATCTTATTTACTAACAAAACAATAAGA | 22 |
| Pro-Reverse | CCCCTCGAGGGCGAGGTACACTGAGCTC | 23 |
| Pro-Mutation-F1 | GATTCAAGAACATAGCCAGATTTTTTAAAGT | 24 |
| Pro-Mutation-R1 | TCTTACTTAATATTTTGTATCTTATAAACTTTAAAAAATCT | 25 |

TABLE 1-continued

Primer sequences

| Primers | Sequence | SEQ ID NO: |
|---|---|---|
| Pro-Mutation-F2 | TGAGCTGTCTCCTTCTTCCA**AA**AAATCT | 26 |
| Pro-Mutation-R2 | TTCAAGAGACAGCAACAAGATTT**TT**TGGAAG | 27 |
| Pro-Mutation-F3 | GACCCAATTTCACTCACAGTTTTTACAAC | 28 |
| Pro-Mutation-R3 | GTTGTGAAGAAAACTGAGGTTGTAAAAAACTG | 29 |
| CDS-F1 | CCCCTCGAGATGGAACCAAACACCATGG | 30 |
| CDS-R1 | GTACTGCAGAGACTCGAACCA | 31 |
| CDS-F2 | TCTCTGCAGTACTCACTAATGCTC | 32 |
| CDS-R2 | CCCACTAGTTTAACAGTCGACGCCACAT | 33 |
| RT-Forward | CAACAGATGATGATGACTTTGGA | 34 |
| RT-Reverse | AGACCTTTGAGGAATGGGTAGAG | 35 |
| SALK R | GGACGCCATTGCTGCTTACTGTTG | 79 |
| CESA7 - AGI No. AT5G17420 | | |
| Pro-Forward | CCCGAGCTCAGATTGAGGATCATTTTATTTATTTATTAG | 36 |
| Pro-Reverse | CCCCTCGAGAGGGACGGCCGGAGA | 37 |
| Pro-Mutation-F1 | TAGCTTATGTATGCAGAAAATTCA**AA**TAATTA | 38 |
| Pro-Mutation-R1 | GTTACGTTCCCTGTCCTTAATTATTTGAATT | 39 |
| Pro-Mutation-F2 | TGGCTTGCACTCCTCTCA**AA**AAAACCT | 40 |
| Pro-Mutation-R2 | AAATTAGTTAGGGGGTAAGGTTTTTTGAGAG | 41 |
| CDS-F1 | CCCCTCGAGATGGAAGCTAGCGCCG | 42 |
| CDS-R1 | TGAGGATCCATCAAAAAACAC | 43 |
| CDS-F2 | GATGGATCCTCAGATTGGAA | 44 |
| CDS-R2 | CCCGAGCTCTCAGCAGTTGATGCCACA | 45 |
| RT-Forward | CAACAGATGATGATGACTTTGGA | 46 |
| RT-Reverse | AGACCTTTGAGGAATGGGTAGAG | 47 |
| SALK R | GCAAGCTACGAAGAGGTCTCC | 48 |
| CESA8 - AGI No. AT4G18780 | | |
| Pro-Forward (TAA) | CCCACTAGTTGATGGATGGTTTTGCTGTA | 49 |
| Pro-Reverse (TAA) | CCCCTGCAGCTTCGAATTCCCCTGTTTG | 50 |
| Pro-Mutation-F1 | GATTTTAATTCTTATTTTTCTTATAGAAAGTT**TT**TGATTG | 51 |
| Pro-Mutation-R1 | TTATAATTTTTAAGTAAATCTTTTCAATCAAAAACTTT | 52 |
| Pro-Mutation-F2 | TCCGATTTTTCACAATCCA**AA**AAACTT | 53 |
| Pro-Mutation-R2 | AGGAAAAAAAGTTATTAAAAAAAGTTTTTTGGATT | 54 |
| CDS-F1 | CCCCTGCAGATGATGGAGTCTAGGTCTCCC | 55 |
| CDS-R1 | ACAGGATCCATTAAAAAGCAC | 56 |
| CDS-F2 | AATGGATCCTGTTGTTGGTC | 57 |
| CDS-R2 | CCCACTAGTTTAGCAATCGATCAAAAGACAG | 58 |
| RT-Forward | CGATGTTAATATGAGAGGGCTTG | 59 |
| RT-Reverse | GGAAGGATCTTGAGGTTGTTTCT | 60 |
| SALK R | GTACTTATATGTCTAGCATGAATCCCTG | 61 |
| Left-border primer | ATTTTGCCGATTTCGGAAC | 62 |
| ACT8 - ACI No. AT1G49240 | | |
| RT-Forward | ATGAAGATTAAGGTCGTGGCA | 63 |
| RT-Reverse | TCCGAGTTGAAGAGGCTAC | 64 |

CDS, coding sequence; Pro, promoter; Underlined letters indicate the restriction enzyme sites used for the cloning into the vector; Underlined and bold letters indicate the point mutations introduced.

Figure 12:
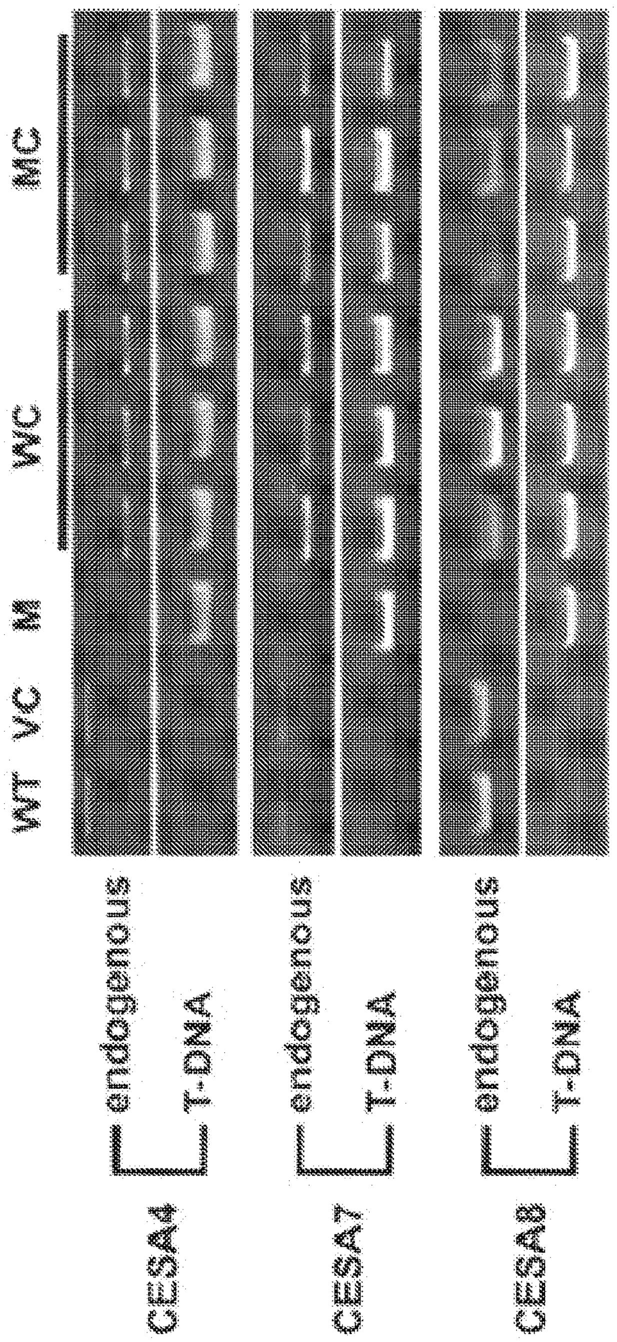
FIG. 12 shows electrophoretically separated amplicons confirming genetic complementation in the transgenic *Arabidopsis* plants by genomic DNA PCR. WT, wild-type; VC, vector control; M, cesa T-DNA insertion mutants; WC, genetic complementation of the mutants with native promoter-driven CESA CDS; MC, genetic complementation of the mutants with mutated promoter-driven CESA CDS; T-DNA, the amplified DNA fragment with the T-DNA left border primer and the CESA4, CESA7 and CESA8 primers flanking the T-DNA insertion site; Endogenous, the amplified CESA4, CESA7 and CESA8 DNA fragments by the forward and reverse CESA primers (Table 1).
Figure 13A:
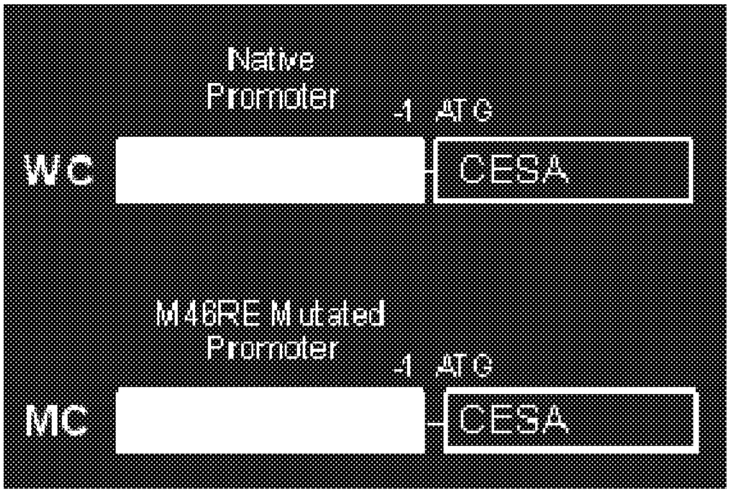
FIG. 13A-D illustrates that MYB46 is required for functional expression of CESA4, CESA7, and CESA8 in *Arabidopsis*.
Figure 13B:
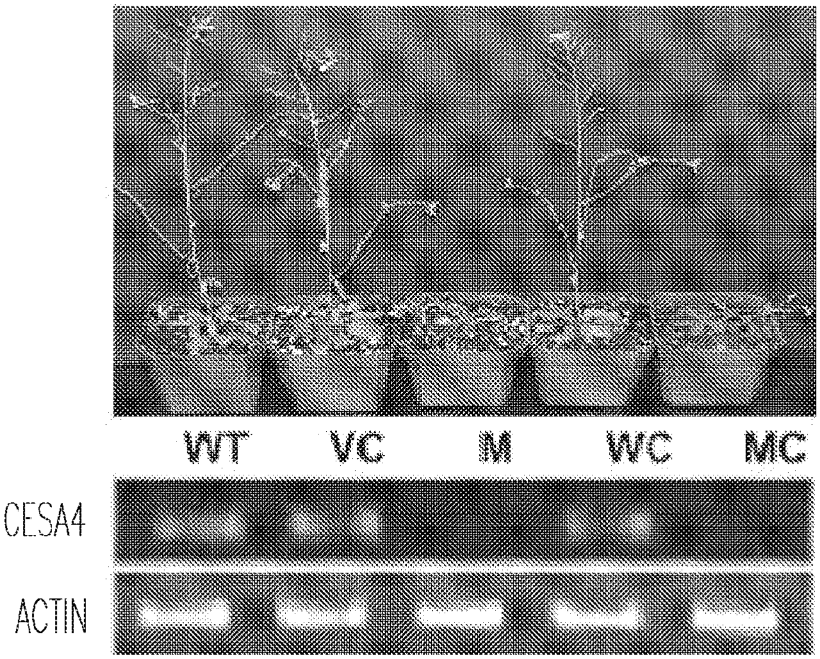
Figure 13C:
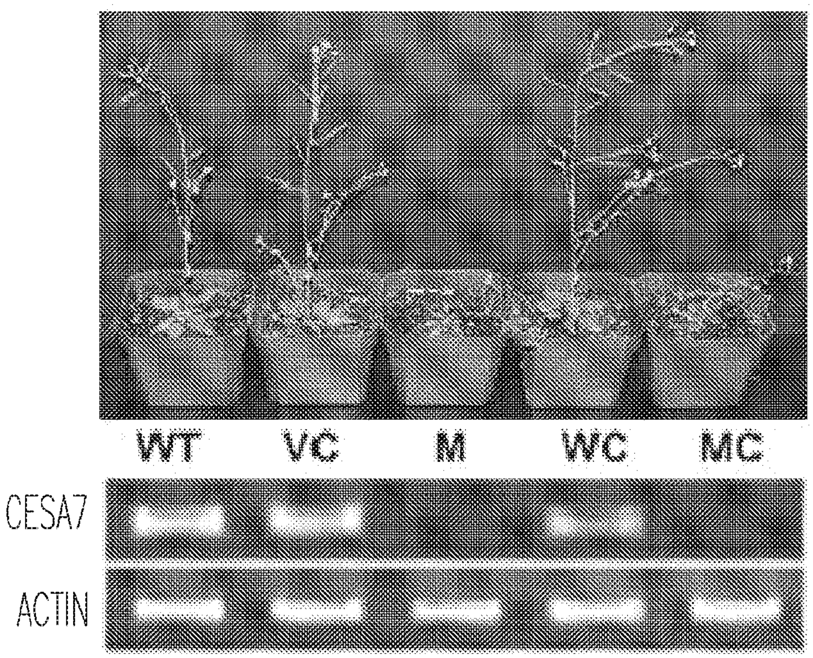
Figure 13D:
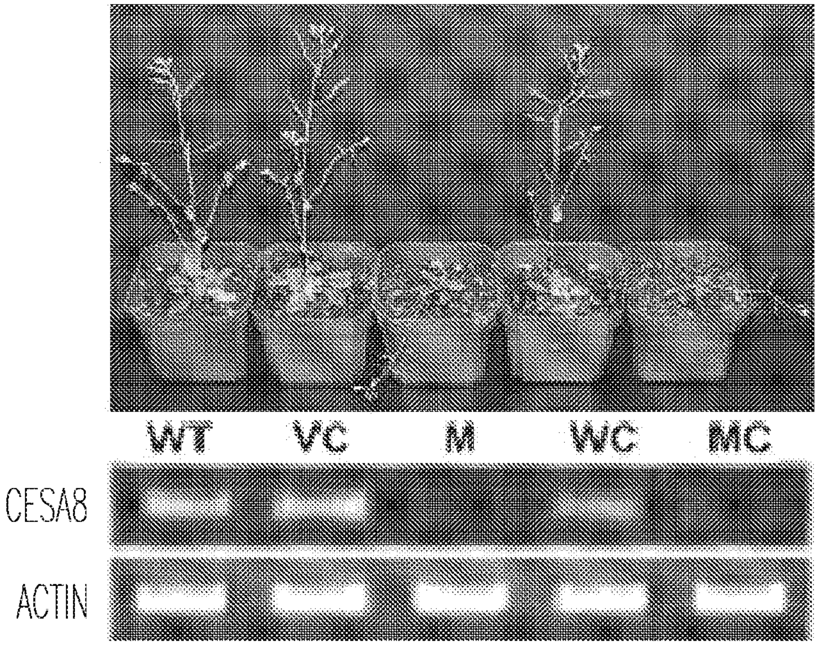

The resulting promoter-CESA construct was introduced into a binary vector pCB308 (Xiang et al., *Plant Molecular Biology* 40: 711-717 (1999)) and used in the *Agrobacterium*-mediated transformation of both wild-type *Arabidopsis* (Col-0) plants and cesa T-DNA insertion mutants. Homozygocity of these cesa mutants and their genetic complementation were confirmed by polymerase chain reaction amplification of the genomic DNA (FIG. 12).

RNA extraction and RT-PCR.

Total RNAs were extracted using Plant RNeasy extraction kit (Qiagen) according to the manufacturer's protocol. For RT-PCR analysis, total RNAs were first treated with DNaseI before the first-strand cDNA synthesis by SuperScript II Reverse Transcriptase (Invitrogen). RT-PCR was carried out using 1 μL of the reaction products as a template. Amplified DNA fragments were separated on 1% agarose gel and stained with ethidium bromide. The primers used for RT-PCR are shown in Table 1.

Histological Analysis.

The stem area located immediately above the rosette leaves (basal level) was cross-sectioned using Microtome (Leica RM2025) into thin sections (5 μm thick) and paraffin embedded as described previously (Ko et al., 2004 and 2007). The sections were then stained with 0.05% toluidine blue O for 1 min to visualize secondary xylem.

Results

Figure 10:
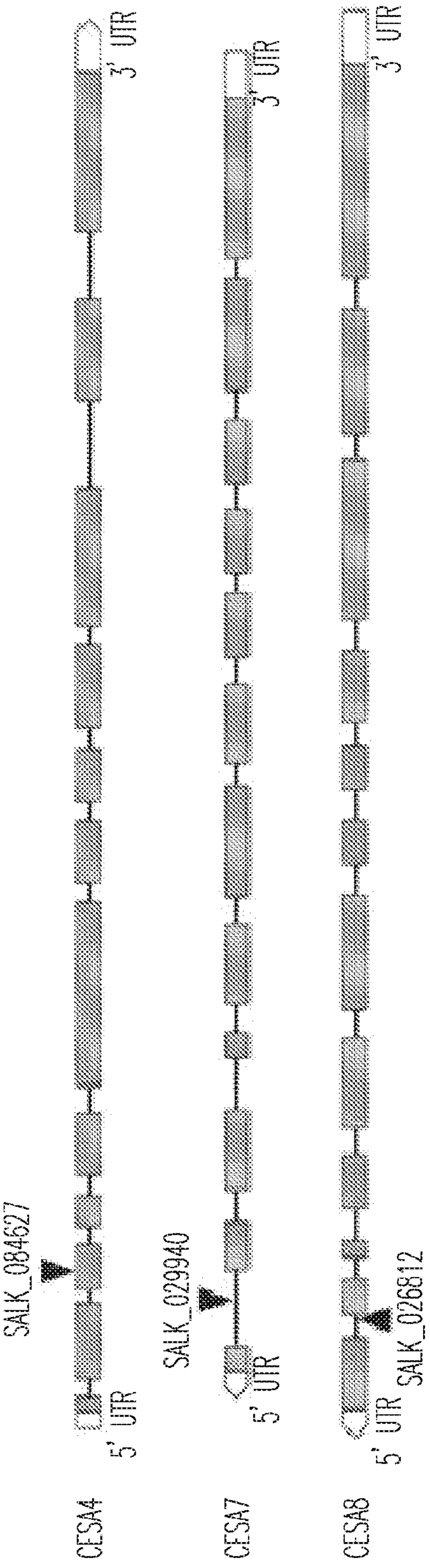
FIG. 10 is a schematic diagram showing T-DNA insertion sites in the cesa4, cesa7 and cesa8 mutants. The gray boxes represent exons, the black bars between the gray boxes represent introns and the white boxes represent UTRs. The black arrowheads indicate the site of T-DNA insertion.
Figure 14:
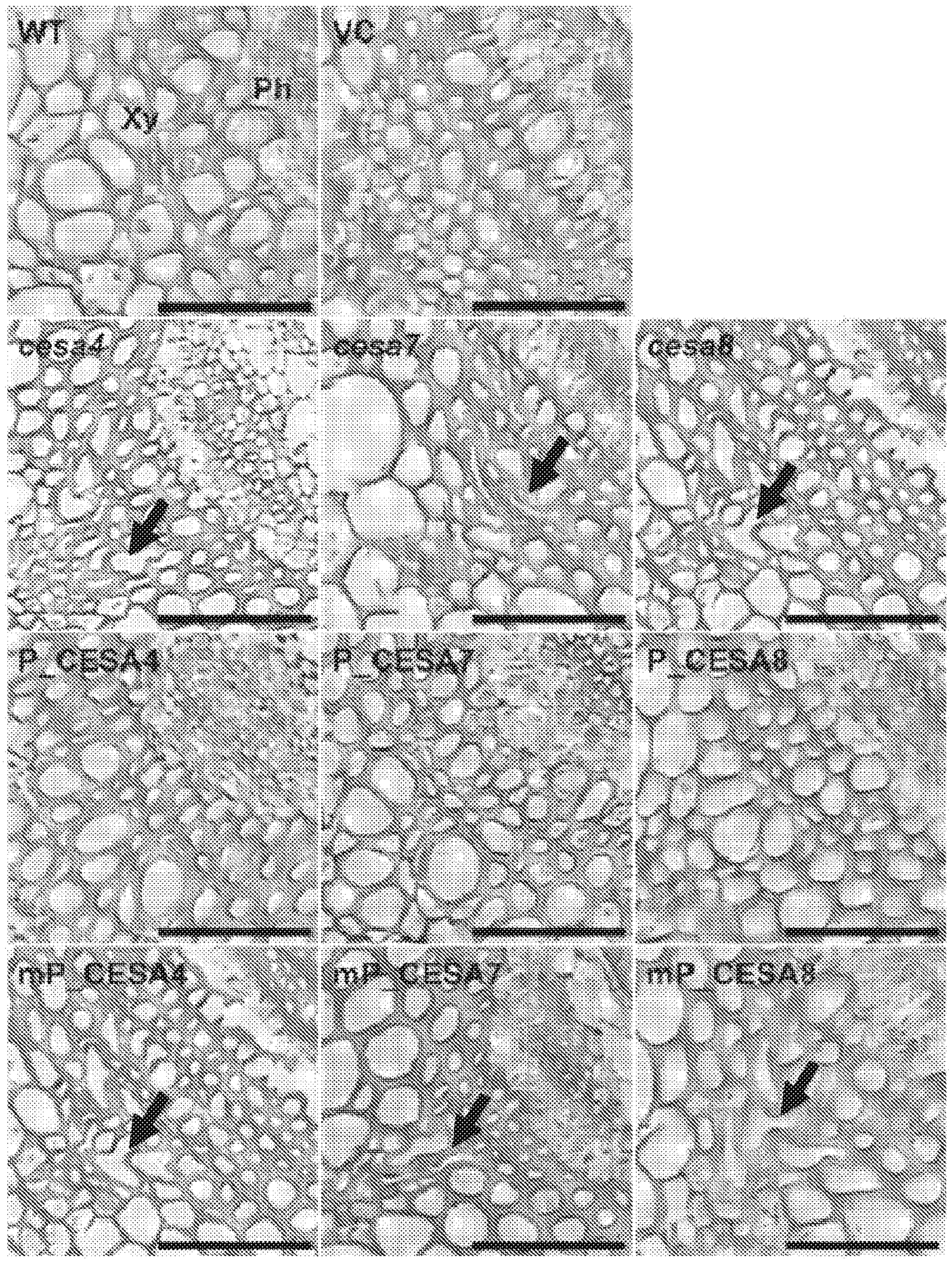
FIG. 14 shows stem cross-sections of wild-type, vector control, cesa T-DNA insertion mutants and their genetic complementations. All of the stems from the three mutants (cesa4, cesa7 and cesa8) show collapsed xylem phenotype. Stems from genetic complementation with native promoter-driven CESA CDSs recovered normal xylem phenotype, while those with mutated promoter-driven CDSs failed to do so. Arrows indicate collapsed xylem cells. Ph, phloem; Xy, xylem. Size bars represent 50 μm. Images are a representative of at least 15 plants observed in each wild-type and transgenic lines.

T-DNA insertional mutants of three secondary wall cesa (cesa4, cesa7, and cesa8) were obtained from *Arabidopsis* Biological Resource Center (see website at abrc.osu.edu/) (FIG. 10). All of the mutants displayed phenotypes such as collapsed/irregular xylem and pendent stem (FIG. 13 and FIG. 14). The three CESAs (CESA4, CESA7 and CESA8)

are required for cellulose synthesis in the secondary walls of *Arabidopsis* plants. Each of these three CESA genes appears to be equally important in the function of the cellulose synthase complex and one cannot substitute for another (Gardiner et al., *Plant Cell* 15: 1740-1748 (2003)). Therefore, even a single T-DNA insertion mutation of one the three CESA genes results in a severe phenotype (FIGS. 13 and 14).

Cells from each cesa mutant plant type were transformed with the corresponding CESA wild type coding region operably linked to either its native promoter or a mutated promoter. The mutated promoters had point mutations in the cis-regulatory element, M46RE, which is recognized by MYB 46, as shown in Table 2.

TABLE 2

Summary of Promoter Sequences

| Promoter Type | Wild Type | Mutant |
|---|---|---|
| CES44 (-404 to -397) | ATTTGGTA<br>SEQ ID NO: 65 | ATTTTTTA<br>SEQ ID NO: 72 |
| CESA4 (-218 to -211) | CACCAAAT<br>SEQ ID NO: 66 | CAAAAAAT<br>SEQ ID NO: 73 |
| CESA4 (-150 to -143) | GTTTGGTA<br>SEQ ID NO: 67 | GTTTTTTA<br>SEQ ID NO: 74 |
| CESA7 (-597 to -590) | CACCTAAT<br>SEQ ID NO: 68 | CAAATAAT<br>SEQ ID NO: 75 |
| CESA7 (-553 to -546) | CACCAAAC<br>SEQ ID NO: 69 | CAAAAAAC<br>SEQ ID NO: 76 |
| CESA8 (-446 to -439) | AGTTGGTG<br>SEQ ID NO: 70 | AGTTGGTG<br>SEQ ID NO: 77 |
| CESA8 (-140 to -133) | CACCAAAC<br>SEQ ID NO: 71 | CAAAAAAC<br>SEQ ID NO: 78 |

These mutations effectively eliminated MYB46 binding (Kim et al., Plant Molecular Biology 78: 489-501 (2012), herein incorporated by reference in its entirety), and resulted in failure of CESA expression (FIG. 13).

Both the wild-type and vector control plants grew upright and were normal in appearance. In contrast, the cesa mutants exhibited retarded growth and the characteristic 'pendent stem' phenotype (FIG. 13), with collapsed xylem (FIG. 14). Transgenic plants expressing native promoter-driven CESAs restored wild-type phenotype. However, genetic complementation with the mutant promoters that were not recognized by MYB46 exhibited the mutant phenotype (i.e., pendent stem and collapsed xylem phenotype) (FIGS. 13 and 14). These results indicate that MYB46 binding to the M46RE site is required for functional expression of the secondary wall CESAs in planta.

Transcription factor MYB46 and its orthologs have been shown to be master switches for the biosynthesis of the three major components of secondary walls (e.g., cellulose, hemicellulose, and lignin) in *Arabidopsis*, poplar, rice and maize. Furthermore, MYB46 has recently been shown to be a direct regulator of all three secondary wall CESA genes (CESA4, CESA7 and CESA8) (Kim et al., *Plant J* 73: 26-36 (2013), herein incorporated by reference in its entirety). Transcription factor MYB83 (NM_111685.2; GI:145338258), a homolog of MYB46, is functionally redundant with MYB46 and also operates by binding to M46RE. Double knockout of myb46/myb83 does not produce any viable plants (unpublished observation). In light of these observations, MYB46 plays a key role in the biosynthesis of secondary wall cellulose biosynthesis. However, the finding that MYB46/MYB83 is required for functional expression of all three secondary wall CESA genes is significant. Considering the importance of secondary wall cellulose synthesis for the growth and survival of the plant, additional regulators may operate in concert with MYB46 and/or may be involved in the transcriptional regulation of secondary wall CESA genes. In fact, the inventors have recently reported several candidate regulators (e.g., MYB112, WRKY11 and ERF6)) of CESA4, albeit none of them appears to be involved in the MYB46-mediated regulation pathway (Kim et al., 2013). Some of the secondary wall NAC transcription factors such as VND6, VND7, NST1 and NST2 bind to an imperfect palindromic 19-bp consensus sequence (SNBE), which is similar to M46RE (Zhong et al., 2010). Recently, Ohashi-Ito et al. (2010) reported the binding of VND6 to the promoter of CESA4. VND7 was also suggested as a direct regulator of CESA4 and CESA8 (Yamaguchi et al., 2011). However, none of the secondary wall CESA genes was directly induced by estradiol-activated VND7 (Zhong et al., 2010). The presence of multiple regulators supports the notion that the transcriptional regulation of cellulose biosynthesis is multifaceted and complex.

So far, MYB46/MYB83 is the only transcription factor shown to be direct regulator of all three secondary wall CESAs. The fact that MYB46 is required for functional expression of the three secondary wall CESAs indicates that MYB46 is necessary component of the transcriptional regulatory complex for the CESA regulation.

REFERENCES

1. Delmer D P (1999) CELLULOSE BIOSYNTHESIS: Exciting Times for A Difficult Field of Study. *Annu Rev Plant Physiol Plant Mol Biol* 50: 245-276.
2. Ragauskas A J, et al. (2006) The path forward for biofuels and biomaterials. *Science* 311 (5760): 484-489.
3. Pear J R, Kawagoe Y, Schreckengost W E, Delmer D P, & Stalker D M (1996) Higher plants contain homologs of the bacterial celA genes encoding the catalytic subunit of cellulose synthase. *Proc Natl Acad Sci USA* 93 (22): 12637-12642.
4. Somerville C (2006) Cellulose synthesis in higher plants. *Anna Rev Cell Dev Biol* 22: 53-78.
5. Endler A & Persson S (2011) Cellulose synthases and synthesis in *Arabidopsis. Mol Plant* 4 (2): 199-211.
6. Richmond T A & Somerville C R (2001) Integrative approaches to determining Cs1 function. *Plant Mol Biol* 47(1-2): 131-143.
7. Doblin M S, Kurek I, Jacob-Wilk D, & Delmer D P (2002) Cellulose biosynthesis in plants: from genes to rosettes. *Plant Cell Physiol* 43(12): 1407-1420.
8. Williamson R E, Burn J E, & Hocart C H (2002) Towards the mechanism of cellulose synthesis. *Trends Plant Sci* 7(10): 461-467.
9. Kumar M, et al. (2009) An update on the nomenclature for the cellulose synthase genes in Populus. *Trends Plant Sci* 14(5): 248-254.
10. Sjöström E (1992). Wood Chemistry Fundamentals and Applications, second edition. Academic Press. San Diego.
11. Carpita N & McCann M (2000) The cell wall. In Biochemistry and Molecular Biology of Plants. Edited by Buchanan B B, Gruissem W, Jones R L pp. 52-108. American Society of Plant Physiologists, Rockville, Md.

12. Somerville C, et al. (2004) Toward a systems approach to understanding plant cell walls. *Science* 306(5705): 2206-2211.
13. Cosgrove D J (2005) Growth of the plant cell wall. *Nat Rev Mol Cell Biol* 6(11): 850-861.
14. Demura T & Ye Z H (2010) Regulation of plant biomass production. *Curr Opin Plant Biol* 13(3): 299-304.
15. Ko J H, Yang S H, Park A H, Lerouxel O, Han K H (2007) ANAC012, a member of the plant-specific NAC transcription factor family, negatively regulates xylary fiber development in *Arabidopsis thaliana. Plant J* 50(6): 1035-1048.
16. Ko J H, Kim W C, & Han K H (2009) Ectopic expression of MYB46 identifies transcriptional regulatory genes involved in secondary wall biosynthesis in *Arabidopsis. Plant J* 60(4): 649-665.
17. Mitsuda N, Seki M, Shinozaki K, & Ohme-Takagi M (2005) The NAC transcription factors NST1 and NST2 of *Arabidopsis* regulate secondary wall thickenings and are required for anther dehiscence. *Plant Cell* 17(11): 2993-3006.
18. Mitsuda N, et al. (2007) NAC transcription factors, NST1 and NST3, are key regulators of the formation of secondary walls in woody tissues of *Arabidopsis. Plant Cell* 19(1): 270-280.
19. Zhong R & Ye Z H (2007) Regulation of cell wall biosynthesis. *Curr Opin Plant Biol* 10(6): 564-572.
20. Zhong R, Richardson E A, & Ye Z H (2007) The MYB46 transcription factor is a direct target of SND1 and regulates secondary wall biosynthesis in *Arabidopsis. Plant Cell* 19(9): 2776-2792.
21. Zhong R, Lee C, Zhou J, McCarthy R L, & Ye Z H (2008) A battery of transcription factors involved in the regulation of secondary cell wall biosynthesis in *Arabidopsis. Plant Cell* 20(10): 2763-2782.
22. Zhong R, Lee C, & Ye Z H (2010) Evolutionary conservation of the transcriptional network regulating secondary cell wall biosynthesis. *Trends Plant Sci* 15(11): 625-632.
23. Taylor N G, Howells R M, Huttly A K, Vickers K, & Turner S R (2003) Interactions among three distinct CesA proteins essential for cellulose synthesis. *Proc Natl Acad Sci USA* 100(3): 1450-1455.
24. Sablowski R W &. Meyerowitz E M (1998) A homolog of NO APICAL MERISTEM is an immediate target of the floral homeotic genes APETALA3/PISTILLATA. *Cell* 92(1): 93-103.
25. Wagner D, Sablowski R W, & Meyerowitz E M (1999) Transcriptional activation of APETALA1 by LEAFY. *Science* 285(5427): 582-584.
26. Baudry A, et al. (2004) TT2, TT8, and TTG1 synergistically specify the expression of BANYULS and proanthocyanidin biosynthesis in *Arabidopsis thaliana. Plant J* 39(3):366-380.
27. Blake A W, et al. (2006) Understanding the biological rationale for the diversity of cellulose-directed carbohydrate-binding modules in prokaryotic enzymes. *J Biol Chem* 281(39): 29321-29329.
28. Joshi C P, et al. (2004) Genomics of cellulose biosynthesis in poplars. *New Phytol* 164:53-61.
29. Joshi C P & Mansfield S D (2007) The cellulose paradox—simple molecule, complex biosynthesis. *Curr Opin. Plant Biol* 10(3): 220-226.
30. McCarthy R L, et al. (2010) The poplar MYB transcription factors, PtrMYB3 and PtrMYB20, are involved in the regulation of secondary wall biosynthesis. *Plant Cell Physiol* 51(6): 1084-1090.
31. Zhong R, et al. (2011) Transcriptional activation of secondary wall biosynthesis by rice and maize NAC and MYB transcription factors. *Plant Cell Physiol* 52(10): 1856-1871.
32. Zhou J, Lee C, Zhong R, & Ye Z H (2009) MYB58 and MYB63 are transcriptional activators of the lignin biosynthetic pathway during secondary cell wall formation in *Arabidopsis. Plant Cell* 21(1):248-266.
33. McCarthy R L, Zhong R, & Ye Z H (2009) MYB83 is a direct target of SND1 and acts redundantly with MYB46 in the regulation of secondary cell wall biosynthesis in *Arabidopsis. Plant Cell Physiol* 50(11): 1950-1964.
34. Zhong R, Ye Z-H. (2012) MYB46 and MYB83 bind to the SMRE sites and directly activate a suite of transcription factors and secondary wall biosynthetic genes. *Plant and Cell Physiology* 53: 368-380.
35. Zhong R, Morrison W H, III, Freshour G D, Hahn M G, Ye Z-H. (2003) Expression of a mutant form of cellulose synthase AtCesA7 causes dominant negative effect on cellulose biosynthesis. *Plant Physiology* 132: 786-795.
36. Yamaguchi M, Mitsuda N, Ohtani M, Ohme-Takagi M, Kato K, Demura T. (2011) VASCULAR-RELATED NAC-DOMAIN7 directly regulates the expression of a broad range of genes for xylem vessel formation. *The Plant Journal* 66: 579-590.
37. Xiang C, Han P, Lutziger I, Oliver D J. (1999) A mini binary vector series for plant transformation. *Plant Molecular Biology* 40: 711-717.
38. Turner S R, Somerville C R. (1997) Collapsed xylem phenotype of *Arabidopsis* identifies mutants deficient in cellulose deposition in the secondary cell wall. *Plant Cell* 9: 689-701.
39. Taylor N, Gardiner J, Whiteman R, Turner S. (2004) Cellulose synthesis in the *Arabidopsis* secondary cell wall. *Cellulose* 11: 329-338.
40. Taylor N G, Scheible W R, Cutler S, Somerville C R, Turner S R. (1999) The irregular xylem3 locus of *Arabidopsis* encodes a cellulose synthase required for secondary cell wall synthesis. *Plant Cell* 769-780.
41. Ohashi-Ito K, Oda Y. Fukuda H. (2010) *Arabidopsis* VASCULAR-RELATED NAC-DOMAIN6 directly regulates the genes that govern programmed cell death and secondary wall formation during xylem differentiation. *Plant Cell* 22: 3461-3473.
42. Ko J-H, Kim W-C, Kim J-Y, Ahan S J, Han K-H. (2012) MYB46-mediated transcriptional regulation of secondary wall biosynthesis. *Molecular Plant* 5: 961-962.
43. Ko J-H, Han K.-H, Park S, Yang J. (2004) Plant body weight-induced secondary growth in *Arabidopsis* and its transcription phenotype revealed by whole-transcriptome profiling. *Plant Physiology* 135: 1069-1083.
44. Kim W-C, Ko J-H, Kim J-Y, Kim J M, Bae H J, Han K-H. (2013) MYB46 directly regulates the gene expression of secondary wall-associated cellulose synthases in *Arabidopsis. Plant J* 73: 26-36.
45. Kim W-C, Ko J-H, Han K. H. (2012) Identification of a cis-acting regulatory motif recognized by MYB46, a master transcriptional regulator of secondary wall biosynthesis. *Plant Molecular Biology* 78: 489-501.
46. Gardiner J C, Taylor N G, Turner. S R. 2003. Control of cellulose synthase complex localization in developing xylem. *Plant Cell* 15: 1740-1748.
47. Brown R M. (2004) Cellulose structure and biosynthesis: what is in store for the 21st century? Journal of Polymer Science. Part A. *Polymer Chemistry* 42: 487-495.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims. As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acid or polypeptide preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The following statements of the invention are intended to describe and summarize various embodiments of the invention according to the foregoing description in the specification.

Statements Describing Aspects of the Invention

1. A method of increasing expression of a cellulose synthase gene in a plant comprising providing conditions in the plant for a transcription factor to bind to a promoter or enhancer region operably linked to a coding region of the cellulose synthase, wherein the transcription factor is selected from the group consisting of MYB46, HAM1, HAM2, MYB112, WRKY11, ERF6, and any combination thereof.
2. The method of statement 1, wherein providing conditions for a transcription factor to bind to a promoter or enhancer comprises transforming cells of the plant with a transgene encoding the transcription factor and/or generating a plant from plant cells comprising the isolated nucleic encoding the transcription factor.
3. The method of statement 1 or 2, wherein providing conditions for a transcription factor to bind to a promoter or enhancer comprises transforming cells of the plant with a transgene encoding the transcription factor wherein the transgene comprises a transgene promoter segment operably linked to a nucleic acid segment encoding the transcription factor.
4. The method of statement 3, wherein the transgene promoter segment is heterologous to the transcription factor's native gene.
5. The method of statement 3 or 4, wherein the transgene promoter segment is a strong promoter, weak promoter, inducible promoter, tissue specific promoter, developmentally regulated promoter or a combination thereof.
6. The method of any of statements 1-5, wherein the promoter or enhancer region operably linked to the cellulose synthase gene is the gene's native promoter.
7. The method of any of statements 1-6 wherein the promoter or enhancer region operably linked to the cellulose synthase gene is a nucleic acid segment with a sequence comprising any of SEQ ID NOs: 3-11, 65-71, or any combination thereof.
8. The method of any of any of statements 1-7, wherein the transcription factor has an amino acid sequence with at least 75% sequence identity, or at least 80% sequence identity, or at least 90% sequence identity, or at least 95% sequence identity to an amino acid sequence comprising any of SEQ ID NOs: 2, 13, 15, 17, 19, 21 or a combination thereof.
9. The method of any of any of statements 1-8, wherein the transcription factor has an amino acid sequence comprising or consisting essentially of any of SEQ ID NOs: 2, 13, 15, 17, 19, 21 or any combination thereof.
10. The method of any of statements 1-9, wherein the cellulose synthase is active in synthesizing secondary wall cellulose.
11. The method of any of statements 1-10, wherein the cellulose synthase is a CESA4.
12. The method of any of statements 1-11, wherein the cellulose synthase is a CESA4 gene with a promoter having a nucleotide sequence selected from the group consisting of any of SEQ ID NO:3-5, 65-67, and any combination thereof.
13. The method of any of statements 1-12, wherein the cellulose synthase is a CESA4 and the CESA4 expression is increased by a transcription factor selected from the group consisting of MYB46, HAM1, HAM2, MYB112, WRKY11, ERF6 and any combination thereof.
14. The method of any of statements 1-13, wherein the cellulose synthase is a CESA7.
15. The method of any of statements 1-14, wherein the cellulose synthase is a CESA7 gene with a promoter having a nucleotide sequence selected from the group consisting of any of SEQ ID NO:6-8, 68, 69, and any combination thereof.
16. The method of any of statement 1-5, wherein the cellulose synthase is a CESA7 and the CESA7 expression is increased by a transcription factor selected from the group consisting of MYB46, HAM2 and a combination thereof.

17. The method of any of statements 1-16, wherein the cellulose synthase is a CESA8.

18. The method of any of statements 1-17, wherein the cellulose synthase is a CESA8 gene with a promoter having a nucleotide sequence selected from the group consisting of any of SEQ ID NO:9-11, 70, 71, and any combination thereof.

19. The method of any of statements 1-18, wherein the cellulose synthase is a CESA8 and the CESA8 expression is increased by a MYB46 transcription factor.

20. An isolated nucleic acid encoding a plant gene promoter or a plant gene enhancer comprising a nucleotide sequence selected from the group consisting of any of SEQ ID NOs: 3-11, 65-71, or a combination thereof.

21. A transgene comprising a plant gene promoter or a plant gene enhancer comprising a nucleotide sequence selected from the group consisting of any of SEQ ID NOs: 3-11, 65-71, or a combination thereof.

22. A transgene comprising a transgene promoter segment and a segment encoding a plant transcription factor selected from the group consisting of MYB46, HAM1, HAM2, MBY112, WRKY11, ERF6, or a combination thereof.

23. The transgene of statement 22, wherein the transgene promoter segment is heterologous to the transcription factor's native gene.

24. The transgene of statement 22 or 23, wherein the transgene promoter segment is a strong promoter, weak promoter, inducible promoter, tissue specific promoter, developmentally regulated promoter or a combination thereof.

25. The transgene of any of statements 22-24, wherein the transcription factor has an amino acid sequence comprising any of SEQ ID NOs: 2, 13, 15, 17, 19, 21 or a combination thereof.

26. A kit comprising:
   a. a container comprising an isolated nucleic acid encoding a plant gene promoter or a plant gene enhancer comprising a nucleotide sequence selected from the group consisting of any of SEQ ID NOs: 3-11, 65-71, or a combination thereof; and
   b. instructions for operably linking the isolated promoter or enhancer nucleic acid to a selected coding region.

27. The kit of statement 26, wherein the instructions comprise a method for operably linking the isolated promoter or enhancer nucleic acid to a selected coding region in vitro.

28. The kit of statement 26, wherein the instructions comprise a method for operably linking the isolated promoter or enhancer nucleic acid to a selected coding region in vivo.

29. The kit of any of statements 26-28, wherein the selected coding region is a plant gene coding region.

30. The kit of any of statements 26-29, wherein the selected coding region is a plant cellulose synthase gene coding region.

31. The kit of any of statements 26-30, further comprising a second container comprising an isolated nucleic acid encoding is a plant cellulose synthase.

32. The kit of any of statements 26-31, wherein the isolated nucleic acid encoding is a plant cellulose synthase in the second container comprises a heterologous promoter segment and a segment encoding the plant cellulose synthase.

33. The kit of statement 32, wherein the heterologous promoter is a strong promoter, weak promoter, inducible promoter, tissue specific promoter, developmentally regulated promoter or a combination thereof.

34. A plant comprising an isolated nucleic acid encoding a plant transcription factor selected from the group consisting of MYB46, HAM1, HAM2, MYB112, WRKY11, ERF6, or a combination thereof.

35. The plant of statement 34, wherein the isolated nucleic acid comprises a heterologous promoter segment operably linked to a nucleic segment that encodes the plant transcription factor coding region.

36. The plant of statement 34 or 35, wherein the heterologous promoter is not the plant transcription factor's natural promoter.

37 The plant of statement 36, wherein the heterologous promoter is a strong, weak, inducible, tissue specific, developmentally regulated or a combination thereof.

38. The plant of any of statements 34-37, wherein the isolated nucleic acid expresses increased levels of the plant transcription factor in the plant compared to a corresponding transcription factor gene naturally present in a wild type plant of the same species.

39. The plant of any of statements 34-38, wherein the plant has increased levels of secondary wall cellulose compared to a wild type plant of the same species without the isolated nucleic acid.

40. The plant of any of statements 34-39, wherein the plant has at least about 1%, at least about 2%, at least about 3%, at least about 4%, at least about 5%, at least about 10%, at least about 15%, at least about 20%, at least about 25%, at least about 30% increased cellulose content compared to a wild type plant of the same species that does not have the isolated nucleic acid.

41. The plant of any of statements 34-40, wherein the plant is a transgenic plant, a genetically modified plant, or a plant selectively bred to comprise the isolated nucleic acid.

42. The plant of any of statements 34-41, wherein the plant transcription factor is MYB46.

43. The plant of any of statements 34-42, wherein the plant is a grass species, softwood species, or hardwood species.

44. The plant of any of statements 34-43, wherein the plant grass species is maize, barley, oats, rice, sorghum, millet, rye, switchgrass, prairie grass, wheat grass, sudangrass, sorghum, and straw-producing plants.

45. The plant of any of statements 34-44, wherein the plant is a poplar species, pine species, or eucalyptus species.

46. A seed comprising an isolated nucleic acid encoding a plant transcription factor selected from the group consisting of MYB46, HAM1, HAM2, MYB112, WRKY11, ERF6, or a combination thereof.

47. The seed of statement 46, wherein the isolated nucleic acid comprises a heterologous promoter segment operably linked to a nucleic segment that encodes the plant transcription factor coding region.

48. The seed of statement 47, wherein the heterologous promoter is not the plant transcription factor's natural promoter.

49. The seed of statement 47 or 48, wherein the heterologous promoter is a strong, weak, inducible, tissue specific, developmentally regulated or a combination thereof.
50. The seed of any statements 46-49, wherein the plant is a grass species, softwood species, or hardwood species.
51. The seed of any statements 46-50, wherein the plant grass species is maize, barley, oats, rice, sorghum, millet, rye, switchgrass, prairie grass, wheat grass, sudangrass, sorghum, and straw-producing plants.
52. The seed of any statements 46-51, wherein the plant is a poplar species, pine species, or eucalyptus species.
53. A plant biomass comprising secondary wall cellulose isolated from a plant comprising an isolated nucleic acid encoding a plant transcription factor selected from the group consisting of MYB46, HAM1, HAM2, MYB112, WRKY11, ERF6, or a combination thereof.
54. A kit comprising:
  a. a container comprising an isolated nucleic acid encoding a plant gene promoter or a plant gene enhancer comprising a nucleotide sequence selected from the group consisting of any of SEQ ID NOs: 3-11, 65-71, or a combination thereof, operably linked to an isolated nucleic acid comprising a coding region of a plant cellulose synthase, and
  b. instructions for transforming a plant cell with the isolated nucleic acid to generate a transformed plant cell.

The invention has been described broadly and generically herein. Each of the narrower species and subgeneric groupings faking within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Other embodiments are described within the following claims.

What is claimed:

1. A plant comprising a heterologous nucleic acid comprising a tissue specific promoter operably linked to a nucleic acid segment encoding a WRKY11 plant transcription factor having at least 95% sequence identity to SEQ ID NO:19, and wherein the plant has at least 4% increased levels of secondary wall cellulose compared to a wild type plant of the same species without the heterologous nucleic acid.

2. The plant of claim 1, wherein the plant is a softwood plant or hardwood plant.

3. The plant of claim 1, wherein the plant is a poplar species, pine species, or eucalyptus species plant.

4. The plant of claim 1, wherein the promoter is a xylem-specific promoter.

5. The plant of claim 1, wherein the heterologous nucleic acid expresses increased levels of the WRKY11 plant transcription factor in the plant compared to a corresponding transcription factor gene naturally present in a wild type plant of the same species.

6. The plant of claim 1, wherein the plant is a transgenic plant, a genetically modified plant, or a plant selectively bred to comprise the heterologous nucleic acid.

7. A seed from the plant of claim 1.

8. A plant biomass comprising secondary wall cellulose isolated from a plant comprising a heterologous nucleic acid comprising a tissue specific promoter segment operably linked to a nucleic acid segment encoding a WRKY11 plant transcription factor, wherein the WRKY11 has at least 95% sequence identity to SEQ ID NO:19.

9. A method of increasing cellulose content in a plant comprising expressing WRKY11 in the plant from a heterologous nucleic acid comprising a heterologous tissue specific promoter segment operably linked to a nucleic acid segment encoding the transcription factor, wherein the WRKY11 has at least 95% sequence identity to SEQ ID NO:19, and wherein the plant has at least 4% increased levels of secondary wall cellulose compared to a wild type plant of the same species without the heterologous nucleic acid.

10. A plant comprising a heterologous nucleic acid comprising a secondary wall cellulose synthase (CESA) promoter operably linked to a nucleic acid segment encoding a WRKY11 plant transcription factor having at least 95% sequence identity to SEQ NO:19, and wherein the plant has at least 4% increased levels of secondary wall cellulose compared to a wild type plant of the same species without the heterologous nucleic acid.

11. The plant of claim 10, wherein the promoter is a secondary wall cellulose synthase 4 (CESA4) promoter, or a secondary wall cellulose synthase 7 (CESA7) promoter operably linked to a nucleic acid segment encoding the WRKY11 plant transcription factor.

* * * * *

SEQUENCE LISTING

```
<160> NUMBER OF SEQ ID NOS: 79

<210> SEQ ID NO 1
<211> LENGTH: 843
<212> TYPE: DNA
<213> ORGANISM: Arabidopsis thaliana
<220> FEATURE:

<400> SEQUENCE: 1

atgaggaagc cagaggtagc cattgcagct agtactcacc aagtaaagaa gatgaagaag      60

ggactttggt ctcctgagga agactcaaag ctgatgcaat acatgttaag caatggacaa     120

ggatgttgga gtgatgttgc gaaaaacgca ggacttcaaa gatgtggcaa aagctgccgt     180

cttcgttgga tcaactatct tcgtcctgac ctcaagcgtg gcgctttctc tcctcaagaa     240

gaggatctca tcattcgctt tcattccatc ctcggcaaca ggtggtctca gattgcagca     300

cgattgcctg gtcggaccga taacgagatc aagaatttct ggaactcaac aataaagaaa     360

aggctaaaga agatgtccga tacctccaac ttaatcaaca actcatcctc atcacccaac     420

acagcaagcg attcctcttc taattccgca tcttctttgg atattaaaga cattatagga     480

agcttcatgt ccttacaaga acaaggcttc gtcaaccctt ccttgaccca catacaaacc     540

aacaatccat ttccaacggg aaacatgatc agccacccgt gcaatgacga ttttacccct     600

tatgtagatg gtatctatgg agtaaacgca ggggtacaag gggaactcta cttcccacct     660

ttggaatgtg aagaaggtga ttggtacaat gcaaatataa acaaccactt agacgagttg     720

aacactaatg gatccggaaa cgcacctgag ggtatgagac cagtggaaga attttgggac     780

cttgaccagt tgatgaacac tgaggttcct tcgttttact tcaacttcaa acaaagcata     840

tga                                                                   843

<210> SEQ ID NO 2
<211> LENGTH: 280
<212> TYPE: PRT
<213> ORGANISM: Arabidopsis thaliana

<400> SEQUENCE: 2

Met Arg Lys Pro Glu Val Ala Ile Ala Ala Ser Thr His Gln Val Lys
1               5                   10                  15
```

-continued

```
Lys Met Lys Lys Gly Leu Trp Ser Pro Glu Glu Asp Ser Lys Leu Met
            20                  25                  30

Gln Tyr Met Leu Ser Asn Gly Gln Gly Cys Trp Ser Asp Val Ala Lys
        35                  40                  45

Asn Ala Gly Leu Gln Arg Cys Gly Lys Ser Cys Arg Leu Arg Trp Ile
    50                  55                  60

Asn Tyr Leu Arg Pro Asp Leu Lys Arg Gly Ala Phe Ser Pro Gln Glu
65                  70                  75                  80

Glu Asp Leu Ile Ile Arg Phe His Ser Ile Leu Gly Asn Arg Trp Ser
                85                  90                  95

Gln Ile Ala Ala Arg Leu Pro Gly Arg Thr Asp Asn Glu Ile Lys Asn
            100                 105                 110

Phe Trp Asn Ser Thr Ile Lys Lys Arg Leu Lys Lys Met Ser Asp Thr
        115                 120                 125

Ser Asn Leu Ile Asn Asn Ser Ser Ser Ser Pro Asn Thr Ala Ser Asp
    130                 135                 140

Ser Ser Ser Asn Ser Ala Ser Ser Leu Asp Ile Lys Asp Ile Ile Gly
145                 150                 155                 160

Ser Phe Met Ser Leu Gln Glu Gln Gly Phe Val Asn Pro Ser Leu Thr
                165                 170                 175

His Ile Gln Thr Asn Asn Pro Phe Pro Thr Gly Asn Met Ile Ser His
            180                 185                 190

Pro Cys Asn Asp Asp Phe Thr Pro Tyr Val Asp Gly Ile Tyr Gly Val
        195                 200                 205

Asn Ala Gly Val Gln Gly Glu Leu Tyr Phe Pro Pro Leu Glu Cys Glu
    210                 215                 220

Glu Gly Asp Trp Tyr Asn Ala Asn Ile Asn Asn His Leu Asp Glu Leu
225                 230                 235                 240

Asn Thr Asn Gly Ser Gly Asn Ala Pro Glu Gly Met Arg Pro Val Glu
                245                 250                 255

Glu Phe Trp Asp Leu Asp Gln Leu Met Asn Thr Glu Val Pro Ser Phe
            260                 265                 270

Tyr Phe Asn Phe Lys Gln Ser Ile
        275                 280


<210> SEQ ID NO 3
<211> LENGTH: 25
<212> TYPE: DNA
<213> ORGANISM: Arabidopsis thaliana

<400> SEQUENCE: 3

tcactcacag tttggtacaa cctca                                            25


<210> SEQ ID NO 4
<211> LENGTH: 25
<212> TYPE: DNA
<213> ORGANISM: Arabidopsis thaliana

<400> SEQUENCE: 4

tcactcacag tgtggtacaa cctca                                            25


<210> SEQ ID NO 5
<211> LENGTH: 25
<212> TYPE: DNA
<213> ORGANISM: Arabidopsis thaliana

<400> SEQUENCE: 5
```

tcactcacag ttttgtacaa cctca 25

<210> SEQ ID NO 6
<211> LENGTH: 25
<212> TYPE: DNA
<213> ORGANISM: Arabidopsis thaliana

<400> SEQUENCE: 6
cagaaaattc acctaattaa ggaca 25

<210> SEQ ID NO 7
<211> LENGTH: 25
<212> TYPE: DNA
<213> ORGANISM: Arabidopsis thaliana

<400> SEQUENCE: 7
cagaaaattc acctgattaa ggaca 25

<210> SEQ ID NO 8
<211> LENGTH: 25
<212> TYPE: DNA
<213> ORGANISM: Arabidopsis thaliana

<400> SEQUENCE: 8
cagaaaattc acataattaa ggaca 25

<210> SEQ ID NO 9
<211> LENGTH: 25
<212> TYPE: DNA
<213> ORGANISM: Arabidopsis thaliana

<400> SEQUENCE: 9
cttatagaaa gttggtgatt gaaaa 25

<210> SEQ ID NO 10
<211> LENGTH: 25
<212> TYPE: DNA
<213> ORGANISM: Arabidopsis thaliana

<400> SEQUENCE: 10
cttatagaaa ggtggtgatt gaaaa 25

<210> SEQ ID NO 11
<211> LENGTH: 25
<212> TYPE: DNA
<213> ORGANISM: Arabidopsis thaliana

<400> SEQUENCE: 11
cttatagaaa gtttgtgatt gaaaa 25

<210> SEQ ID NO 12
<211> LENGTH: 1338
<212> TYPE: DNA
<213> ORGANISM: Arabidopsis thaliana

<400> SEQUENCE: 12
atgggatcgt ctgcggatac agagacggcg atgataatcg ccacaccggc gtcgaaccat 60
aataatccgg caaccaacgg cggagatgcg aatcagaatc atacttctgg tgcgatactc 120
gctctcacga attcagaatc ggatgcttcg aagaagagaa gaatgggggt gcttccgctc 180
gaggttggta ctcgcgtgat gtgtcaatgg agagacggaa aataccatcc ggtgaaggtt 240
atcgagcgcc gaaagaatta taatggtggt cacaatgatt acgagtacta cgttcattac 300

-continued

```
acagagttta atagaagatt ggatgaatgg attaagcttg aacagcttga ccttgattca    360

gtagagtgtg ctttagatga aaaagttgaa gacaaggtga ctagcttgaa gatgacacga    420

caccagaaac ggaagattga tgagactcat gtagagggtc atgaagagct ggatgctgcc    480

agtttgcgtg aacacgagga gttcacgaaa gtgaagaaca tagctacgat tgagcttggg    540

aagtatgaga ttgagacgtg gtacttctct ccttttcctc cagaatacaa tgactgcgtg    600

aagctctttt tctgtgagtt ttgcctcagt tttatgaagc gcaaagagca gcttcaaaga    660

catatgagga aatgcgattt gaagcacccc cctggggatg aaatctatcg aagctctact    720

ttgtcaatgt ttgaggtgga tggcaagaag aataaggtct atgcacagaa cctctgttat    780

ctggcaaagt tatttcttga ccacaaaact ctttactatg acgttgattt gttcctgttc    840

tatattctct gtgaatgtga tgatcgtgga tgccacatgg ttggatactt ttcaaaggaa    900

aaacactcag aagaagctta caacttggct tgcatcctta cacttcctcc atatcaaagg    960

aagggctatg gcaaattctt aatagccttc tcctatgaac tctcaaagaa agagggcaaa   1020

gtcgggacac cggaaaggcc gctctctgat ctagggttag tgagttacag aggttactgg   1080

actcggattt tattagacat tttgaaaaag cacaagggaa acatatctat caaggagctg   1140

agcgacatga cagcgattaa agcagaagat atattaagca ccctgcagag cttggaactg   1200

atacaataca ggaaaggaca acacgtaatc tgcgcggatc ctaaggtact ggaccgacac   1260

ttgaaagcgg caggccgagg tggtcttgat gtggatgtga gcaaaatgat atggactcct   1320

tacaaagagc agagctaa                                                 1338
```

<210> SEQ ID NO 13
<211> LENGTH: 445
<212> TYPE: PRT
<213> ORGANISM: Arabidopsis thaliana

<400> SEQUENCE: 13

```
Met Gly Ser Ser Ala Asp Thr Glu Thr Ala Met Ile Ile Ala Thr Pro
1               5                   10                  15

Ala Ser Asn His Asn Asn Pro Ala Thr Asn Gly Gly Asp Ala Asn Gln
            20                  25                  30

Asn His Thr Ser Gly Ala Ile Leu Ala Leu Thr Asn Ser Glu Ser Asp
        35                  40                  45

Ala Ser Lys Lys Arg Arg Met Gly Val Leu Pro Leu Glu Val Gly Thr
    50                  55                  60

Arg Val Met Cys Gln Trp Arg Asp Gly Lys Tyr His Pro Val Lys Val
65                  70                  75                  80

Ile Glu Arg Arg Lys Asn Tyr Asn Gly Gly His Asn Asp Tyr Glu Tyr
                85                  90                  95

Tyr Val His Tyr Thr Glu Phe Asn Arg Arg Leu Asp Glu Trp Ile Lys
            100                 105                 110

Leu Glu Gln Leu Asp Leu Asp Ser Val Glu Cys Ala Leu Asp Glu Lys
        115                 120                 125

Val Glu Asp Lys Val Thr Ser Leu Lys Met Thr Arg His Gln Lys Arg
    130                 135                 140

Lys Ile Asp Glu Thr His Val Glu Gly His Glu Glu Leu Asp Ala Ala
145                 150                 155                 160

Ser Leu Arg Glu His Glu Glu Phe Thr Lys Val Lys Asn Ile Ala Thr
                165                 170                 175

Ile Glu Leu Gly Lys Tyr Glu Ile Glu Thr Trp Tyr Phe Ser Pro Phe
```

```
            180                 185                 190

Pro Pro Glu Tyr Asn Asp Cys Val Lys Leu Phe Phe Cys Glu Phe Cys
        195                 200                 205

Leu Ser Phe Met Lys Arg Lys Glu Gln Leu Gln Arg His Met Arg Lys
    210                 215                 220

Cys Asp Leu Lys His Pro Pro Gly Asp Glu Ile Tyr Arg Ser Ser Thr
225                 230                 235                 240

Leu Ser Met Phe Glu Val Asp Gly Lys Lys Asn Lys Val Tyr Ala Gln
                245                 250                 255

Asn Leu Cys Tyr Leu Ala Lys Leu Phe Leu Asp His Lys Thr Leu Tyr
            260                 265                 270

Tyr Asp Val Asp Leu Phe Leu Phe Tyr Ile Leu Cys Glu Cys Asp Asp
        275                 280                 285

Arg Gly Cys His Met Val Gly Tyr Phe Ser Lys Glu Lys His Ser Glu
    290                 295                 300

Glu Ala Tyr Asn Leu Ala Cys Ile Leu Thr Leu Pro Pro Tyr Gln Arg
305                 310                 315                 320

Lys Gly Tyr Gly Lys Phe Leu Ile Ala Phe Ser Tyr Glu Leu Ser Lys
                325                 330                 335

Lys Glu Gly Lys Val Gly Thr Pro Glu Arg Pro Leu Ser Asp Leu Gly
            340                 345                 350

Leu Val Ser Tyr Arg Gly Tyr Trp Thr Arg Ile Leu Leu Asp Ile Leu
        355                 360                 365

Lys Lys His Lys Gly Asn Ile Ser Ile Lys Glu Leu Ser Asp Met Thr
    370                 375                 380

Ala Ile Lys Ala Glu Asp Ile Leu Ser Thr Leu Gln Ser Leu Glu Leu
385                 390                 395                 400

Ile Gln Tyr Arg Lys Gly Gln His Val Ile Cys Ala Asp Pro Lys Val
                405                 410                 415

Leu Asp Arg His Leu Lys Ala Ala Gly Arg Gly Gly Leu Asp Val Asp
            420                 425                 430

Val Ser Lys Met Ile Trp Thr Pro Tyr Lys Glu Gln Ser
        435                 440                 445
```

<210> SEQ ID NO 14
<211> LENGTH: 1338
<212> TYPE: DNA
<213> ORGANISM: Arabidopsis thaliana

<400> SEQUENCE: 14

```
atgggatcgt cagcgaatac agaaaccaac ggcaacgcac cgccaccgtc gtcgaatcaa      60

aagcctccgg ctacgaacgg cgttgatggg tctcatcctc ctcctcctcc tttaactcct     120

gatcaagcta ttatagagtc ggatccgtcg aagaagagga aaatggggat gcttcctcta     180

gaagtgggta ctcgtgtgat gtgtcggtgg agagacggga aacaccatcc ggtgaaagta     240

attgagcgcc ggcggataca taacggcggt caaaatgatt acgagtatta cgttcattac     300

actgagttta ataggaggct ggatgaatgg actcagctgg accaactgga ccttgattca     360

gtagagtgcg ctgtagatga aaaagtggaa gacaaggtaa caagcttgaa gatgacacgt     420

caccagaaga ggaagatcga tgagacacat atagagggtc atgaagagct ggatgcagca     480

agtttgcgtg aacatgaaga gttcacgaaa gtgaagaaca tatcaacaat tgagcttgga     540

aaatatgaga ttgagacttg gtacttctcc ccttttccgc cagaatacaa tgactgtgtg     600

aagctctttt tttgtgagtt ttgcctgaac ttcatgaaac gcaaagagca gcttcaaagg     660
```

```
catatgagga agtgtgacct gaagcaccca cctggtgatg aaatttaccg aagtggtacc    720

ttgtcaatgt ttgaggtaga tggcaaaaag aacaaggttt atgcacagaa tctctgctac    780

ctggcaaagt tatttcttga ccacaaaact ctttactacg atgttgattt gtttctattc    840

tacgttcttt gcgaatgtga tgaccgagga tgccacatgg ttgggtactt ttcaaaggag    900

aagcattcgg aagaagcata caacttagct tgcattctaa ccctgccttc atatcaaaga    960

aaaggctatg gaaagttctt aatagccttt tcctatgaac tgtcaaagaa agagggaaaa   1020

gttgggacac cggaaagacc cttgtcggat ctaggcttac taagctacag aggttattgg   1080

actcgtgttc tattagaaat cttgaaaaaa cataagggaa acatttctat caaggagctg   1140

agcgacgtga cagcaatcaa agcggaagat atattaagca cacttcagag cctagaactg   1200

atacagtaca ggaaaggaca gcatgtgatc tgtgcggatc caaaggttct ggaccgacat   1260

ctgaaagctg caggccgagg tggtcttgat gtagatgcta gcaaactgat ttggacacct   1320

tacaaggacc agagttaa                                                 1338
```

<210> SEQ ID NO 15
<211> LENGTH: 445
<212> TYPE: PRT
<213> ORGANISM: Arabidopsis thaliana

<400> SEQUENCE: 15

```
Met Gly Ser Ser Ala Asn Thr Glu Thr Asn Gly Asn Ala Pro Pro Pro
1               5                   10                  15

Ser Ser Asn Gln Lys Pro Pro Ala Thr Asn Gly Val Asp Gly Ser His
            20                  25                  30

Pro Pro Pro Pro Pro Leu Thr Pro Asp Gln Ala Ile Ile Glu Ser Asp
        35                  40                  45

Pro Ser Lys Lys Arg Lys Met Gly Met Leu Pro Leu Glu Val Gly Thr
    50                  55                  60

Arg Val Met Cys Arg Trp Arg Asp Gly Lys His His Pro Val Lys Val
65                  70                  75                  80

Ile Glu Arg Arg Arg Ile His Asn Gly Gly Gln Asn Asp Tyr Glu Tyr
                85                  90                  95

Tyr Val His Tyr Thr Glu Phe Asn Arg Arg Leu Asp Glu Trp Thr Gln
            100                 105                 110

Leu Asp Gln Leu Asp Leu Asp Ser Val Glu Cys Ala Val Asp Glu Lys
        115                 120                 125

Val Glu Asp Lys Val Thr Ser Leu Lys Met Thr Arg His Gln Lys Arg
    130                 135                 140

Lys Ile Asp Glu Thr His Ile Glu Gly His Glu Glu Leu Asp Ala Ala
145                 150                 155                 160

Ser Leu Arg Glu His Glu Glu Phe Thr Lys Val Lys Asn Ile Ser Thr
                165                 170                 175

Ile Glu Leu Gly Lys Tyr Glu Ile Glu Thr Trp Tyr Phe Ser Pro Phe
            180                 185                 190

Pro Pro Glu Tyr Asn Asp Cys Val Lys Leu Phe Phe Cys Glu Phe Cys
        195                 200                 205

Leu Asn Phe Met Lys Arg Lys Glu Gln Leu Gln Arg His Met Arg Lys
    210                 215                 220

Cys Asp Leu Lys His Pro Pro Gly Asp Glu Ile Tyr Arg Ser Gly Thr
225                 230                 235                 240

Leu Ser Met Phe Glu Val Asp Gly Lys Lys Asn Lys Val Tyr Ala Gln
```

```
                245                 250                 255

Asn Leu Cys Tyr Leu Ala Lys Leu Phe Leu Asp His Lys Thr Leu Tyr
            260                 265                 270

Tyr Asp Val Asp Leu Phe Leu Phe Tyr Val Leu Cys Glu Cys Asp Asp
        275                 280                 285

Arg Gly Cys His Met Val Gly Tyr Phe Ser Lys Glu Lys His Ser Glu
    290                 295                 300

Glu Ala Tyr Asn Leu Ala Cys Ile Leu Thr Leu Pro Ser Tyr Gln Arg
305                 310                 315                 320

Lys Gly Tyr Gly Lys Phe Leu Ile Ala Phe Ser Tyr Glu Leu Ser Lys
                325                 330                 335

Lys Glu Gly Lys Val Gly Thr Pro Glu Arg Pro Leu Ser Asp Leu Gly
            340                 345                 350

Leu Leu Ser Tyr Arg Gly Tyr Trp Thr Arg Val Leu Leu Glu Ile Leu
        355                 360                 365

Lys Lys His Lys Gly Asn Ile Ser Ile Lys Glu Leu Ser Asp Val Thr
    370                 375                 380

Ala Ile Lys Ala Glu Asp Ile Leu Ser Thr Leu Gln Ser Leu Glu Leu
385                 390                 395                 400

Ile Gln Tyr Arg Lys Gly Gln His Val Ile Cys Ala Asp Pro Lys Val
                405                 410                 415

Leu Asp Arg His Leu Lys Ala Ala Gly Arg Gly Gly Leu Asp Val Asp
            420                 425                 430

Ala Ser Lys Leu Ile Trp Thr Pro Tyr Lys Asp Gln Ser
        435                 440                 445
```

<210> SEQ ID NO 16
<211> LENGTH: 732
<212> TYPE: DNA
<213> ORGANISM: Arabidopsis thaliana

<400> SEQUENCE: 16

```
atgaatataa gtagaacaga attcgcaaac tgtaaaaccc ttataaatca taaagaagaa      60

gtcgaagaag tcgagaaaaa gatggaaata gaaataagga gaggtccatg gactgtggaa     120

gaagacatga agctcgtcag ttacatttct cttcacggtg aaggaagatg gaactccctc     180

tctcgttctg ctggactgaa tagaacgggg aaaagttgca gattgcggtg gctaaattat     240

ctccggccgg atatccgccg tggagacata tcccttcaag aacaatttat catccttgaa     300

ctccattctc gttggggaaa tcggtggtca aagattgctc aacatttacc gggaagaaca     360

gataacgaga taaagaatta ttggagaaca cgtgttcaaa agcatgcaaa acttctaaaa     420

tgtgacgtga acagcaagca attcaaagac accatcaaac atctctggat gcctcgtctc     480

atcgagagaa tcgccgccac tcaaagtgtc caatttacct ctaaccacta ctcgcctgag     540

aactccagcg tcgccaccgc cacgtcatca acgtcgtcgt ctgaggctgt gagatcgagt     600

ttctacggtg gtgatcaggt ggaatttgga acgttggatc atatgacaaa tggtggttat     660

tggttcaacg gcggagatac gtttgaaact ttgtgtagtt ttgacgagct caacaagtgg     720

ctcatacagt ag                                                         732
```

<210> SEQ ID NO 17
<211> LENGTH: 243
<212> TYPE: PRT
<213> ORGANISM: Arabidopsis thaliana

<400> SEQUENCE: 17

```
Met Asn Ile Ser Arg Thr Glu Phe Ala Asn Cys Lys Thr Leu Ile Asn
1               5                   10                  15

His Lys Glu Glu Val Glu Glu Val Glu Lys Lys Met Glu Ile Glu Ile
            20                  25                  30

Arg Arg Gly Pro Trp Thr Val Glu Glu Asp Met Lys Leu Val Ser Tyr
        35                  40                  45

Ile Ser Leu His Gly Glu Gly Arg Trp Asn Ser Leu Ser Arg Ser Ala
    50                  55                  60

Gly Leu Asn Arg Thr Gly Lys Ser Cys Arg Leu Arg Trp Leu Asn Tyr
65                  70                  75                  80

Leu Arg Pro Asp Ile Arg Arg Gly Asp Ile Ser Leu Gln Glu Gln Phe
                85                  90                  95

Ile Ile Leu Glu Leu His Ser Arg Trp Gly Asn Arg Trp Ser Lys Ile
            100                 105                 110

Ala Gln His Leu Pro Gly Arg Thr Asp Asn Glu Ile Lys Asn Tyr Trp
        115                 120                 125

Arg Thr Arg Val Gln Lys His Ala Lys Leu Leu Lys Cys Asp Val Asn
    130                 135                 140

Ser Lys Gln Phe Lys Asp Thr Ile Lys His Leu Trp Met Pro Arg Leu
145                 150                 155                 160

Ile Glu Arg Ile Ala Ala Thr Gln Ser Val Gln Phe Thr Ser Asn His
                165                 170                 175

Tyr Ser Pro Glu Asn Ser Ser Val Ala Thr Ala Thr Ser Ser Thr Ser
            180                 185                 190

Ser Ser Glu Ala Val Arg Ser Ser Phe Tyr Gly Gly Asp Gln Val Glu
        195                 200                 205

Phe Gly Thr Leu Asp His Met Thr Asn Gly Gly Tyr Trp Phe Asn Gly
    210                 215                 220

Gly Asp Thr Phe Glu Thr Leu Cys Ser Phe Asp Glu Leu Asn Lys Trp
225                 230                 235                 240

Leu Ile Gln
```

<210> SEQ ID NO 18
<211> LENGTH: 978
<212> TYPE: DNA
<213> ORGANISM: Arabidopsis thaliana

<400> SEQUENCE: 18

```
atggccgtcg atctaatgcg tttccctaag atagatgatc aaacggctat tcaggaagct     60

gcatcgcaag gtttacaaag tatggaacat ctgatccgtg tcctctctaa ccgtcccgaa    120

caacaacaca acgttgactg ctccgagatc actgacttca ccgtttctaa attcaaaacc    180

gtcatttctc tccttaaccg tactggtcac gctcggttca gacgcggacc ggttcactcc    240

acttcctctg ccgcatctca gaaactacag agtcagatcg ttaaaaatac tcaacctgag    300

gctccgatag tgagaacaac tacgaatcac cctcaaatcg ttcctccacc gtctagtgta    360

acactcgatt tctctaaacc aagcatcttc ggcaccaaag ctaagagcgc cgagctggaa    420

ttctccaaag aaaacttcag tgtttcttta aactcctcat tcatgtcgtc ggcgataacc    480

ggagacggca gcgtctccaa tggaaaaatc ttccttgctt ctgctccgtt gcagcctgtt    540

aactcttccg gaaaaccacc gttggctggt catccttaca gaaagagatg tctcgagcat    600

gagcactcag agagtttctc cggaaaagtc tccggctccg cctacggaaa gtgccattgc    660

aagaaaagca ggaaaaatcg gatgaagaga accgtgagag taccggcgat aagtgcaaag    720
```

-continued atcgccgata ttccaccgga cgaatattcg tggaggaagt acggacaaaa accgatcaag 780
ggctcaccac acccacgtgg ttactacaag tgcagtacat tcagaggatg tccagcgagg 840
aaacacgtgg aacgagcatt agatgatcca gcgatgctta ttgtgacata cgaaggagag 900
caccgtcata accaatccgc gatgcaggag aatatttctt cttcaggcat taatgattta 960
gtgtttgcct cggcttga 978

<210> SEQ ID NO 19
<211> LENGTH: 325
<212> TYPE: PRT
<213> ORGANISM: Arabidopsis thaliana

<400> SEQUENCE: 19

```
Met Ala Val Asp Leu Met Arg Phe Pro Lys Ile Asp Asp Gln Thr Ala
1               5                   10                  15

Ile Gln Glu Ala Ala Ser Gln Gly Leu Gln Ser Met Glu His Leu Ile
            20                  25                  30

Arg Val Leu Ser Asn Arg Pro Glu Gln Gln His Asn Val Asp Cys Ser
        35                  40                  45

Glu Ile Thr Asp Phe Thr Val Ser Lys Phe Lys Thr Val Ile Ser Leu
    50                  55                  60

Leu Asn Arg Thr Gly His Ala Arg Phe Arg Arg Gly Pro Val His Ser
65                  70                  75                  80

Thr Ser Ser Ala Ala Ser Gln Lys Leu Gln Ser Gln Ile Val Lys Asn
                85                  90                  95

Thr Gln Pro Glu Ala Pro Ile Val Arg Thr Thr Thr Asn His Pro Gln
            100                 105                 110

Ile Val Pro Pro Pro Ser Ser Val Thr Leu Asp Phe Ser Lys Pro Ser
        115                 120                 125

Ile Phe Gly Thr Lys Ala Lys Ser Ala Glu Leu Glu Phe Ser Lys Glu
    130                 135                 140

Asn Phe Ser Val Ser Leu Asn Ser Ser Phe Met Ser Ser Ala Ile Thr
145                 150                 155                 160

Gly Asp Gly Ser Val Ser Asn Gly Lys Ile Phe Leu Ala Ser Ala Pro
                165                 170                 175

Leu Gln Pro Val Asn Ser Ser Gly Lys Pro Pro Leu Ala Gly His Pro
            180                 185                 190

Tyr Arg Lys Arg Cys Leu Glu His Glu His Ser Glu Ser Phe Ser Gly
        195                 200                 205

Lys Val Ser Gly Ser Ala Tyr Gly Lys Cys His Cys Lys Lys Ser Arg
    210                 215                 220

Lys Asn Arg Met Lys Arg Thr Val Arg Val Pro Ala Ile Ser Ala Lys
225                 230                 235                 240

Ile Ala Asp Ile Pro Pro Asp Glu Tyr Ser Trp Arg Lys Tyr Gly Gln
                245                 250                 255

Lys Pro Ile Lys Gly Ser Pro His Pro Arg Gly Tyr Tyr Lys Cys Ser
            260                 265                 270

Thr Phe Arg Gly Cys Pro Ala Arg Lys His Val Glu Arg Ala Leu Asp
        275                 280                 285

Asp Pro Ala Met Leu Ile Val Thr Tyr Glu Gly Glu His Arg His Asn
    290                 295                 300

Gln Ser Ala Met Gln Glu Asn Ile Ser Ser Ser Gly Ile Asn Asp Leu
305                 310                 315                 320
```

Val Phe Ala Ser Ala
325

<210> SEQ ID NO 20
<211> LENGTH: 849
<212> TYPE: DNA
<213> ORGANISM: Arabidopsis thaliana

<400> SEQUENCE: 20
atggctacac caaacgaagt atcagctctt ttcctcatca agaagtatct cctcgacgaa 60
ttgtctccgt tgcctactac tgccaccacc aatcgatgga tgaacgattt cacgtcattt 120
gatcaaaccg gtttcgagtt ttctgaattt gaaaccaaac cggaaataat cgatctcgtc 180
actcccaaac cggagatttt tgatttcgat gtgaaatctg aaattccatc tgaatcgaac 240
gattccttca cgttccaatc gaatcctcct cgcgttactg ttcaatccaa tcgaaaaccg 300
ccgttgaaga tcgcaccacc gaaccgaacc aagtggattc aattcgcaac cggaaatcct 360
aaaccggaac ttcccgtacc ggttgtagca gcagaggaga agaggcatta cagaggagtg 420
aggatgaggc cgtgggggaa attcgcggcg gagattcgag acccgactcg tcgtggaact 480
cgtgtttggc tcgggacgtt tgagacggcg atcgaagcgg ctagagctta cgacaaagaa 540
gcgtttagac tacgaggatc aaaggcgatt ctgaatttcc cgcttgaagt tgacaagtgg 600
aatccacgcg ctgaagatgg tcgtggcctg tacaacaaac ggaagagaga cggcgaggag 660
gaggaagtga cggtggttga gaaagtgcta aagacggagg agagttacga cgttagcggc 720
ggcgagaatg ttgagtcagg tttgacggcg atagatgact gggatttgac ggagtttctg 780
agcatgccgc ttttatcgcc gttatctcca cacccaccgt ttggttatcc acaattgacc 840
gttgtttga 849

<210> SEQ ID NO 21
<211> LENGTH: 282
<212> TYPE: PRT
<213> ORGANISM: Arabidopsis thaliana

<400> SEQUENCE: 21

Met Ala Thr Pro Asn Glu Val Ser Ala Leu Phe Leu Ile Lys Lys Tyr
1 5 10 15

Leu Leu Asp Glu Leu Ser Pro Leu Pro Thr Thr Ala Thr Thr Asn Arg
20 25 30

Trp Met Asn Asp Phe Thr Ser Phe Asp Gln Thr Gly Phe Glu Phe Ser
35 40 45

Glu Phe Glu Thr Lys Pro Glu Ile Ile Asp Leu Val Thr Pro Lys Pro
50 55 60

Glu Ile Phe Asp Phe Asp Val Lys Ser Glu Ile Pro Ser Glu Ser Asn
65 70 75 80

Asp Ser Phe Thr Phe Gln Ser Asn Pro Pro Arg Val Thr Val Gln Ser
85 90 95

Asn Arg Lys Pro Pro Leu Lys Ile Ala Pro Pro Asn Arg Thr Lys Trp
100 105 110

Ile Gln Phe Ala Thr Gly Asn Pro Lys Pro Glu Leu Pro Val Pro Val
115 120 125

Val Ala Ala Glu Glu Lys Arg His Tyr Arg Gly Val Arg Met Arg Pro
130 135 140

Trp Gly Lys Phe Ala Ala Glu Ile Arg Asp Pro Thr Arg Arg Gly Thr
145 150 155 160

```
Arg Val Trp Leu Gly Thr Phe Glu Thr Ala Ile Glu Ala Ala Arg Ala
            165                 170                 175

Tyr Asp Lys Glu Ala Phe Arg Leu Arg Gly Ser Lys Ala Ile Leu Asn
        180                 185                 190

Phe Pro Leu Glu Val Asp Lys Trp Asn Pro Arg Ala Glu Asp Gly Arg
    195                 200                 205

Gly Leu Tyr Asn Lys Arg Lys Arg Asp Gly Glu Glu Glu Glu Val Thr
210                 215                 220

Val Val Glu Lys Val Leu Lys Thr Glu Glu Ser Tyr Asp Val Ser Gly
225                 230                 235                 240

Gly Glu Asn Val Glu Ser Gly Leu Thr Ala Ile Asp Asp Trp Asp Leu
            245                 250                 255

Thr Glu Phe Leu Ser Met Pro Leu Leu Ser Pro Leu Ser Pro His Pro
        260                 265                 270

Pro Phe Gly Tyr Pro Gln Leu Thr Val Val
    275                 280


<210> SEQ ID NO 22
<211> LENGTH: 39
<212> TYPE: DNA
<213> ORGANISM: Artificial Sequence
<220> FEATURE:
<223> OTHER INFORMATION: A synthetic primer

<400> SEQUENCE: 22

cccactagtt aaatcttatt tactaacaaa acaataaga                          39


<210> SEQ ID NO 23
<211> LENGTH: 28
<212> TYPE: DNA
<213> ORGANISM: Artificial Sequence
<220> FEATURE:
<223> OTHER INFORMATION: A synthetic primer

<400> SEQUENCE: 23

cccctcgagg gcgaggtaca ctgagctc                                      28


<210> SEQ ID NO 24
<211> LENGTH: 31
<212> TYPE: DNA
<213> ORGANISM: Artificial Sequence
<220> FEATURE:
<223> OTHER INFORMATION: A synthetic primer

<400> SEQUENCE: 24

gattcaagaa catagccaga ttttttaaag t                                  31


<210> SEQ ID NO 25
<211> LENGTH: 41
<212> TYPE: DNA
<213> ORGANISM: Artificial Sequence
<220> FEATURE:
<223> OTHER INFORMATION: A synthetic primer

<400> SEQUENCE: 25

tcttacttaa tattttgtat cttataaact ttaaaaaatc t                       41


<210> SEQ ID NO 26
<211> LENGTH: 28
<212> TYPE: DNA
<213> ORGANISM: Artificial Sequence
<220> FEATURE:
<223> OTHER INFORMATION: A synthetic primer
```

<400> SEQUENCE: 26
tgagctgtct ccttcttcca aaaaatct 28

<210> SEQ ID NO 27
<211> LENGTH: 31
<212> TYPE: DNA
<213> ORGANISM: Artificial Sequence
<220> FEATURE:
<223> OTHER INFORMATION: A synthetic primer

<400> SEQUENCE: 27
ttcaagagac agcaacaaga ttttttggaa g 31

<210> SEQ ID NO 28
<211> LENGTH: 30
<212> TYPE: DNA
<213> ORGANISM: Artificial Sequence
<220> FEATURE:
<223> OTHER INFORMATION: A synthetic primer

<400> SEQUENCE: 28
gacccaattt cactcacagt tttttacaac 30

<210> SEQ ID NO 29
<211> LENGTH: 32
<212> TYPE: DNA
<213> ORGANISM: Artificial Sequence
<220> FEATURE:
<223> OTHER INFORMATION: A synthetic primer

<400> SEQUENCE: 29
gttgtgaaga aaactgaggt tgtaaaaaac tg 32

<210> SEQ ID NO 30
<211> LENGTH: 28
<212> TYPE: DNA
<213> ORGANISM: Artificial Sequence
<220> FEATURE:
<223> OTHER INFORMATION: A synthetic primer

<400> SEQUENCE: 30
cccctcgaga tggaaccaaa caccatgg 28

<210> SEQ ID NO 31
<211> LENGTH: 21
<212> TYPE: DNA
<213> ORGANISM: Artificial Sequence
<220> FEATURE:
<223> OTHER INFORMATION: A synthetic primer

<400> SEQUENCE: 31
gtactgcaga gactcgaacc a 21

<210> SEQ ID NO 32
<211> LENGTH: 24
<212> TYPE: DNA
<213> ORGANISM: Artificial Sequence
<220> FEATURE:
<223> OTHER INFORMATION: A synthetic primer

<400> SEQUENCE: 32
tctctgcagt actcactaat gctc 24

<210> SEQ ID NO 33

<211> LENGTH: 28
<212> TYPE: DNA
<213> ORGANISM: Artificial Sequence
<220> FEATURE:
<223> OTHER INFORMATION: A synthetic primer

<400> SEQUENCE: 33
cccactagtt taacagtcga cgccacat 28

<210> SEQ ID NO 34
<211> LENGTH: 23
<212> TYPE: DNA
<213> ORGANISM: Artificial Sequence
<220> FEATURE:
<223> OTHER INFORMATION: A synthetic primer

<400> SEQUENCE: 34
caacagatga tgatgacttt gga 23

<210> SEQ ID NO 35
<211> LENGTH: 23
<212> TYPE: DNA
<213> ORGANISM: Artificial Sequence
<220> FEATURE:
<223> OTHER INFORMATION: A synthetic primer

<400> SEQUENCE: 35
agacctttga ggaatgggta gag 23

<210> SEQ ID NO 36
<211> LENGTH: 39
<212> TYPE: DNA
<213> ORGANISM: Artificial Sequence
<220> FEATURE:
<223> OTHER INFORMATION: A synthetic primer

<400> SEQUENCE: 36
cccgagctca gattgaggat cattttattt atttattag 39

<210> SEQ ID NO 37
<211> LENGTH: 24
<212> TYPE: DNA
<213> ORGANISM: Artificial Sequence
<220> FEATURE:
<223> OTHER INFORMATION: A synthetic primer

<400> SEQUENCE: 37
cccctcgaga gggacggccg gaga 24

<210> SEQ ID NO 38
<211> LENGTH: 32
<212> TYPE: DNA
<213> ORGANISM: Artificial Sequence
<220> FEATURE:
<223> OTHER INFORMATION: A synthetic primer

<400> SEQUENCE: 38
tagcttatgt atgcagaaaa ttcaaataat ta 32

<210> SEQ ID NO 39
<211> LENGTH: 31
<212> TYPE: DNA
<213> ORGANISM: Artificial Sequence
<220> FEATURE:
<223> OTHER INFORMATION: A synthetic primer

<400> SEQUENCE: 39
gttacgttcc ctgtccttaa ttatttgaat t 31

<210> SEQ ID NO 40
<211> LENGTH: 26
<212> TYPE: DNA
<213> ORGANISM: Artificial Sequence
<220> FEATURE:
<223> OTHER INFORMATION: A synthetic primer

<400> SEQUENCE: 40
tggcttgcac tcctctcaaa aaacct 26

<210> SEQ ID NO 41
<211> LENGTH: 31
<212> TYPE: DNA
<213> ORGANISM: Artificial Sequence
<220> FEATURE:
<223> OTHER INFORMATION: A synthetic primer

<400> SEQUENCE: 41
aaattagtta gggggtaagg ttttttgaga g 31

<210> SEQ ID NO 42
<211> LENGTH: 25
<212> TYPE: DNA
<213> ORGANISM: Artificial Sequence
<220> FEATURE:
<223> OTHER INFORMATION: A synthetic primer

<400> SEQUENCE: 42
cccctcgaga tggaagctag cgccg 25

<210> SEQ ID NO 43
<211> LENGTH: 21
<212> TYPE: DNA
<213> ORGANISM: Artificial Sequence
<220> FEATURE:
<223> OTHER INFORMATION: A synthetic primer

<400> SEQUENCE: 43
tgaggatcca tcaaaaaaca c 21

<210> SEQ ID NO 44
<211> LENGTH: 20
<212> TYPE: DNA
<213> ORGANISM: Artificial Sequence
<220> FEATURE:
<223> OTHER INFORMATION: A synthetic primer

<400> SEQUENCE: 44
gatggatcct cagattggaa 20

<210> SEQ ID NO 45
<211> LENGTH: 27
<212> TYPE: DNA
<213> ORGANISM: Artificial Sequence
<220> FEATURE:
<223> OTHER INFORMATION: A synthetic primer

<400> SEQUENCE: 45
cccgagctct cagcagttga tgccaca 27

<210> SEQ ID NO 46
<211> LENGTH: 23
<212> TYPE: DNA

<213> ORGANISM: Artificial Sequence
<220> FEATURE:
<223> OTHER INFORMATION: A synthetic primer

<400> SEQUENCE: 46
caacagatga tgatgacttt gga 23

<210> SEQ ID NO 47
<211> LENGTH: 23
<212> TYPE: DNA
<213> ORGANISM: Artificial Sequence
<220> FEATURE:
<223> OTHER INFORMATION: A synthetic primer

<400> SEQUENCE: 47
agacctttga ggaatgggta gag 23

<210> SEQ ID NO 48
<211> LENGTH: 21
<212> TYPE: DNA
<213> ORGANISM: Artificial Sequence
<220> FEATURE:
<223> OTHER INFORMATION: A synthetic primer

<400> SEQUENCE: 48
gcaagctacg aagaggtctc c 21

<210> SEQ ID NO 49
<211> LENGTH: 29
<212> TYPE: DNA
<213> ORGANISM: Artificial Sequence
<220> FEATURE:
<223> OTHER INFORMATION: A synthetic primer

<400> SEQUENCE: 49
cccactagtt gatggatggt tttgctgta 29

<210> SEQ ID NO 50
<211> LENGTH: 28
<212> TYPE: DNA
<213> ORGANISM: Artificial Sequence
<220> FEATURE:
<223> OTHER INFORMATION: A synthetic primer

<400> SEQUENCE: 50
cccctgcagc ttcgaattcc cctgtttg 28

<210> SEQ ID NO 51
<211> LENGTH: 40
<212> TYPE: DNA
<213> ORGANISM: Artificial Sequence
<220> FEATURE:
<223> OTHER INFORMATION: A synthetic primer

<400> SEQUENCE: 51
gattttaatt cttatttttc ttatagaaag tttttgattg 40

<210> SEQ ID NO 52
<211> LENGTH: 38
<212> TYPE: DNA
<213> ORGANISM: Artificial Sequence
<220> FEATURE:
<223> OTHER INFORMATION: A synthetic primer

<400> SEQUENCE: 52
ttataatttt taagtaaatc ttttcaatca aaaacttt 38

<210> SEQ ID NO 53
<211> LENGTH: 27
<212> TYPE: DNA
<213> ORGANISM: Artificial Sequence
<220> FEATURE:
<223> OTHER INFORMATION: A synthetic primer

<400> SEQUENCE: 53
tccgattttt cacaatccaa aaaactt 27

<210> SEQ ID NO 54
<211> LENGTH: 35
<212> TYPE: DNA
<213> ORGANISM: Artificial Sequence
<220> FEATURE:
<223> OTHER INFORMATION: A synthetic primer

<400> SEQUENCE: 54
aggaaaaaaa gttattaaaa aaagtttttt ggatt 35

<210> SEQ ID NO 55
<211> LENGTH: 30
<212> TYPE: DNA
<213> ORGANISM: Artificial Sequence
<220> FEATURE:
<223> OTHER INFORMATION: A synthetic primer

<400> SEQUENCE: 55
cccctgcaga tgatggagtc taggtctccc 30

<210> SEQ ID NO 56
<211> LENGTH: 21
<212> TYPE: DNA
<213> ORGANISM: Artificial Sequence
<220> FEATURE:
<223> OTHER INFORMATION: A synthetic primer

<400> SEQUENCE: 56
acaggatcca ttaaaaagca c 21

<210> SEQ ID NO 57
<211> LENGTH: 20
<212> TYPE: DNA
<213> ORGANISM: Artificial Sequence
<220> FEATURE:
<223> OTHER INFORMATION: A synthetic primer

<400> SEQUENCE: 57
aatggatcct gttgttggtc 20

<210> SEQ ID NO 58
<211> LENGTH: 31
<212> TYPE: DNA
<213> ORGANISM: Artificial Sequence
<220> FEATURE:
<223> OTHER INFORMATION: A synthetic primer

<400> SEQUENCE: 58
cccactagtt tagcaatcga tcaaaagaca g 31

<210> SEQ ID NO 59
<211> LENGTH: 23
<212> TYPE: DNA
<213> ORGANISM: Artificial Sequence
<220> FEATURE:

<223> OTHER INFORMATION: A synthetic primer

<400> SEQUENCE: 59
cgatgttaat atgagagggc ttg 23

<210> SEQ ID NO 60
<211> LENGTH: 23
<212> TYPE: DNA
<213> ORGANISM: Artificial Sequence
<220> FEATURE:
<223> OTHER INFORMATION: A synthetic primer

<400> SEQUENCE: 60
ggaaggatct tgaggttgtt tct 23

<210> SEQ ID NO 61
<211> LENGTH: 28
<212> TYPE: DNA
<213> ORGANISM: Artificial Sequence
<220> FEATURE:
<223> OTHER INFORMATION: A synthetic primer

<400> SEQUENCE: 61
gtacttatat gtctagcatg aatccctg 28

<210> SEQ ID NO 62
<211> LENGTH: 19
<212> TYPE: DNA
<213> ORGANISM: Artificial Sequence
<220> FEATURE:
<223> OTHER INFORMATION: A synthetic primer

<400> SEQUENCE: 62
attttgccga tttcggaac 19

<210> SEQ ID NO 63
<211> LENGTH: 21
<212> TYPE: DNA
<213> ORGANISM: Artificial Sequence
<220> FEATURE:
<223> OTHER INFORMATION: A synthetic primer

<400> SEQUENCE: 63
atgaagatta aggtcgtggc a 21

<210> SEQ ID NO 64
<211> LENGTH: 20
<212> TYPE: DNA
<213> ORGANISM: Artificial Sequence
<220> FEATURE:
<223> OTHER INFORMATION: A synthetic primer

<400> SEQUENCE: 64
tccgagtttg aagaggctac 20

<210> SEQ ID NO 65
<211> LENGTH: 8
<212> TYPE: DNA
<213> ORGANISM: Arabidopsis thaliana

<400> SEQUENCE: 65 atttggta 8

<210> SEQ ID NO 66
<211> LENGTH: 8

<212> TYPE: DNA
<213> ORGANISM: Arabidopsis thaliana

<400> SEQUENCE: 66 caccaaat 8

<210> SEQ ID NO 67
<211> LENGTH: 8
<212> TYPE: DNA
<213> ORGANISM: Arabidopsis thaliana

<400> SEQUENCE: 67 gtttggta 8

<210> SEQ ID NO 68
<211> LENGTH: 8
<212> TYPE: DNA
<213> ORGANISM: Arabidopsis thaliana

<400> SEQUENCE: 68 cacctaat 8

<210> SEQ ID NO 69
<211> LENGTH: 8
<212> TYPE: DNA
<213> ORGANISM: Arabidopsis thaliana

<400> SEQUENCE: 69 caccaaac 8

<210> SEQ ID NO 70
<211> LENGTH: 8
<212> TYPE: DNA
<213> ORGANISM: Arabidopsis thaliana

<400> SEQUENCE: 70 agttggtg 8

<210> SEQ ID NO 71
<211> LENGTH: 8
<212> TYPE: DNA
<213> ORGANISM: Arabidopsis thaliana

<400> SEQUENCE: 71 caccaaac 8

<210> SEQ ID NO 72
<211> LENGTH: 8
<212> TYPE: DNA
<213> ORGANISM: Arabidopsis thaliana

<400> SEQUENCE: 72 atttttta 8

<210> SEQ ID NO 73
<211> LENGTH: 8
<212> TYPE: DNA
<213> ORGANISM: Arabidopsis thaliana

<400> SEQUENCE: 73 caaaaaat 8

<210> SEQ ID NO 74

-continued

```
<211> LENGTH: 8
<212> TYPE: DNA
<213> ORGANISM: Arabidopsis thaliana

<400> SEQUENCE: 74

gtttttta                                                                 8


<210> SEQ ID NO 75
<211> LENGTH: 8
<212> TYPE: DNA
<213> ORGANISM: Arabidopsis thaliana

<400> SEQUENCE: 75

caaataat                                                                 8


<210> SEQ ID NO 76
<211> LENGTH: 8
<212> TYPE: DNA
<213> ORGANISM: Arabidopsis thaliana

<400> SEQUENCE: 76

caaaaaac                                                                 8


<210> SEQ ID NO 77
<211> LENGTH: 8
<212> TYPE: DNA
<213> ORGANISM: Arabidopsis thaliana

<400> SEQUENCE: 77

agttggtg                                                                 8


<210> SEQ ID NO 78
<211> LENGTH: 8
<212> TYPE: DNA
<213> ORGANISM: Arabidopsis thaliana

<400> SEQUENCE: 78

caaaaaac                                                                 8


<210> SEQ ID NO 79
<211> LENGTH: 24
<212> TYPE: DNA
<213> ORGANISM: Artificial Sequence
<220> FEATURE:
<223> OTHER INFORMATION: A synthetic primer

<400> SEQUENCE: 79

ggacgccatt gctgcttact gttg                                              24
```

UNITED STATES PATENT AND TRADEMARK OFFICE
CERTIFICATE OF CORRECTION

PATENT NO. : 10,837,025 B2  
APPLICATION NO. : 15/478661  
DATED : November 17, 2020  
INVENTOR(S) : Han et al.

It is certified that error appears in the above-identified patent and that said Letters Patent is hereby corrected as shown below:

In the Claims

In Column 87, Line 15, in Claim 10, delete "SEQ NO:19," and insert --SEQ ID NO:19,-- therefor Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*